(12) United States Patent
Day et al.

(10) Patent No.: US 11,986,450 B2
(45) Date of Patent: *May 21, 2024

(54) METHODS AND COMPOSITIONS FOR TREATING INFECTION AND INFLAMMATION WITH SELENOCYANATE

(71) Applicant: National Jewish Health, Denver, CO (US)

(72) Inventors: Brian J. Day, Englewood, CO (US); Preston E. Bratcher, Arvada, CO (US)

(73) Assignee: National Jewish Health, Denver, CO (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/735,368

(22) Filed: May 3, 2022

(65) Prior Publication Data
US 2022/0280467 A1    Sep. 8, 2022

Related U.S. Application Data

(60) Continuation of application No. 16/933,191, filed on Jul. 20, 2020, now Pat. No. 11,351,141, which is a division of application No. 16/116,409, filed on Aug. 29, 2018, now Pat. No. 10,751,315.

(60) Provisional application No. 62/551,615, filed on Aug. 29, 2017.

(51) Int. Cl.
| | |
|---|---|
| *A61K 31/21* | (2006.01) |
| *A61K 45/06* | (2006.01) |
| *A61P 11/00* | (2006.01) |
| *A61P 31/04* | (2006.01) |

(52) U.S. Cl.
CPC .............. *A61K 31/21* (2013.01); *A61K 45/06* (2013.01); *A61P 11/00* (2018.01); *A61P 31/04* (2018.01)

(58) Field of Classification Search
CPC ...................................... A61K 31/21
See application file for complete search history.

(56) References Cited

U.S. PATENT DOCUMENTS

| | | | |
|---|---|---|---|
| 5,591,761 A | 1/1997 | Chan et al. | |
| 6,702,998 B2 | 3/2004 | Conner | |
| 7,770,577 B2 | 8/2010 | Conner | |
| 9,308,234 B2 | 4/2016 | Arnold et al. | |
| 10,751,315 B2 * | 8/2020 | Day | A61P 31/04 |
| 11,351,141 B2 * | 6/2022 | Day | A61K 31/095 |
| 2002/0165215 A1 | 11/2002 | Lam et al. | |
| 2005/0163862 A1 | 7/2005 | Forceville et al. | |
| 2007/0142405 A1 | 6/2007 | Dong et al. | |
| 2007/0224275 A1 | 9/2007 | Reid et al. | |
| 2007/0225377 A1 | 9/2007 | Flatt et al. | |
| 2008/0108692 A1 | 5/2008 | Lam et al. | |
| 2009/0186038 A1 | 7/2009 | Reed | |
| 2010/0158966 A1 | 6/2010 | Reid et al. | |
| 2013/0058983 A1 | 3/2013 | Baker | |
| 2013/0129809 A1 | 5/2013 | Srivastava et al. | |

FOREIGN PATENT DOCUMENTS

| | | |
|---|---|---|
| EP | 0365763 | 5/1990 |
| WO | WO 2007/008293 | 1/2007 |
| WO | WO 2016/081594 | 5/2016 |

OTHER PUBLICATIONS

Chandler et al. "Antiinflammatory and Antimicrobial Effects of Thiocyanate in a Cystic Fibrosis Mouse Model," American Journal of Respiratory Cell and Molecular Biology, Aug. 2015, vol. 53, No. 2, pp. 193-205.
Chandler et al. "Thiocyanate: A potentially useful therapeutic agent with host defense and antioxidant properties," Biochemical Pharmacology, Dec. 2012, vol. 84, No. 11, pp. 1381-1387.
Cook et al. "Assessment and Treatment of Fungal Lung Infections," U.S. Pharmacist, Jul. 2011, vol. 36, No. 7, HS-17-HS-24, 12 pages.
Fragoso et al. Transcellular thiocyanate transport by human airway epithelia, The Journal of Physiology, Nov. 2004, vol. 561, No. 1, pp. 183-194.
Gerson et al. "The Lactoperoxidase System Functions in Bacterial Clearance of Airways," American Journal of Respiratory Cell and Molecular Biology, vol. 22, No. 6, Jun. 2000, pp. 665-671.
Jagannath et al. "Neuraminidase inhibitors for the treatment of influenza infection in people with cystic fibrosis," Cochrane Database of Systematic Reviews, Feb. 2014, vol. 10, No. 2, CD008139 (abstract).
Linsdell "Thiocyanate as a probe of the cystic fibrosis transmembrane conductance regulator chloride channel pore," Canadian Journal of Physiology and Pharmacology, 2001, vol. 79, pp. 573-579.
Lorentzen et al. "Concentration of the antibacterial precursor thiocyanate in cystic fibrosis airway secretions," Free Radical Biology and Medicine, May 2011, vol. 50, No. 9, pp. 1144-1150.
Lutfiyya et al. "Diagnosis and Treatment of Community-Acquired Pneumonia," American Family Physician, Feb. 2006, vol. 73, No. 3, pp. 442-450.
Lyczak et al. "Lung Infections Associated with Cystic Fibrosis," Clinical Microbiology Reviews, Apr. 2002, vol. 15, No. 2, pp. 194-222.
Maduh et al. "Protein Kinase C Modulation of Rhodanese-Catalyzed Conversion of Cyanide to Thiocyanate," Research Communications in Molecular Pathology and Pharmacology, Nov. 1994, vol. 86, No. 2, pp. 155-173.
Minarowski et al. "Thiocyanate concentration in saliva of cystic fibrosis patients," Folia Histochemica Et Cytobiologica, 2008, vol. 46, No. 2, pp. 245-246.

(Continued)

*Primary Examiner* — Rei Tsang Shiao
(74) *Attorney, Agent, or Firm* — Sheridan Ross P.C.

(57) ABSTRACT

The present invention generally relates to methods and compositions for treating pulmonary infections and inflammation with a composition comprising selenocyanate, hyposelenocyanite or a selenocyanate conjugate.

11 Claims, 27 Drawing Sheets

(56) References Cited

OTHER PUBLICATIONS

Schultz et al. "Thiocyanate Levels in Human Saliva: Quantitation by Fourier Transform Infrared Spectroscopy," Analytical Biochemistry, 1996, vol. 240, pp. 7-12.
Tang et al. "Mechanism of direct bicarbonate transport by the CFTR anion channel," Journal of Cystic Fibrosis, 2009, vol. 8, pp. 115-121.
Thomas et al. "Oxidation of Chloride and Thiocyanate by Isolated Leukocytes," The Journal of Biological Chemistry, Jul. 1986, vol. 261, No. 21, pp. 9694-9702.
Van Dalen et al. "Thiocyanate and chloride as competing substrates for myeloperoxidase," Biochemical Journal, 1997, vol. 327, pp. 487-492.
International Search Report and Written Opinion for International (PCT) Patent Application No. PCT/US2018/048554, dated Oct. 25, 2018 11 pages.
International Preliminary Report on Patentability for International (PCT) Patent Application No. PCT/US2018/048554, dated Mar. 12, 2020 10 pages.
Extended Search Report for European Patent Application No. 1852222.1, dated Apr. 19, 2021 9 pages.

\* cited by examiner

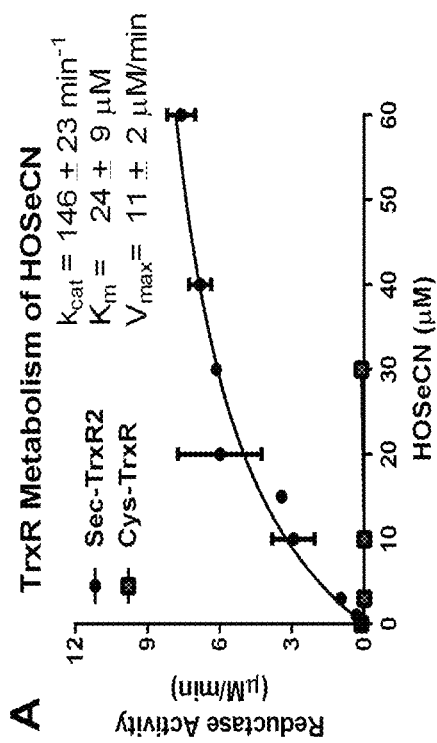
FIG. 12
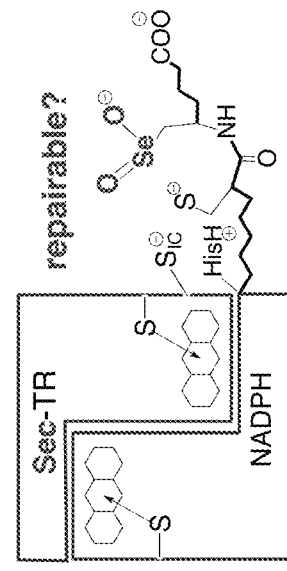
FIG. 13
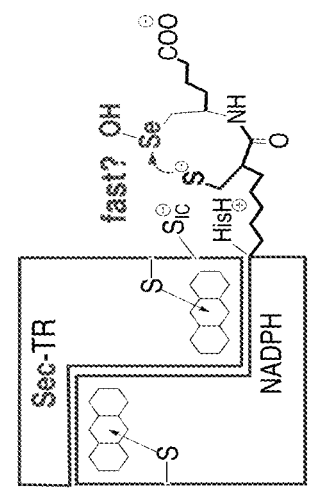

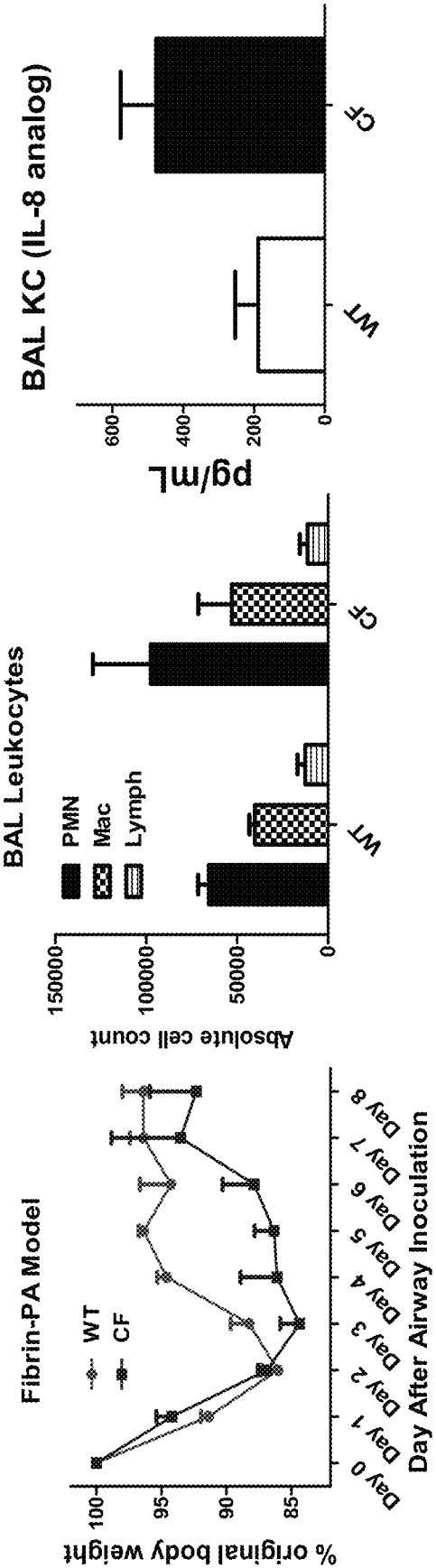
FIG. 20A
FIG. 20B
FIG. 20C
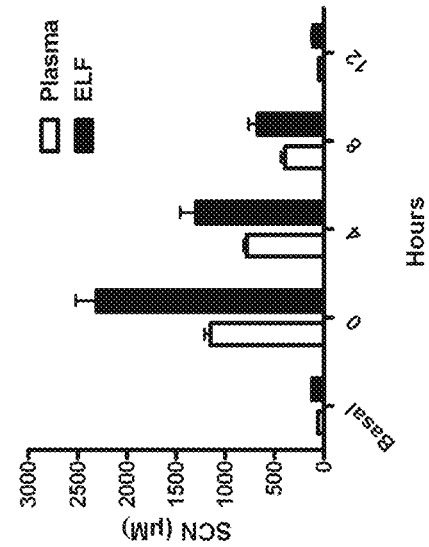
FIG. 21

FIG. 31A Burkholderia cepacia complex (BBC) isolates
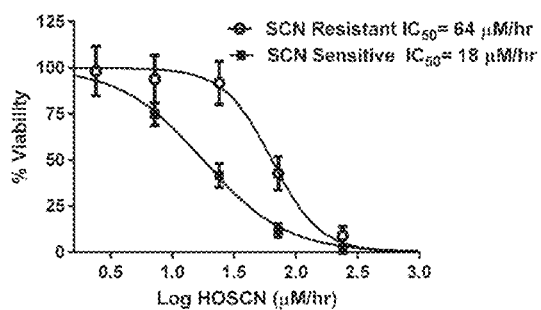
FIG. 31B Pseudomonas aeruginosa (PA) isolates
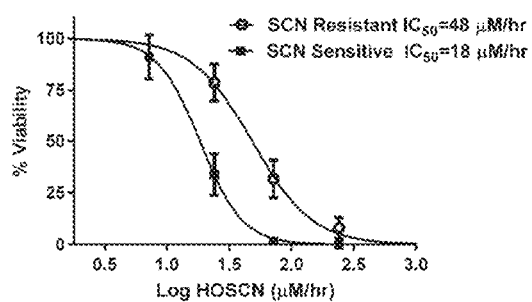
FIG. 31C Methicillin resistant Staphylococcus aureus (MRSA) isolates
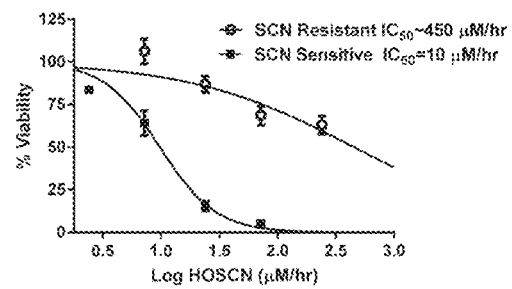

Fig. 32

METHODS AND COMPOSITIONS FOR TREATING INFECTION AND INFLAMMATION WITH SELENOCYANATE

CROSS-REFERENCE TO RELATED APPLICATIONS

This application is a continuation application of U.S. application Ser. No. 16/933,191, filed Jul. 20, 2020, now U.S. Pat. No. 11,351,141, which is a divisional application of U.S. application Ser. No. 16/116,409, filed Aug. 29, 2018, now U.S. Pat. No. 10,751,315, which claims the benefit of priority under 35 U.S.C. § 119(e) from U.S. Provisional Application No. 62/551,615, filed Aug. 29, 2018, the entire disclosure of each is hereby incorporated by reference.

FIELD OF THE INVENTION

The present invention generally relates to methods for treating infections and inflammation of the airway with a composition comprising selenocyanate, hyposelenocyanite, selenocyante conjugate or as a salt thereof.

BACKGROUND OF THE INVENTION

Mucosal surfaces throughout the body allow access to the external environment and present the opportunity for infection. A key part of the innate immune system is to prevent pathogen infection while limiting damage due to inflammation and oxidative stress. The paradox presented is how can one generate a reactive species that will damage a broad range of pathogens without harming self. To fulfill this paradox, a new paradigm on how the innate immune system uses thiocyanate ($^-$SCN) as a precursor to generate hypothiocyanite (HOSCN), a broad-spectrum biocide that can be selectively metabolized by the host, is disclosed herein. The pseudohalides such as thiocyanate ($^-$SCN) or selenocyanate ($^-$SeCN) can directly react with neutrophil generated hypohalous acid such as hypochlorite (HOCl) to form hypothiocyanite/hyposelenocyanite (HOSCN/HOSeCN) (Thomas, E. L., and Fishman, M. (1986) Oxidation of chloride and thiocyanate by isolated leukocytes. *J Biol Chem* 261, 9694-9702) or can substitute for a halide like chloride as a preferred substrate for haloperoxidases such as myeloperoxidase (MPO) to form HOSCN/HOSeCN (van Dalen, C. J., et al. (1997) Thiocyanate and chloride as competing substrates for myeloperoxidase. *Biochem J* 327 (Pt 2), 487-492). Evolutionary divergence found in mammalian thioredoxin reductase (TrxR) supports the selective detoxification of HOSCN/HOSeCN through the incorporation of selenocysteine containing thioredoxin reductase (Sec-TrxR) that resists oxidative inactivation seen with cysteine containing thioredoxin reductases (Cys-TrxR) found in pathogenic bacteria (Hirt, R. P., et al. (2002) The diversity and evolution of thioredoxin reductase: new perspectives. *Trends Parasitol* 18, 302-308).

$^-$SCN is obtained from the diet (Chandler, J. D., and Day, B. J. (2012) Thiocyanate: a potentially useful therapeutic agent with host defense and antioxidant properties. *Biochem Pharmacol* 84, 1381-1387) or formed as part of the detoxification of cyanide by sulfur transferases such as rhodanese (Maduh, E. U., and Baskin, S. I. (1994) Protein kinase C modulation of rhodanese-catalyzed conversion of cyanide to thiocyanate. *Res Commun Mol Pathol Pharmacol* 86, 155-173). $^-$SCN can directly react with HOCl forming HOSCN (Thomas, E. L., and Fishman, M. (1986) Oxidation of chloride and thiocyanate by isolated leukocytes. *J Biol Chem* 261, 9694-9702). Both myeloperoxidase (MPO) and lactoperoxidase (LPO) can utilize $^-$SCN to form HOSCN (van Dalen, C. J., et al. (1997) Thiocyanate and chloride as competing substrates for myeloperoxidase. *Biochem J* 327 (Pt 2), 487-492). The inventors have also seen that such reactions also occur with $^-$SeCN that generate the antimicrobial agent hyposelenocyanite (HOSeCN).

Cystic fibrosis is a genetic disorder due to mutation and loss of function associated with the cystic fibrosis transmembrane conductance regulator (CFTR) protein (Riordan J R, et al. 1989. Identification of the cystic fibrosis gene: cloning and characterization of complementary DNA. Science 245:1066-1073.). Cystic fibrosis is characterized by persistent lung infection with common bacteria including *Pseudomonas aeruginosa* (PA), *Burkholderia cepacia* complex (BCC), and methicillin-resistant *Staphylococcus aureus* (MRSA) (Lyczak J B, et al. 2002. Lung infections associated with cystic fibrosis. Clin Microbiol Rev 15:194-222). These pathogens frequently develop broad antibiotic resistance over the course of clinical care. The direct role for the mutant CFTR protein in the impairment of lung innate immunity is not known. CFTR protein regulates anion transport across apical epithelial cells (Quinton P M. 1983. Chloride impermeability in cystic fibrosis. Nature 301:421-422; Fragoso M A, et al. 2004. Transcellular thiocyanate transport by human airway epithelia. J Physiol 561:183-194; Tang L, et al. 2009. Mechanism of direct bicarbonate transport by the CFTR anion channel. J Cyst Fibros 8:115-121; Linsdell P, Hanrahan J W. 1998. Glutathione permeability of CFTR. Am J Physiol 275:C323-326). Among the endogenous anions that passivate through the CFTR channel are halides and pseudohalide such as chloride and thiocyanate ($^-$SCN).

$^-$SCN correlates with better lung function in patients with cystic fibrosis (Lorentzen D, et al 2011. Concentration of the antibacterial precursor thiocyanate in cystic fibrosis airway secretions. Free Radic Biol Med 50:1144-1150). $^-$SCN is concentrated up to mM amounts in secretions (e.g. saliva (Schultz C P, et al. 1996. Thiocyanate levels in human saliva: quantitation by Fourier transform infrared spectroscopy. Anal Biochem 240:7-12), nasal (Lorentzen D, et al 2011) and bronchoalveolar lining fluid (Gerson C, et al. 2000. The lactoperoxidase system functions in bacterial clearance of airways. Am J Respir Cell Mol Biol 22:665-671)). The CFTR protein is an important transporter of $^-$SCN, which has been demonstrated to be decreased in apical secretions from CF airway epithelial cells (Fragoso M A, et al. 2004. Transcellular thiocyanate transport by human airway epithelia. J Physiol 561:183-194), CF animal model secretions (Gould N S, et al. 2010. Hypertonic saline increases lung epithelial lining fluid glutathione and thiocyanate: two protective CFTR-dependent thiols against oxidative injury. Respir Res 11:119), and human CF saliva (Minarowski L, et al. 2008. Thiocyanate concentration in saliva of cystic fibrosis patients. Folia Histochem Cytobiol 46:245-246). $^-$SCN is oxidized to HOSCN by haloperoxidases (e.g., myeloperoxidase (MPO), lactoperoxidase (LPO)) (Klebanoff S J, et al. 1966. The peroxidase-thiocyanate-hydrogen peroxide antimicrobial system. Biochim Biophys Acta 117: 63-72). HOSCN is a selective oxidant preferring low $pK_a$ thiols and selenols (RSH and RSeH) (Skaff O, et al. 2012. Selenium-containing amino acids are targets for myeloperoxidase-derived hypothiocyanous acid: determination of absolute rate constants and implications for biological damage. Biochem J 441:305-316) and is used by the immune system to kill bacteria (Thomas E L, et al. 1994. Antibacterial activity of hydrogen peroxide and the lactoperoxidase-hydrogen peroxide-thiocyanate system against oral streptococci. Infect Immun 62:529-535), fungus (Majerus P M, Courtois P A. 1992. Susceptibility of *Candida albicans* to peroxidase-catalyzed oxidation products of thiocyanate, iodide and bromide. J Biol Buccale 20:241-245) and viruses (Mikola H, et al. 1995. Inhibition of herpes simplex virus type 1, respiratory syncytial virus and echovirus type 11 by peroxidase-generated hypothiocyanite. Antiviral Res 26:161-171; Pourtois M, et al. 1990. Inhibition of HIV infectivity by lactoperoxidase-produced hypothiocyanite. J Biol Buccale 18:251-253). The inventors have previously shown that mammalian selenocysteine-containing TrxR (Sec-TrxR), which contains a selenocysteine, can metabolize HOSCN in human lung epithelia (Chandler J D, et al. 2013. Selective metabolism of hypothiocyanous acid by mammalian thioredoxin reductase promotes lung innate immunity and antioxidant defense. J Biol Chem 288:18421-18428). The bacterial form of TrxR lacks selenocysteine and cannot metabolize HOSCN and instead is inactivated by HOSCN (Chandler J D, et al. 2013. Selective metabolism of hypothiocyanous acid by mammalian thioredoxin reductase promotes lung innate immunity and antioxidant defense. J Biol Chem 288:18421-18428).

Selenocyanate ($^-$SeCN) is a chemical analog of endogenous $^-$SCN. Substitution of selenium for sulfur in a compound usually results in a more reactive compound (Caldwell K A, Tappel A L. 1964. Reactions of Seleno- and Sulfoamino Acids with Hydroperoxides. Biochemistry 3:1643-1647). The inventors believe that $^-$SeCN is treated by the body in a similar manner as $^-$SCN and will be converted by haloperoxidases to a more potent antimicrobial oxidant, hyposelenocyanite (HOSeCN) while keeping its ability to be selectively detoxified by the host selenocysteine containing TrxR.

There is significant mortality and morbidity from pulmonary infections in many chronic lung disease most notability occurring in CF. The hallmark of CF is a dysregulation of lung inflammation and compromised ability to resolve infection and inflammation (Cantin, A. (1995) Cystic fibrosis lung inflammation: early, sustained, and severe. *Am J Respir Crit Care Med* 151, 939-941). As disclosed herein the inventors demonstrate that impaired transport and utilization of $^-$SCN disrupts the ratio of hypothiocyanite (HOSCN)/hypochlorite (HOCl) and sets up for the spiraling cycle of infection, chronic inflammation, and oxidative stress that are the major drivers of CF lung disease. As disclosed herein, the characterization of a novel selective detoxification pathway in lung host defense is undertaken. In addition, a better understanding of the importance and linkage between host defense and excessive lung inflammation is determined; the importance of $^-$SCN/HOSCN in pulmonary bacterial host defense and airway inflammation is assessed; and development of a novel therapeutic selenocyanate ($^-$SeCN) to treat infectious lung disease by promoting antimicrobial defense and suppressing inflammation is shown.

SUMMARY OF THE INVENTION

One embodiment of the invention relates to a method treating a disease comprising administering to a subject in need thereof, an effective amount of a composition comprising selenocyanate, hyposelenocyanite or a selenocyanate conjugate. In one aspect, the disease is a pulmonary disease. In one aspect, the pulmonary disease is selected from the group consisting of cystic fibrosis, pneumonia, viral pulmonary infection, bacterial pulmonary infection, fungal pulmonary infection, acute respiratory distress syndrome, asthma, chronic obstructive pulmonary disease (COPD), interstitial lung disease, bronchiectasis, sarcoidosis, idiopathic pulmonary fibrosis, bronchopulmonary dysplasia, rhinitis, and sinusitis. In another aspect, the disease is a result of or caused by a bacterial infection, a viral infection of a fungal infection. In still another aspect, the disease is an ocular disease selected from the group consisting of a viral eye infection, bacterial eye infection, fungal eye infection, dry eye, and uveitis.

In yet another aspect, the disease is a skin disease selected from the group consisting of a viral skin infection, bacterial skin infection, fungal skin infection, atopic dermatitis, skin wound, and eczema.

Another embodiment of the invention relates to a method of inhibiting microbial, fungal or viral growth in an airway of a subject, comprising administering to the airway of the subject an effective amount of a composition comprising selenocyanate, hyposelenocyanite or a selenocyanate conjugate.

Another embodiment of the invention relates to a method of inhibiting inflammation in an airway of a subject comprising administering to the airway of the subject an effective amount of a composition comprising selenocyanate, hyposelenocyanite or a selenocyanate conjugate. In one aspect, the subject is further administered an anti-inflammatory agent.

Another embodiment of the invention relates to a pharmaceutical composition comprising selenocyanate, hyposelenocyanite or a selenocyanate conjugate. In one aspect, the selenocyanate conjugate is attached by a bond with a thiol or selenol group.

In one aspect of any one of the embodiments of the invention, the composition is administered to the subject by an administration route selected from the group consisting of orally, nasally, parenterally (e.g., intravenously, intraperitoneally, subcutaneously, intramuscularly or intraarticularly), transdermally, intraocularly, topically (including buccally and sublingually), drops (such as eye or nose drops) and inhalation.

In one aspect of any one of the embodiments of the invention, the subject is further administered an antibiotic, an anti-fungal agent, an antiviral agent, anti-inflammatory agent or combinations thereof.

In one aspect of any one of the embodiments of the invention, the antibiotic is selected from the group consisting of aminoglycosides, ansamycins, penicillins and combinations thereof, first to fifth generation cepalosporins, glycopeptides, lincosamides, lipopeptide, macrolids, monobactams, nitrofurans, oxazolidinones, sulfonamides, tetracyclines, quinolones, fluroquinolones and polypeptides thereof.

In one aspect of any one of the embodiments of the invention, the antifungal agent is selected from the group consisting of polyene antimycotic, imidazoles, triazoles, thiazoles, allyamines, echinocandies and combinations thereof.

In another aspect of any one of the embodiments of the invention, the antiviral agent is selected from the group consisting of adamantines, chemokine receptor antagonists, integrase strand transfer inhibitors, neuraminidase inhibitors, non-nucleoside reverse transcriptase inhibitors (NNRTIs), nonstructural protein 5A (NS5A) inhibitors, nucleoside reverse transcriptase inhibitors (NRTIs), protease inhibitors, purine nucleosides and combinations thereof.

In one aspect of any one of the embodiments of the invention, the anti-inflammatory agent is selected from the group consisting of nonsteroidal anti-inflammatories (NSAIDS), resolvins, glucocorticoids, neutralizing antibodies of cytokines and chemokines and soluble receptor classes, antihistamines, protease inhibitors, and combinations thereof.

In still another aspect of any one of the embodiments of the invention, the composition is in a form selected from the group consisting aerosol, liquid, drops, spray, solid, lotion, gel and powder.

In another aspect of any one of the embodiments of the invention, pharmaceutically acceptable salts of selenocyanate, hyposelenocyanite and/or selenocyanate conjugate are used.

BRIEF DESCRIPTION OF THE DRAWINGS

(FIG. 4A) Human bronchiolar lung cells (16HBE) or (FIG. 4B) *Pseudomonas aeruginosa* (PA01) were treated for 2 hrs with glucose oxidase (GOX) system (generates $H_2O_2$), enzyme alone (MPO or LPO), or full system (enzyme+GOX), or full system with 40004 SCN. Viability was assessed 24 hrs later by lactate dehydrogenase release for lung cells or determination of colony forming units (CFUs) for bacteria.

(FIG. 5A) Intra- and extracellular SCN levels in cftr sufficient (C38) or deficient (IB3) epithelial cells. (FIG. 5B) Cftr sufficient and deficient cells treated with HOCl.

FIG. 12. Kinetic analysis of HOSeCN metabolism by recombinant mouse Sec-TrxR2 and recombinant *E. coli* Cys-TrxR. Mammalian Sec-TrxR can readily metabolize HOSeCN with a $K_m$ of 24 mM whereas there was no measurable activity using similar conditions with the *E. coli* form of Cys-TrxR.

FIG. 13: Sec-TrxR may resist oxidative inactivation due to fast resolution of Sec-SeOH by a resolving Cys residue such that overoxidation to Sec-SeO$_2^-$ is avoided (left panel/side of FIG. 13). Alternatively Sec can be oxidized to Sec-SeO$_2^-$, which is potentially repairable by rapid reduction by internal Cys thiols of TrxR such that b-elimination to form dehydroalanine (DHA) is avoided (right panel/side of FIG. 13). Sec-SeO$_2^-$ is capable of being reduced, unlike Cys-SO$_2^-$, which cannot be.

FIGS. 20A-20C. Increased sensitivity of $CF^{-/-}$ mice in a persistent fibrin PA lung infection model. Wild type (WT) and CF KO mice were infected with PA ($1\times10^7$ cfu/mouse) in a fibrin clot on Day 0. Subsets of mice were sacrificed at 72 hrs. BAL differential cell count, and the IL-8 analog, KC were assessed. (FIG. 20A) CF KO mice had greater weight loss and delayed recovery from Day 3-8 following fibrin-PA challenge. (FIG. 20B) CF KO mice had greater absolute neutrophil counts in the BAL fluid at 72 hours after fibrin-PA inoculation. (FIG. 20C) CF KO mice have higher concentrations of the neutrophil chemokine KC at 72 hours.

FIG. 21. Inhaled $^-$SCN is well tolerated and produces high ELF $^-$SCN levels in mice. Mice (C57B6) were exposed to an aerosolized isotonic 0.5% (w/v) $^-$SCN solution in PBS for 30 minutes (0 hr) and $^-$SCN levels in the ELF and serum were determined by HPLC-EC at various time points.

FIG. 24A specifically shows a clinical isolate of *M. abscessus* was exposed to the listed components next to the graph (GOX, LPO or SeCN; + indicates exposed to that component; − indicates not exposed to that component) and then plated on LB agar immediately after mixing. FIG. 24B shows a *Burkholderia cepacian* clinical isolate was exposed to 1000 mU/mL LPO and either KCL or KSeCn and plated on LB agar both immediately after mixing (0 hr first bar graph in each grouping) and after 1 hour incubation at 37 C (1 Hour second bar graph in each grouping). All conditions with GOX also contained dextrose, the required substrate of GOX for $H_2O_2$ production.

FIG. 25A shows [LPO] was varied in the presence of 1 mM —SeCN. FIG. 25B shows [—SeCN] was varied in the presence of 1600 mU/mL LPO. All samples were plated on LB immediately after mixing. CF0271-0636 and the ATCC strains were MABSC subspecies *abscessus* and CF0008-6241 was subspecies *massiliense*.

FIG. 27A in PBS; FIG. 27B in Middlebrook 7H9; FIG. 27C in Lysogeny Broth.

FIGS. 31A-31C show Hypothiocyanite (HOSCN) resistance in CF relevant bacterial isolates. Comparison of a HOSCN resistant (open circles) and sensitive (closed squares) (FIG. 31A) BCC clinical isolates, (FIG. 31B) PA clinical isolates, and (FIG. 31C) MRSA clinical isolates. Bacteria cell viability assessed 24 hours after a 2 hour exposure to HOSCN generating system and viability assessed by CFUs.

FIG. 32 shows inhaled SeCN is well tolerated and produces high ELF SeCN levels in mice Mice (C57B6) were exposed to an aerosolized isotonic 0.05% (w/v) SeCN solution in PBS for 30 minutes (0 hr) and SeCN levels in the ELF and serum were determined by HPLC-EC at various time points.

DETAILED DESCRIPTION OF THE INVENTION

This invention generally relates to methods and/or uses for treating a disease or condition with selenocyanate, hyposelenocyanite, a selenocyanate conjugate and/or a pharmaceutically acceptable salt thereof, as well as, to compositions comprising selenocyanate, hyposelenocyanite, a selenocyanate conjugate and/or a pharmaceutically acceptable salt thereof.

The concept of selective detoxification of HOSCN by mammalian Sec-TrxR, which allows the lung to defend against pathogens without harming self is transformational in the treatment of CF, lung inflammation, and inflammation in general. Other innovations disclosed herein include a mechanism by which a large group of oxidants generated during inflammation are converted by SCN/SeCN to HOSCN/HOSeCN for detoxification by the host; novel targeting of prokaryotic, Cys-TrxR by HOSCN or HOSeCN and their roles in bactericidal effects, $^-$SCN/$^-$SeCN improves neutrophil and macrophage host defense functions, and $^-$SeCN therapy.

Figure 1:
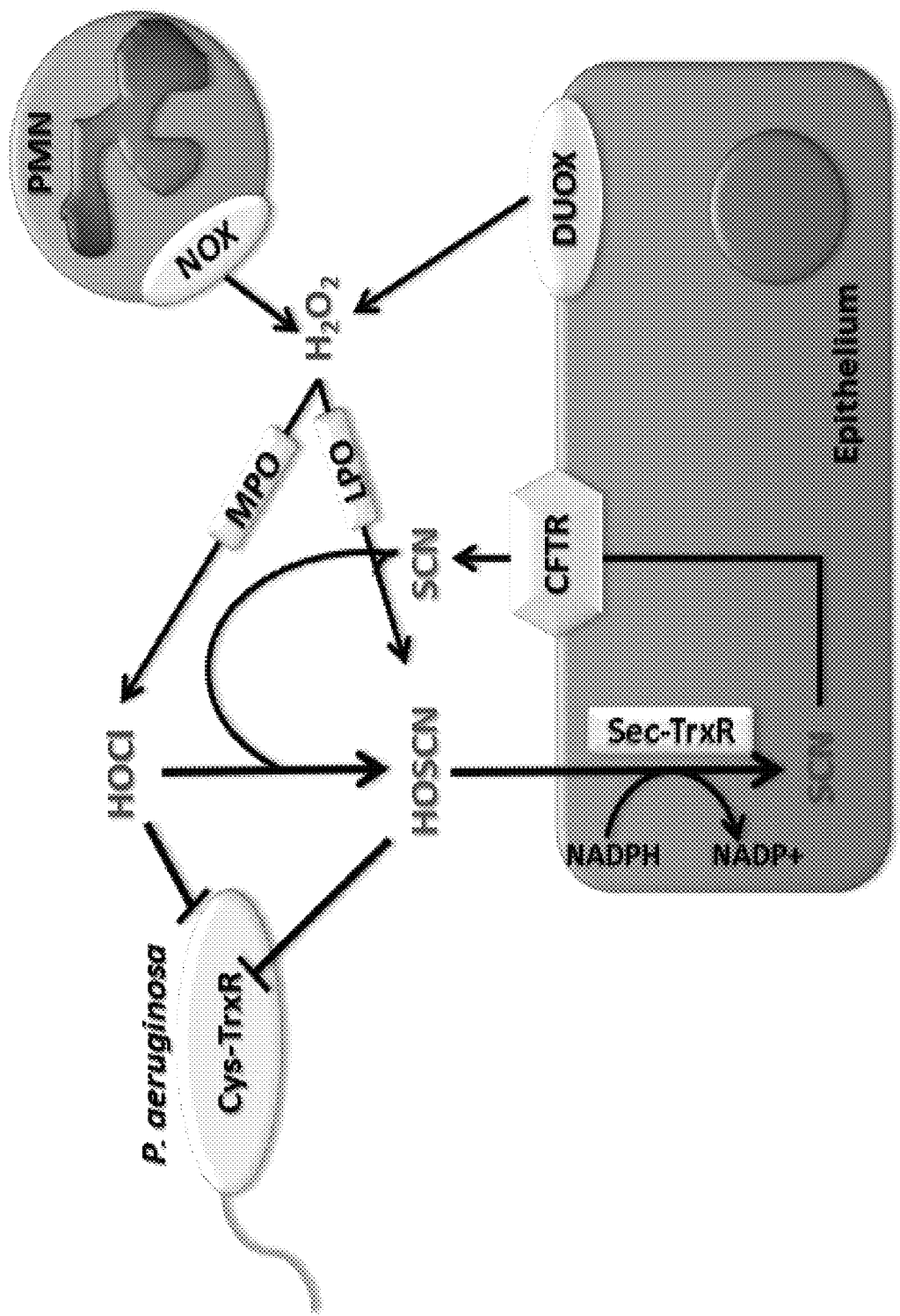
FIG. 1. Selective detoxification of hypothiocyanite (HOSCN) by lung epithelium. Both MPO and LPO can generate HOSCN from $H_2O_2$ released by neutrophil (PMN) NADPH oxidase (NOX) or epithelial duel oxidase (DUOX). Hypochlorite (HOCl) generated from MPO can also be directly converted to HOSCN by reaction with SCN. HOSCN can be readily detoxified and recycled back to $^-$SCN by mammalian epithelial and PMN thioredoxin reductase (Sec-TrxR) but not by prokaryotic Cys-TrxR found in *P. aeruginosa* (PA). Recycled $^-$SCN is transported back through CFTR into the airway fluid.
Figure 2:
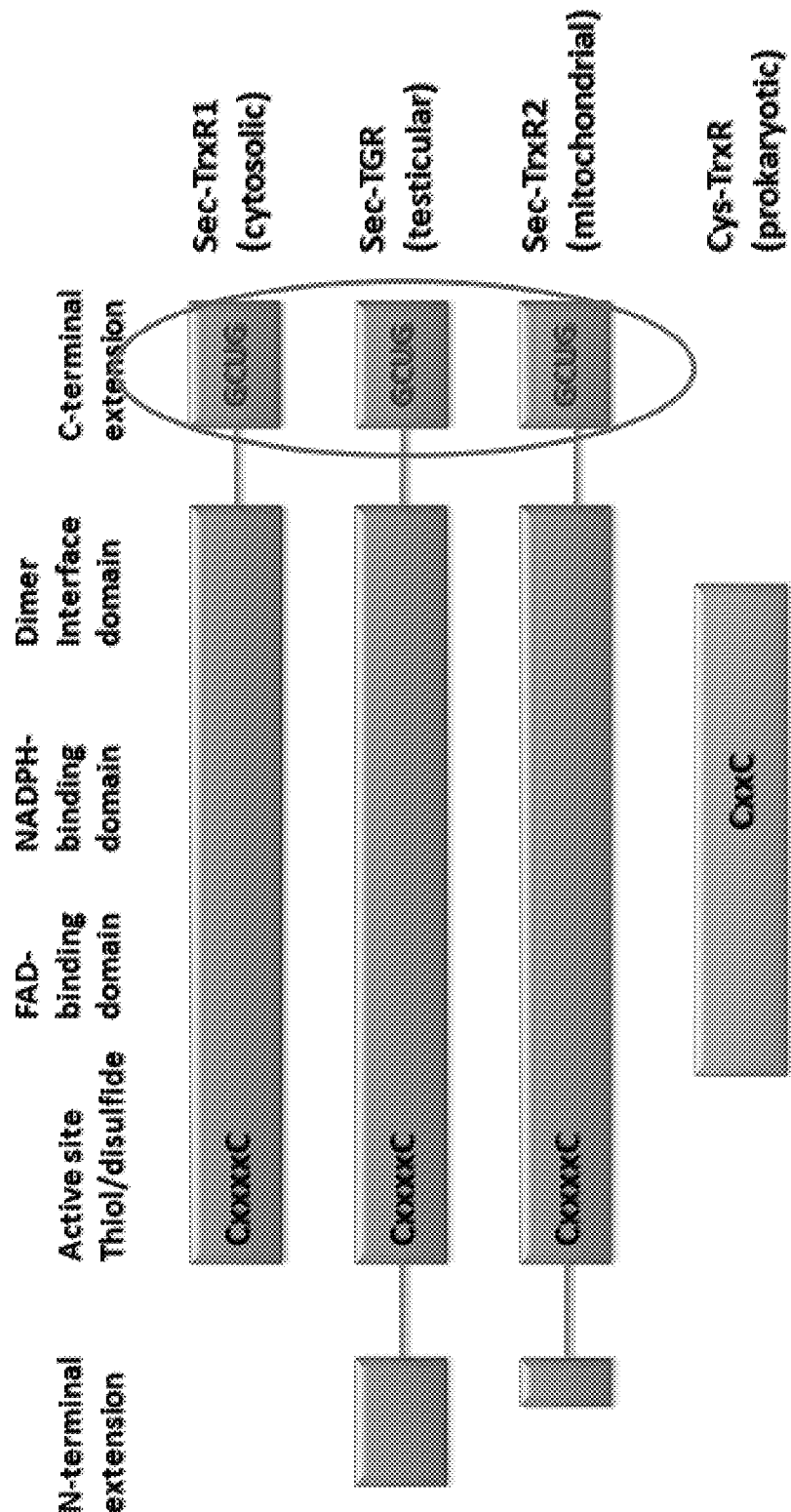
FIG. 2. Evolutionary diversity of thioredoxin reductases (TrxR) amongst mammalian isoforms (Sec-TrxR1, TrxR2 & thioredoxin-glutathione reductase (TGR)) and Cys-TrxR prokaryotic form. Notice the lack of C-terminal selenocysteine motif (GCUG) and different location of the active site thiol/disulfide catalytic centers between mammalian Sec-TrxRs and the prokaryotic form Cys-TrxR.
Figure 3B:
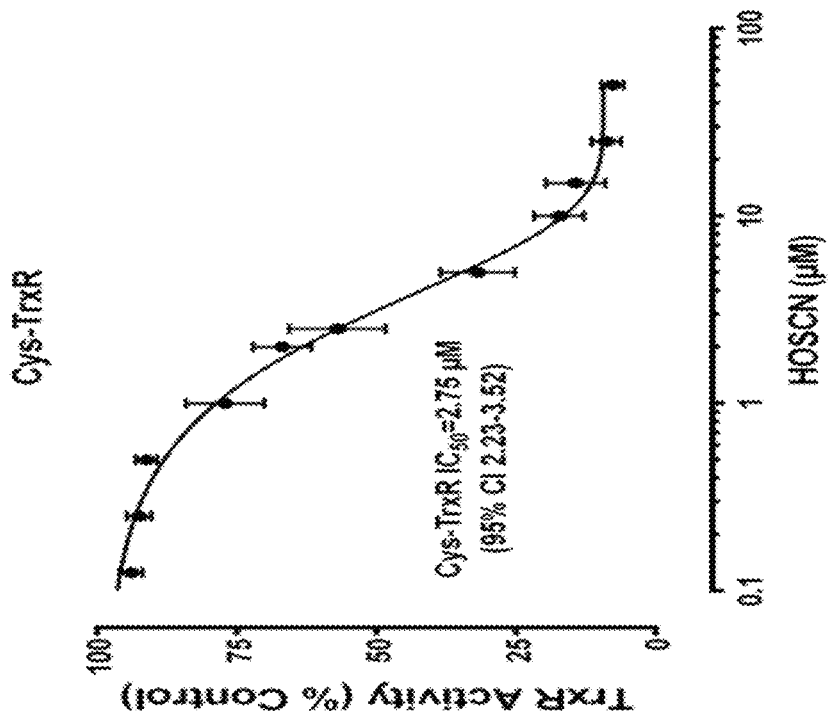
FIGS. 3A-3B. Kinetic analysis of HOSCN metabolism by recombinant mouse Sec-TrxR and recombinant *E. coli* Cys-TrxR. Mammalian Sec-TrxR can readily metabolize HOSCN (FIG. 3A) with a Km of 30 µM whereas there was no measurable activity using similar conditions with the *E. coli* form of Cys-TrxR. Sec-TrxR forms that lack a selenocysteine (Sec489Cys) or truncated by the last 8 amino acids (D8) had diminished activity. In contrast, the Cys-TrxR form was inhibited by HOSCN with an $IC_{50}$ of 2.75 µM (FIG. 3B).
Figure 3A:
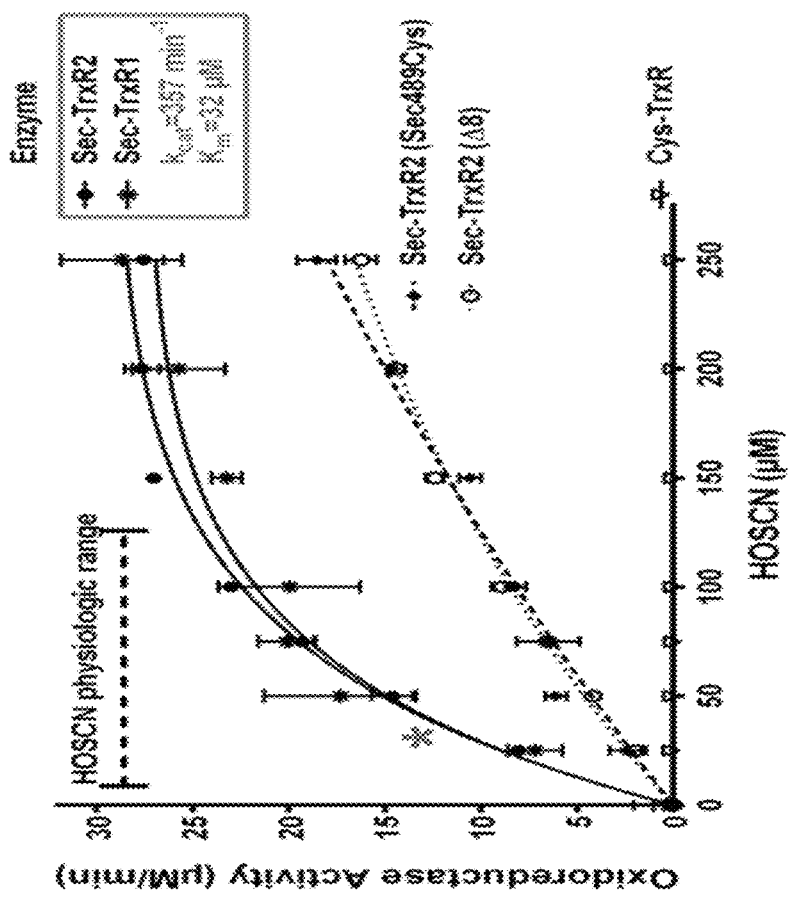

There are 3 known mammalian thioredoxin reductases (TrxRs) that have a catalytically active selenocysteine (Sec) residue in the C-terminal domain which is lacking in prokaryotes (FIG. 2). Sec-TrxR forms active head to tail homodimers that places the C-terminal selenocysteine in close proximity to the N-terminal active site. It is interesting to note that there is an apparent exclusivity of the mammalian and the prokaryote forms of TrxR where no genomes have been shown to express both forms suggesting that the two forms evolved independently (Hirt, R. P., et al. (2002) The diversity and evolution of thioredoxin reductase: new perspectives. *Trends Parasitol* 18, 302-308). The inventors have discovered that mammalian selenocysteine thioredoxin reductase (Sec-TrxR) can selectively detoxify HOSCN and that this activity is unique to the mammalian form of Sec-TrxR and is lacking in prokaryotes Cys-TrxR which is oxidatively inactivated by HOSCN (FIG. 3) (Chandler, J. D., et al. (2013) Selective metabolism of hypothiocyanous acid by mammalian thioredoxin reductase promotes lung innate immunity and antioxidant defense. *J Biol Chem* 288, 18421-18428). The inventors have similar data with HOSeCN. (FIG. 12). This unique host defense system can suppress bacteria growth while sparing the host tissue. The $K_m$ for both HOSCN and its novel analog hyposelenocyanite (HOSeCN) is similar to that reported for thioredoxin (Trx) with Sec-TrxR (Amer, E. S., Zhong, L., and Holmgren, A. (1999) Preparation and assay of mammalian thioredoxin and thioredoxin reductase. *Methods Enzymol* 300, 226-239). The inventors have shown that LPO/SCN/HOSCN conditions that are bactericidal for *Pseudomonas aeruginosa* (PAO1) are not toxic to lung epithelial cells and suggest a selective detoxification pathway exists for both HOSCN and HOSeCN (FIG. 4) (Chandler, J. D., et al. (2013) Selective metabolism of hypothiocyanous acid by mammalian thioredoxin reductase promotes lung innate immunity and antioxidant defense. *J Biol Chem* 288, 18421-18428).

Figure 5A:
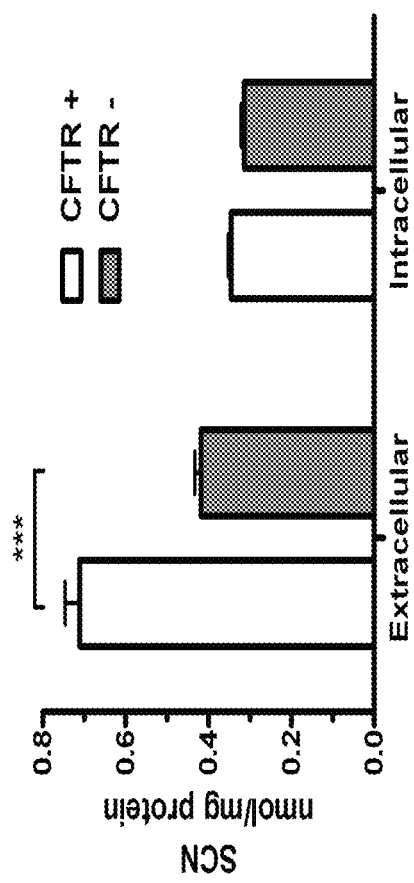
FIGS. 5A and 5B. Cftr deficiency sensitizes lung cells to HOCl injury.
Figure 5B:
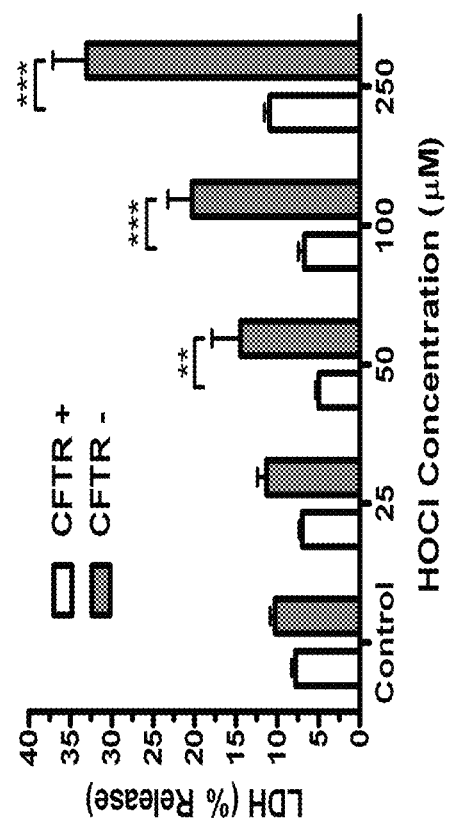
Figure 6:
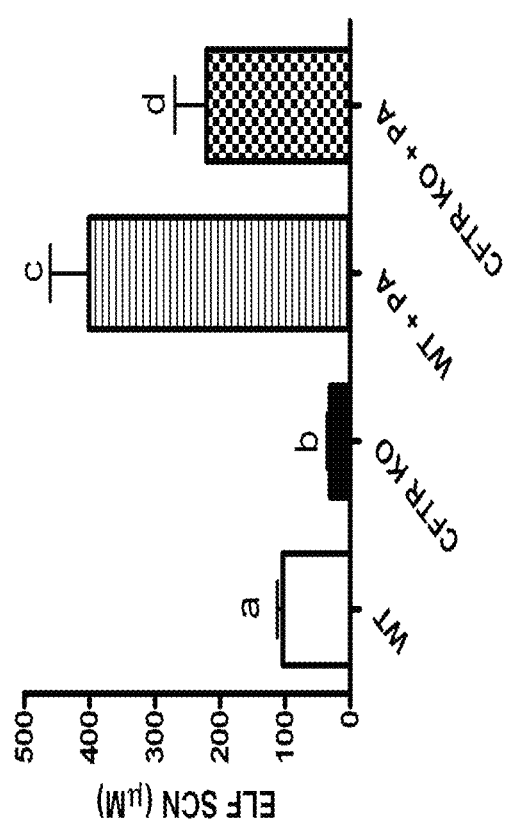
FIG. 6. PA lung infection increases airway fluid $^-$SCN levels in both wild type (WT) and CFTR knock-out (KO) mice. Mice were instilled with PA and lungs lavaged 72 hrs later.
Figures 7A, 7B:
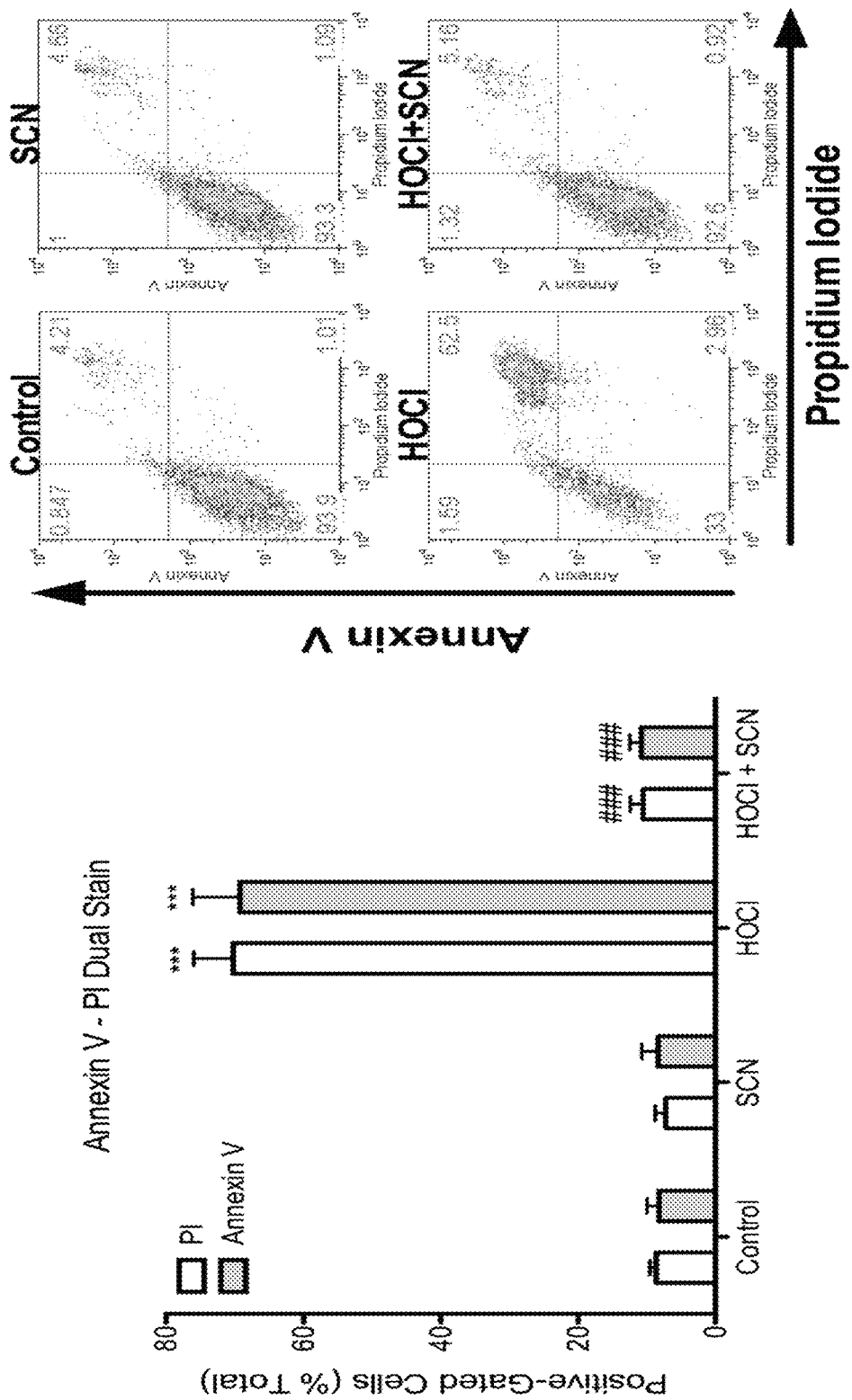
FIGS. 7A-7B. —SCN protects macrophage (J774A.1.) cells from HOCl-mediated necrosis. Cells were exposed to 100 µM HOCl and/or 400 µM $^-$SCN in PBS for 15 minutes, washed and then placed in fresh media for 6 hrs before viability assessment with flow cytometry (FIG. 7A). The % of Annexin V (apoptosis marker) and propidium iodide (PI) positive cells in each gate. Representative images of gated cells are shown in FIG. 7B.

Current dogma suggests that $^-$SCN is obtained from the diet; however studies by the inventors suggest that lung epithelial cells can make and concentrate extracellular $^-$SCN without identifiable $^-$SCN in the growth media and is protective against HOCl (FIG. 5) (Gould, N. S., et al. (2010) Hypertonic saline increases lung epithelial lining fluid glutathione and thiocyanate: two protective CFTR-dependent thiols against oxidative injury. *Respir Res* 11, 119). Recently, there have been reports in the literature that human CF $^-$SCN levels in nasal fluid (Lorentzen, D., et al. (2011) Concentration of the antibacterial precursor thiocyanate in cystic fibrosis airway secretions. *Free Radic Biol Med* 50, 1144-1150) and bronchoalveolar lavage fluid (BALF) (Thomson, E., et al. (2010) Identifying peroxidases and their oxidants in the early pathology of cystic fibrosis. *Free Radic Biol Med* 49, 1354-1360) can not differ from controls. This discrepancy may be due to the fact that the human controls used for the comparison group did not have an active airway PA infection, which would have increased the $^-$SCN levels in the control group. In fact, the comparison of epithelial lining fluid (ELF) $^-$SCN between wild type and the CF$^{-/-}$ mice with the respective *Pseudomonas aeruginosa* (PA) infection would predict that CF subjects would actually have higher ELF $^-$SCN levels due to adaptive responses in a mouse model (FIG. 6). Data generated by the inventors show dramatic early increases in ELF $^-$SCN levels in response to PA challenge, and this response is significantly greater with normal CFTR function (FIG. 6).

Figures 4A, 4B:
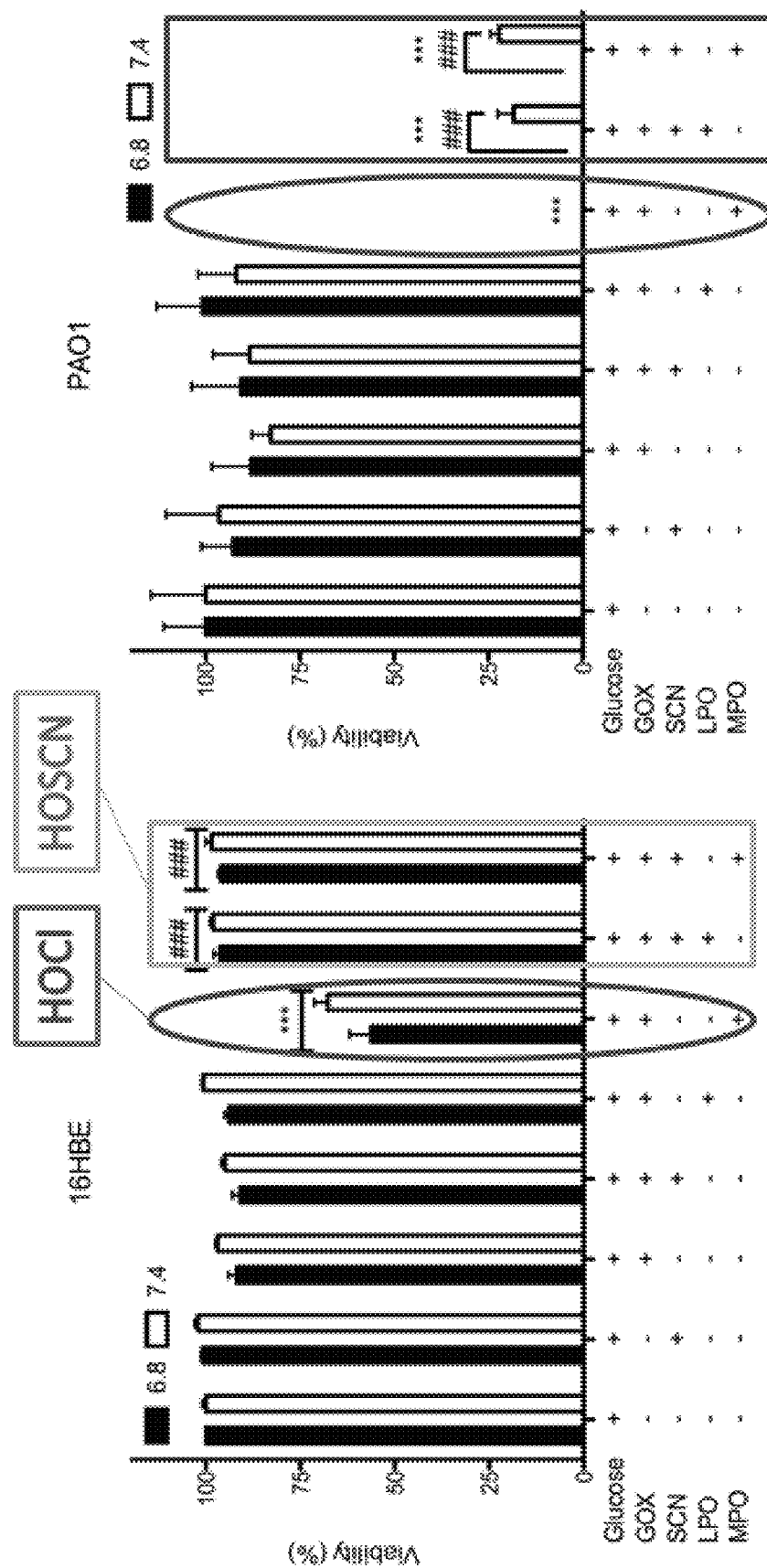
FIGS. 4A-4B. HOSCN generation spares host lung epithelial cells while killing bacteria. Studies were conducted under similar conditions that generated about 120 µM/hr of either HOCl or HOSCN.

Extracellular $^-$SCN regulates inflammation, immunity, and lung injury. There is very little known about how thiols are transported across membranes and much of the current understanding comes from studies in oncology on multidrug resistant proteins (MRP) (Leitner, H. M., et al. (2007) Harnessing drug resistance: using ABC transporter proteins to target cancer cells. *Biochem Pharmacol* 74, 1677-1685). In the lung, one of the few identified apical thiol transporters is the CF transmembrane conductance regulator (CFTR) protein which is in the MRP gene family and has been shown to transport $^-$SCN in vitro (Gould, N. S., et al. (2010) Hypertonic saline increases lung epithelial lining fluid glutathione and thiocyanate: two protective CFTR-dependent thiols against oxidative injury. *Respir Res* 11, 119; Linsdell, P. (2001) Thiocyanate as a probe of the cystic fibrosis transmembrane conductance regulator chloride channel pore. *Can J Physiol Pharmacol* 79, 573-579) and in vivo (Gould, N. S., et al. (2010)). Lactoperoxidase (LPO) comprises ~1% of the soluble protein in airway secretions (Conner, G. E., et al. (2007) The lactoperoxidase system links anion transport to host defense in cystic fibrosis. *FEBS Lett* 581, 271-278) and LPO utilizes $^-$SCN as a substrate to generate HOSCN that is an epithelial sparing biocide (FIG. 4). Airway LPO activity increases the rate of bacterial clearance from sheep airways (Conner, G. E., et al. (2007)) and recent studies have shown that CF subjects with higher nasal fluid $^-$SCN levels had better lung function than those with low $^-$SCN levels (Lorentzen, D., et al. (2011) Concentration of the antibacterial precursor thiocyanate in cystic fibrosis airway secretions. *Free Radic Biol Med* 50, 1144-1150). Myeloperoxidase (MPO) is a neutrophil and macrophage peroxidase that is released upon activation and generates HOCl, a potent broad-spectrum biocide. $^-$SCN and chloride are competing substrates for MPO (Arner, E. S., Zhong, L., and Holmgren, A. (1999) Preparation and assay of mammalian thioredoxin and thioredoxin reductase. *Methods Enzymol* 300, 226-239). ⁻SCN is cytoprotective against MPO and HOCl-mediated cytotoxicity (Chandler, J. D., et al. (2013) Selective metabolism of hypothiocyanous acid by mammalian thioredoxin reductase promotes lung innate immunity and antioxidant defense. *J Biol Chem* 288, 18421-18428; Chandler, J. D., et al. (2015) Antiinflammatory and Antimicrobial Effects of Thiocyanate in a Cystic Fibrosis Mouse Model. *Am J Respir Cell Mol Biol* 53, 193-205; Xu, Y., et al. (2009) The antioxidant role of thiocyanate in the pathogenesis of cystic fibrosis and other inflammation-related diseases. *Proc Natl Acad Sci USA* 106, 20515-20519) (FIGS. 4A, 4B and 7A and 7B). These data demonstrate that altered lung ELF ⁻SCN levels may contribute to lung disease by altering the ratio of HOCl/HOSCN due to impaired secretion of ⁻SCN through CFTR and result in more epithelial and macrophage damage, oxidative stress, and amplification of lung inflammation.

Inhaled SCN is protective in *Pseudomonas aeruginosa* (PA) lung infection models. The inventors have shown critical in vivo proof of principle with inhaled ⁻SCN in PA-infected mice (Chandler, J. D., et al. (2015); Chandler, J. D., et al. (2013) Nebulized thiocyanate improves lung infection outcomes in mice. *Br J Pharmacol* 169, 1166-1177). Mice were infected with mucoid CF PA isolate ($1 \times 10^7$ CFU/mouse) as described in the inventor's fibrin lung infection models and treated with nebulized ⁻SCN (0.5%, twice daily) started 1 day after infection and followed over 72 hours. ⁻SCN treated mice had less body weight loss, lower lung CFU PA burden, and decreased lung pyocyanin levels (Chandler, J. D., et al. (2013)). An important note about this data is that the nebulized ⁻SCN was started a full day after PA lung inoculation and there was a dramatic and rapid improvement in body weight that corresponded with a decrease in bacterial lung burden and neutrophil influx at 72 hours in the ⁻SCN treatment group. In addition, nebulized ⁻SCN dramatically suppressed markers of lung inflammation as noted by decreased bronchoalveolar lavage (BAL) levels of KC (IL-8 analog) and BAL neutrophil cell counts. This study illustrates the powerful effect and function of ⁻SCN in lung infection and the duel action of ⁻SCN having both host defense and antioxidant activities. Mice that overexpress a sodium channel, βENaC, have been developed that spontaneously develop lung inflammation and mucous obstructions similar to that reported in subjects with CF (Mall, M., et al. (2004) Increased airway epithelial Na+ absorption produces cystic fibrosis-like lung disease in mice. *Nat Med* 10, 487-493). This model is useful to differentiate the antimicrobial effect of an agent from its potential anti-inflammatory effects. The inventors have shown that nebulized SCN can decrease basal inflammation and oxidative stress as well inflammation and bacterial load associated with *Pseudomonas aeruginosa* lung infection (FIG. 8) (Chandler, J. D., et al. (2015)). These studies show that it is feasible to dramatically raise the lung ELF ⁻SCN levels by inhalation delivery and that nebulized ⁻SCN is well tolerated in mice and can decrease markers of morbidity in a CF model of PA lung infection.

Figure 9:
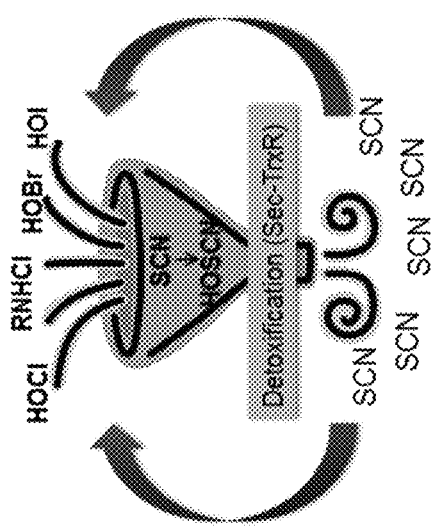
FIG. 9. Redirection of innate immunity derived oxidants by thiocyanate ($^-$SCN) to hypothiocyanite (HOSCN) and detoxication by Sec-TrxR.

Thiocyanate (⁻SCN) converts a large group of diverse oxidants to a single oxidant that can be detoxified by Sec-TrxR. An innovative concept presented herein is the way the body uses ⁻SCN to react with a broad range of innate immunity generated oxidants such as hypochlorite (HOCl), hypobromite (HOBr), hypoiodite (HOI), and chloramines (RNHCl) to form hypothiocyanite (HOSCN) that can be detoxified by the host but not the pathogen (FIG. 9).

Figure 10:
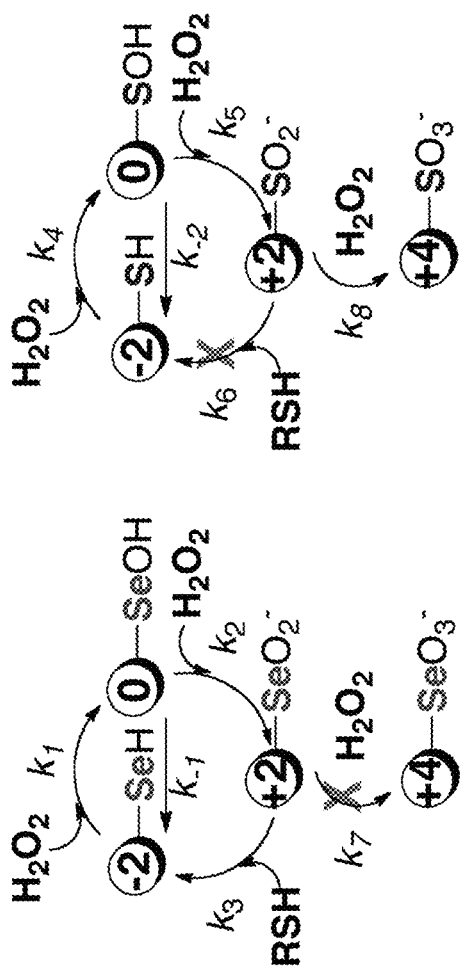
FIG. 10. Redox states of Sec and Cys. Both Se and S can be oxidized from −2 to 0 and restored back to 0. A large difference between the two occurs upon further oxidation to the +2 state. Reduction from +2 to −2 is very slow for S, but very FAST for Se. Conversely, oxidation from +2 to +4 is fast for S, but slow for Se.
Figure 11B:
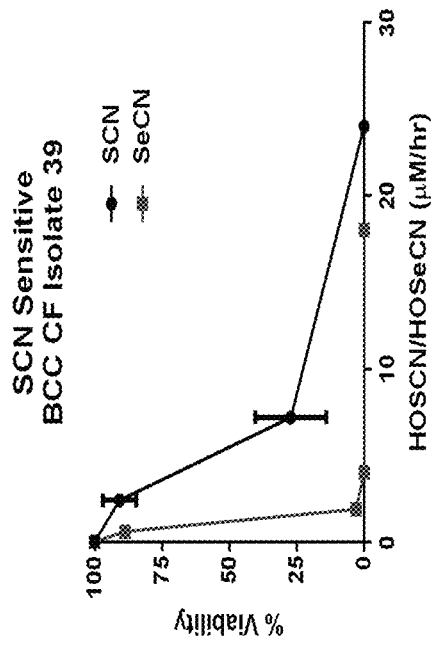
FIGS. 11A-11D. HOSeCN is a more potent antimicrobial agent than HOSCN. A lactoperoxidase (LPO) system was used to generate increasing fluxes of either HOSCN or HOSeCN in presence of 400 µM of either $^-$SCN or $^-$SeCN. LPO in the presence of a hydrogen peroxide generating system (glucose oxidase, GOX) can convert both thiocyanate and selenocyante to their respective hypopseudohalous acid species (HOSCN and HOSeCN) that are biocides. Common Cystic Fibrosis colonizing bacteria such as gram negative bacteria *Pseudomonas aeruginosa*, PAO1 (FIG. 11A), *Burkholderia cepacia* complex, BBC (FIG. 11B) and gram positive methicillin resistant *Staphylococcus aureus*, MRSA (FIGS. 11C & 11D) have decreased cell viability in the presence of either SCN (400 uM) or SeCN (400 uM) with host defense system (LPO+GOX). SeCN was as effective or superior in killing both thiocyanate susceptible and resistant bacteria. Bacterial inoculums ($10^6$ colony forming units, CFU) were incubated with host defense system for 2 hours at room temperature and bacteria were plated on LB agar plates and cell viability was determined by dilution and counting CFUs.
Figure 11D:
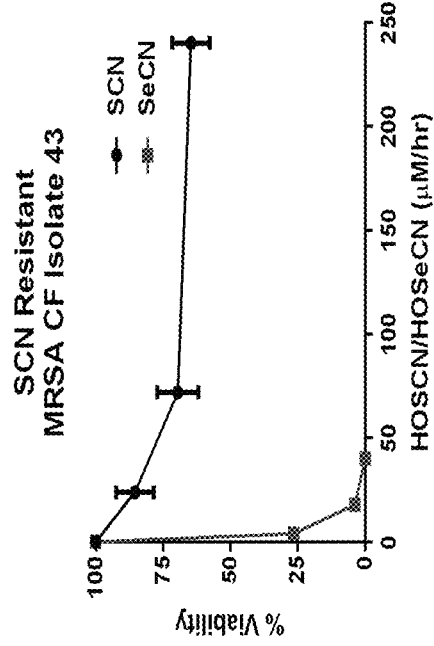
Figure 11A:
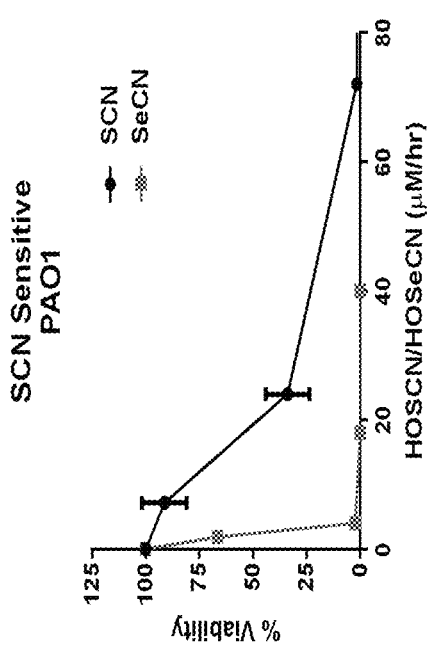
Figure 11C:
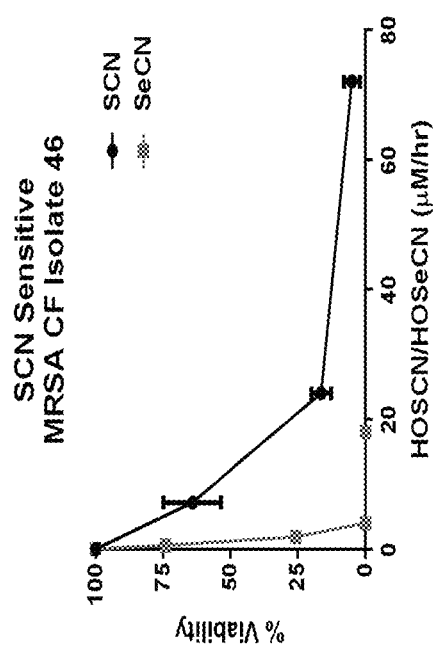

Why does HOSCN inactivate prokaryotic Cys-TrxR but not mammalian Sec-TrxR? The Janus-faces of ⁻SCN/HOSCN, high nucleophilicity and high electrophilicity, are shared by the selenol group of selenocysteine (Sec) found exclusively in higher eukaryote Sec-TrxR. A selenol is a good nucleophile that can attack the S of HOSCN and is utilized catalytically as proposed by the inventors for mammalian Sec-TrxR. The resulting Sec-SCN is now a very good electrophile that will be attacked by another thiol, producing ⁻SCN and a thioselenide. This Janus-faced property of Sec allows it to resist over oxidation to higher oxidation states that would result in inactivation of a Cys residue in a protein. Furthermore, even if Sec is over oxidized to Sec-SeO$_2^-$, this form can be reduced back to a selenol as has been shown experimentally in the case of selenosubtilisin (Kanzok, S. M., et al. (2001) Substitution of the thioredoxin system for glutathione reductase in *Drosophila melanogaster*. *Science* 291, 643-646). The same oxidation of Cys to Cys-SO$_2^-$ results in permanent inactivation due to an inability of Cys-SO$_2^-$ to be reduced back to Cys (FIG. 10).

The inventors have determined the surprising result that selenocyanate (⁻SeCN) is a novel and more potent analog of thiocyanate (⁻SCN). The selenium group adds activity to SeCN in much the same way as it does for Sec in TrxR. SeCN is a much better nucleophile than SCN which means it has faster rates of reaction with oxidants. HOSeCN is a stronger electrophile than HOSCN which means it is more potent at oxidizing sensitive cysteine groups in bacteria than HOSCN.

The inventors have determined, that ⁻SCN when used as a substrate for LPO or MPO can generate HOSCN at levels that do not affect human lung epithelial cell viability but kill several CF derived multi-drug resistant *Pseudomonas aeruginosa* (PA) mucoid isolates (Chandler, J. D., et al. (2013) Selective metabolism of hypothiocyanous acid by mammalian thioredoxin reductase promotes lung innate immunity and antioxidant defense. *J Biol Chem* 288, 18421-18428). The inventors have determined that SCN/LPO system is very effective at killing isolates of PA and *Burkholderia cepacia* complex (BCC) and ⁻SeCN/LPO was more potent than ⁻SCN/LPO (FIG. 11A and FIG. 11B and FIGS. 30A-30F). The inventor also has found some pathogenic bacteria harbor resistance to HOSCN killing (FIG. 31A-31C and Table 1). The inventors compared the ability of —SeCN/LPO to kill ⁻SCN/LPO sensitive and resistant CF derived *Burkholderia cepacian* complex (BCC), *Pseudomonas aerginosa* (PA), and methicillin-resistant *Staphylococcus aureus* (MRSA) isolates (FIG. 30A-30F). ⁻SeCN also shares many of the same biological attributes as SCN. For instance, the oxidant of ⁻SeCN, HOSeCN, is a substrate for mammalian Sec-TrxR and has a similar $K_m$ as reported for HOSCN (FIG. 12).

TABLE 1

| Bacterial sensitivity towards HOSCN killing | | |
|---|---|---|
| Bacterial Strains | HOSCN IC$_{50}$ (μM/hr)# | 95% CI (uM/hr) |
| *Burkholderia cepacia* complex (BCC) | | |
| B. dolsa* | 79 | 68-91 |
| B. cenocepacia* | 59 | 48-72 |
| B. vietnameisis | 64 | 45-91 |
| B. multivorans 41* | 18 | 14-23 |

TABLE 1-continued

Bacterial sensitivity towards HOSCN killing

| Bacterial Strains | HOSCN IC$_{50}$ (μM/hr)# | 95% CI (uM/hr) |
|---|---|---|
| *Pseudomonas aeruginosa* (PA) | | |
| AMT-9* | 5 | 3-7 |
| PA 39* | 5 | 4-7 |
| PAO1 | 18 | 14-24 |
| PA-X* | 13 | 9-18 |
| PA-T* | 48 | 34-68 |
| methicillin-resistant *Staphylococcus aureus* (MRSA) | | |
| MRSA 43* | 450 | 170-1260 |
| MRSA 44* | 260 | 140-490 |
| MRSA 45* | 24 | 19-30 |
| MRSA 46* | 10 | 8-12 |

*Isolates from CF sputum samples
HOSCN flux generated for 2 hours using a GOX/LPO/SCN system at pH 7.4

Selenocysteine (Sec, U) replaces a few dozen cysteine (Cys) residues out of the 214,000 Cys residues in the human proteome (Jones, D. P., and Go, Y. M. (2011) Mapping the cysteine proteome: analysis of redox-sensing thiols. *Curr Opin Chem Biol* 15, 103-112). Due to the high bioenergetic cost of Sec-insertion, Sec must impart chemical and biological properties to an enzyme that Cys lacks. Interestingly, Sec is not required for catalysis as Cys-orthologs catalyze identical enzymatic reactions with high efficiency (Kanzok, S. M., et al. (2001) Substitution of the thioredoxin system for glutathione reductase in *Drosophila melanogaster*. *Science* 291, 643-646). Sec confers resistance to irreversible inactivation by oxidation to an enzyme because the Se-oxide is a superior electrophile relative to a S-oxide and this means that Se-oxides are very rapidly reduced, enabling the enzyme to resist oxidative inactivation (Snider, G. W., et al. (2013) Selenocysteine confers resistance to inactivation by oxidation in thioredoxin reductase: comparison of selenium and sulfur enzymes. *Biochemistry* 52, 5472-5481). But which Se-oxide enables this great resistance to inactivation (FIG. 13), the Sec-SeOH or the Sec-SeO$_2^-$ form?

Figure 14:
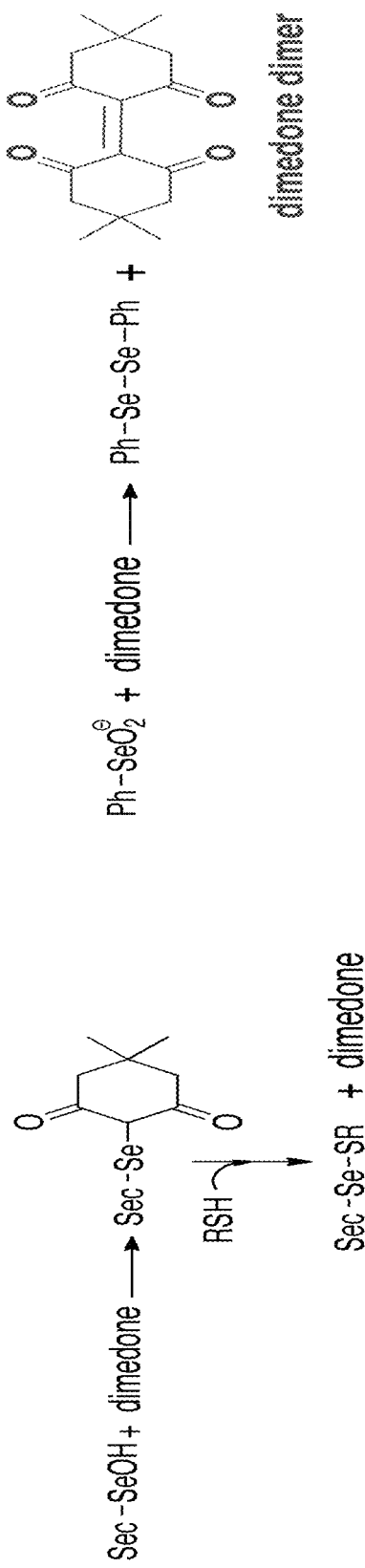
FIG. 14: Sec-SeOH reacts with dimedone to form an adduct, but this adduct is reversed by addition of thiol (left panel/side of FIG. 14). Ph-SeO$_2^-$ reacts with dimedone, but a stable adduct is not formed (right panel/side of FIG. 14). Instead the dimedone dimer is formed and this is a marker of seleninic acid formation that can be detected by mass spectrometry (MS).

Recently it has been shown that Sec-containing glutathione peroxidase (Gpx-1) resists overoxidation to Sec-SeO$_2^-$ by stabilizing the Sec-SeOH form. It is known that selenosubtilisin is capable of using Sec-SeO$_2^-$ during its redox cycle and there is an X-ray crystal structure of the enzyme in this form (Nelson, K. J., et al. (2010) Use of dimedone-based chemical probes for sulfenic acid detection methods to visualize and identify labeled proteins. *Methods Enzymol* 473, 95-115; Rhee, S. G., and Cho, C. S. (2010) Blot-based detection of dehydroalanine-containing glutathione peroxidase with the use of biotin-conjugated cysteamine. *Methods Enzymol* 474, 23-34; Li, F., et al. (2014) Glutathione peroxidase's reaction intermediate selenenic acid is stabilized by the protein microenvironment. *Free Radic Biol Med* 76, 127-135). Data by the inventors showed that they were unable to alkylate Sec-TrxR with dimedone, a common reagent used to alkylate sulfenic acid (Cys-SOH) residues, even when it was added in great excess (Snider, G., et al. (2010) Methaneseleninic acid is a substrate for truncated mammalian thioredoxin reductase: implications for the catalytic mechanism and redox signaling. *Biochemistry* 49, 10329-10338). The reason why has been determined. Studies by the inventors with model compounds show that alkylation of Sec by dimedone can be reversed by addition of thiol. In addition, dimedone can react with Sec-SeO$_2$, but a stable adduct is not formed. Instead the seleninic acid is reduced to a diselenide, with resulting formation of a dimedone dimer (FIG. 14).

As disclosed in Example 1 herein, the inventors now have a method for determining the redox state of Sec-TrxR and other selenoenzymes. The presence or absence of the dimedone dimer indicates whether or not the Sec-SeO$_2^-$ form is used during the redox cycle of the enzyme. This is analogous to work done previously in developing reagents for the detection of the corresponding sulfinic acid (Lo Conte, M., et al. (2015) A Chemical Approach for the Detection of Protein Sulfinylation. *ACS Chem Biol* 10, 1825-1830). The reaction shown in the right-hand panel of FIG. 14 underscores the very high electrophilicity of Se-oxides relative to S-oxides, as dimedone will not react with the corresponding sulfinic acid.

Figure 17:
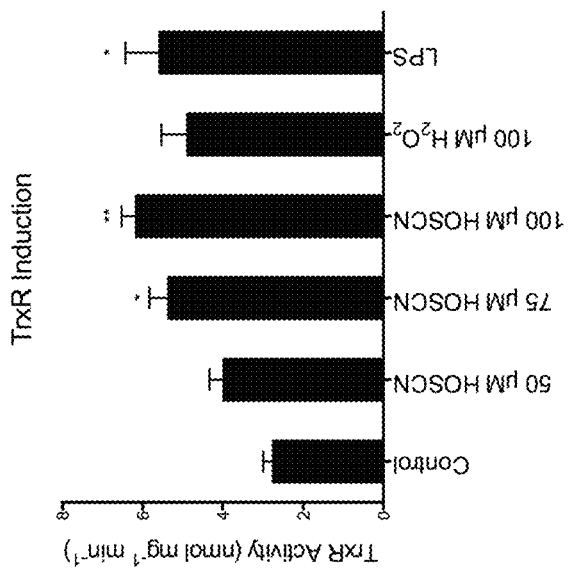
FIG. 17. HOSCN induces Sec-TrxR activity in J774 cells. Cells were exposed to increasing concentrations of HOSCN, hydrogen peroxide or 100 ng/ml PA LPS for 2 hours and then cell lysates where measured 24 hours later for Sec-TrxR activity.

The role of extracellular SCN in modulating neutrophil responses to infectious stimuli, and to test how this impacts their ability to kill or suppress bacterial growth and attenuate pro-inflammatory environments is determined as provided for in Example 3 herein. De-identified human blood neutrophils from normal and CF subjects are used. Readouts include changes in bacterial growth rates, phagocytosis, and cytokine release over time correlated to changes in intracellular ⁻SCN and Sec-TrxR levels. Additionally, how extracellular thiol levels modulate leukocyte function by changing intracellular thiol status and its known effects on dampening NFkB cell signaling pathways based on previous work with GSH (Gould, N. S., et al. (2011) Macropinocytosis of extracellular glutathione ameliorates tumor necrosis factor alpha release in activated macrophages. *PLoS One* 6, e25704) is disclosed. Preexisting data in the literature (Zhang, F., et al. (2008) Glutamine reduces TNF-alpha by enhancing glutathione synthesis in lipopolysaccharide-stimulated alveolar epithelial cells of rats. *Inflammation* 31, 344-350) suggest that changes in intracellular redox status dampens the NFkB signaling pathways and are important in pro-inflammatory responses. These data support the in vivo studies. Since HOSCN is an oxidant and capable of redox signaling, examination of whether it can regulate its own metabolism by inducing Sec-TrxR expression is done. Published data suggests that macrophage Sec-TrxR1 is induced by LPS that involves p38MAP kinase and IKK (Carlson, B. A., et al. (2011) Protein kinase-regulated expression and immune function of thioredoxin reductase 1 in mouse macrophages. *Mol Immunol* 49, 311-316) and nrf2 inducers such as sulforaphane and iberin (Barrera, L. N., et al. (2012) TrxR1 and GPx2 are potently induced by isothiocyanates and selenium, and mutually cooperate to protect Caco-2 cells against free radical-mediated cell death. *Biochim Biophys Acta* 1823, 1914-1924). Data indicates that HOSCN can directly induce the expression and activity of Sec-TrxR (FIG. 17).

Figure 18:
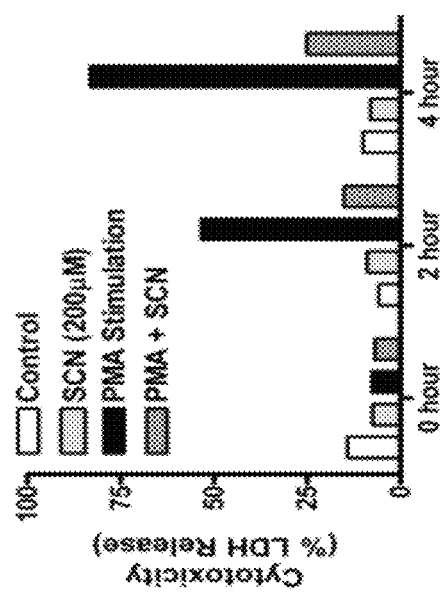
FIG. 18. Cytoprotective effects of $^-$SCN on activation-induced injury in neutrophils. Human peripheral blood neutrophils were isolated and activated with 20 ng/ml of phorbol myristate acetate (PMA) with and without 200 µM thiocyanate ($^-$SCN). Cytotoxicity was assessed by measuring lactate dehydrogenase (LDH) release.

CF is a genetic disease due to mutations in the cftr gene that produce either no or a dysfunctional CFTR protein and leads to well documented chronic lung infections, inflammation, and oxidative stress. The inventors have previously published on the role of CFTR in partially maintaining basal ELF GSH and its role in GSH adaptive responses to infection (Day, B. J., et al. (2004) Role for cystic fibrosis transmembrane conductance regulator protein in a glutathione response to bronchopulmonary *pseudomonas* infection. *Infect Immun* 72, 2045-2051) and cigarette smoke (Kariya, C., et al. (2008) *Mycoplasma pneumoniae* infection and environmental tobacco smoke inhibit lung glutathione adaptive responses and increase oxidative stress. *Infect Immun* 76, 4455-4462). Data is provided showing that a similar scenario exists for CFTR with ⁻SCN, except that ⁻SCN is even more dependent on functional CFTR than GSH (Gould, N. S., et al. (2010) Hypertonic saline increases lung epithelial lining fluid glutathione and thiocyanate: two protective CFTR-dependent thiols against oxidative injury. *Respir Res* 11, 119). CFTR regulates ⁻SCN levels in the ELF, which ⁻SCN is a potent antioxidant and also has a substantial role in lung host defense. The rationale for studying neutrophils is the large database that suggest these leukocytes have important roles in maintaining host defense and inflammation in the lung and are a major source of oxidative stress and may be a vulnerable target to damage from deficiencies in the HOSCN/Sec-TrxR detoxification pathway. Data demonstrating that SCN is cytoprotective in human neutrophils activated with phorbol myristate acetate (PMA) is provided (FIG. 18). These findings are interesting given that ⁻SCN is abundant in all human extracellular fluids (Chandler, J. D., and Day, B. J. (2015) Biochemical mechanisms and therapeutic potential of pseudohalide thiocyanate in human health. *Free Radic Res* 49, 695-710), but never added in cell culture studies involving innate immune cells.

Determination of ⁻SeCN therapy to alter host defense and inflammatory responses in lung infection models in shown in Example 4 herein. The $CF^{-/-}$ mice which are known to have increased inflammatory and morbidity responses to PA airway infection (FIG. 20) is used. Previous studies delineate a differential thiol response between wild type and $CF^{-/-}$ mice to hypertonic saline (Gould, N. S., et al. (2010)). This is a useful model to establish whether differential thiol responses contribute to $CF^{-/-}$ mouse sensitivity towards airway infection and whether one can improve this by supplementation with ⁻SeCN. Data on ⁻SCN delivery by nebulization also supports the feasibility of achieving pharmacological levels of ⁻SeCN (FIG. 21). Recent publications support efficacy of ⁻SCN in these PA infection models (Chandler, J. D., et al. (2015) Antiinflammatory and Antimicrobial Effects of Thiocyanate in a Cystic Fibrosis Mouse Model. *Am J Respir Cell Mol Biol* 53, 193-205, Chandler, J. D., et al. (2013) Nebulized thiocyanate improves lung infection outcomes in mice. *Br J Pharmacol* 169, 1166-1177). ⁻SeCN is used in a similar manner that hypertonic saline is used in the clinic to treat CF patients which is a 30-minute nebulization done twice daily. Treatments are to be started one day after the bacterial inoculums.

Figures 8A, 8B, 8C:
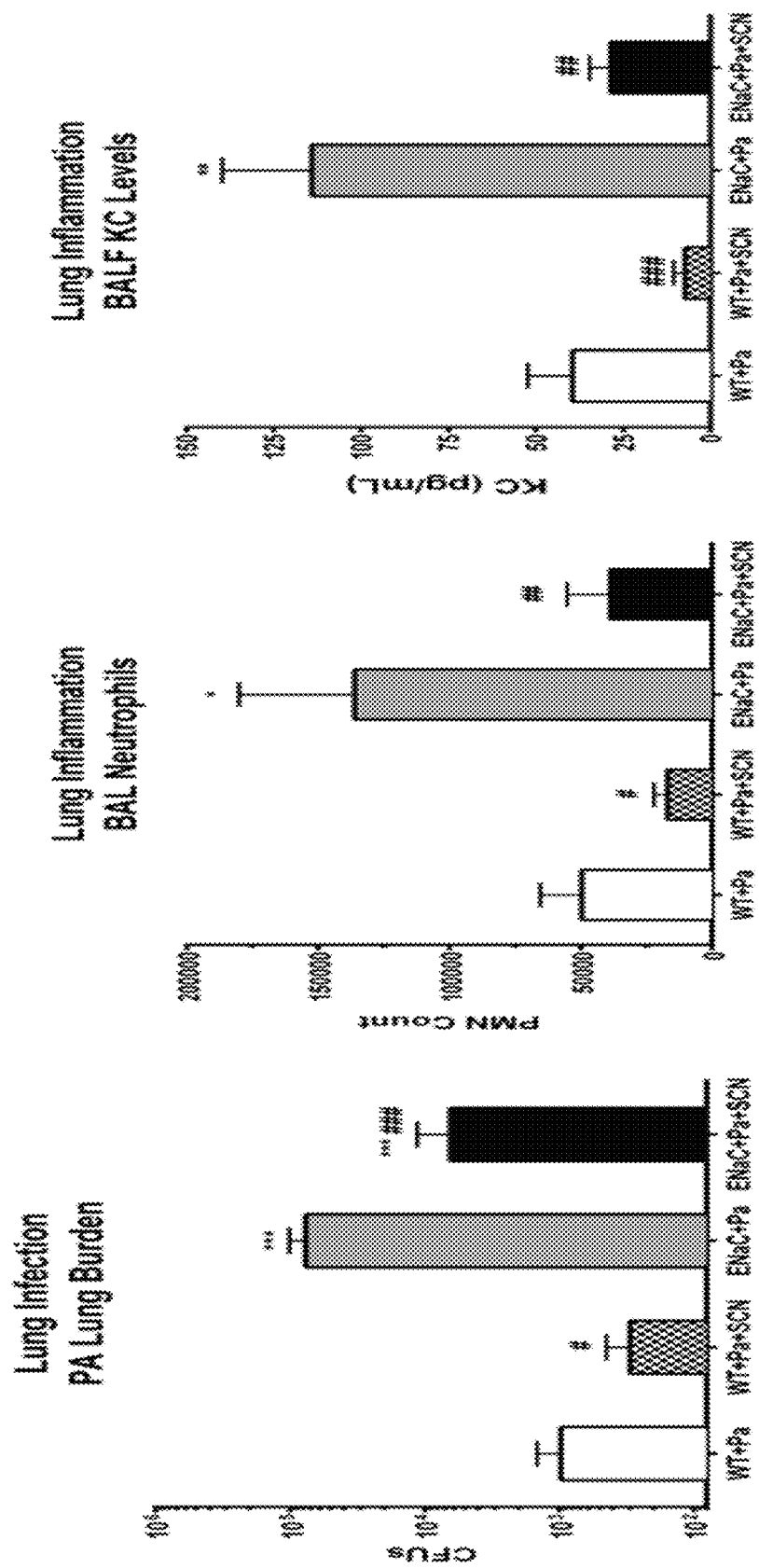
FIGS. 8A-8C. Nebulized $^-$SCN has anti-microbial and anti-inflammatory effects in mouse PA lung infection models. Wild type (WT) and beta-subunit of the epithelial Na(+) channel (βENaC) Tg Mice were nebulized with 0.5% $^-$SCN twice-daily starting 24 hrs post infection. Mice were sacrificed 72 hrs post infection and lung burden of PA was assessed (FIG. 8A), BAL neutrophil counts (FIG. 8B), and BALF KC cytokine (IL-8 analog) levels determined (FIG. 8C).

The rationale for supplementing with ⁻SeCN is due to the inventor's previous novel studies that showed a lack of restoration of ELF ⁻SCN levels with hypertonic saline nebulization (Gould, N. S., et al. (2010) Hypertonic saline increases lung epithelial lining fluid glutathione and thiocyanate: two protective CFTR-dependent thiols against oxidative injury. *Respir Res* 11, 119). There is data to support the feasibility of raising ELF ⁻SCN levels by inhalation (FIG. 21) which was well tolerated in mice and has a positive effect on PA lung infection (FIGS. 8A-8C). The inventors have developed a system to establish airway obstruction with or without bacterial infection in congenic $CF^{-/-}$ (gut corrected S489X functional null), β-ENaC Tg, and wild type mice. This is accomplished using a more biologically relevant matrix (fibrin rather than agar) which is a major constituent of obstructing airway secretion in PA lung infection—in both CF and non-CF patients (Seear, M., et al. (1997) Bronchial casts in children: a proposed classification based on nine cases and a review of the literature. *Am J Respir Crit Care Med* 155, 364-370).

A subject "in need thereof" as used herein refers to a subject that can benefit from the therapeutic and/or prophylactic effects of the pharmaceutical compositions of the present invention. Such a subject can be a subject diagnosed with a disease or disorder of this invention, a subject suspected of having or developing a disorder or disease of this invention, and/or a subject determined to be at increased risk of having or developing a disease or disorder of this invention.

By the term "treat," "treating," or "treatment of" (and grammatical variations thereof) it is meant that the severity of the subject's condition is reduced, at least partially improved or ameliorated, and/or that some alleviation, mitigation or decrease in at least one clinical symptom is achieved and/or there is a delay in the progression of the disease or disorder.

The terms "prevent," "preventing," and "prevention of" (and grammatical variations thereof) refer to reduction and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of a composition of the present invention.

As used herein, the terms "therapeutically effective amount" or "effective amount" refer to an amount of a composition or formulation of this invention that elicits a therapeutically useful response in a subject. Those skilled in the art will appreciate that the therapeutic effects need not be complete or curative, as long as some benefit is provided to the subject.

In the method described above, the disease or disorder can be, but is not limited to, cystic fibrosis (CF), chronic inflammatory lung disease, pulmonary fibrosis, pulmonary vasculitis, pulmonary sarcoidosis, inflammation and/or infection associated with lung transplantation, acute lung rejection, pulmonary artery hypertension, bronchitis, sinusitis, asthma, bacterial infection (e.g., by *Pseudomonas aeruginosa*, anthrax, *Mycobacterium*) fungal infection (e.g., by *Aspergillus, Pneumocystis carnii*), parasite infection, viral infection, chronic obstructive pulmonary disease (COPD), bronchiolitis obliterans syndrome (BOS), primary ciliary dyskinesia (PCD), idiopathic pulmonary fibrosis (IPF), alveolar protienosis, eosinophilic pneumonia, eosinophilic bronchitis, acute respiratory distress syndrome (ARDS), inflammation and/or infection associated with mechanical ventilation, ventilator-associated pneumonia, asbestos-related airway disorder or disease, dust-related airway disorder or disease, silicosis, chemical agent-related airway disease or disorder and any combination thereof. In one aspect, the disease is a pulmonary disease such as cystic fibrosis, pneumonia, viral pulmonary infection, bacterial pulmonary infection, fungal pulmonary infection, acute respiratory distress syndrome, asthma, chronic obstructive pulmonary disease, interstitial lung disease, bronchiectasis, sarcoidosis, idiopathic pulmonary fibrosis, bronchopulmonary dysplasia, rhinitis, and sinusitis. In one aspect, the disease is a result of or is caused by a bacterial infection, a viral infection or a fungal infection. In one aspect, the bacterial infection is a result or is caused by a bacteria selected from the group consisting of *Pseudomonas aeruginosa, Burkholderia cepacia* complex, methicillin-resistant *Staphylococcus aureus* and *Mycobacterium*. In still another aspect, the disease is an ocular disease such as a viral eye infection, bacterial eye infection, fungal eye infection, dry eye, and/or uveitis. In still another aspect, the disease is a skin disease such as a viral skin infection, bacterial skin infection, fungal skin infection, atopic dermatitis, skin wound, and/or eczema.

The present invention also provides a method of treating inflammation in the airway of a subject (e.g., a subject in need thereof), comprising delivering to the subject an effective amount of the pharmaceutical composition of this invention. In one aspect, the subject is further administered an inflammatory agent such as one or more of the following: nonsteroidal anti-inflammatories (NSAIDS), resolvins, glucocorticoids, neutralizing antibodies of cytokines and chemokines and soluble receptor classes, antihistamines, and protease inhibitors.

The present invention also provides a pharmaceutical composition comprising selenocyanate, hyposelenocyanite or a pharmaceutically acceptable salt thereof. In other aspect, the invention provides a pharmaceutical composition comprising a selenocyanate conjugate or a pharmaceutically acceptable salt thereof. These conjugates are to thiol containing molecules through diseleno and selenosulfide bonds. Examples include but are not limited to glutathione (GS-SeCN), N-acetylecysteine (NACS-SeCN) and cysteine (CyS-SeCN). Phenyl seleno-SeCN and 2-seleno-β-cyclodextrin-SeCN are examples of diseleno compounds. Other examples include common thiol compounds such a peroxiredoxin-SeCN and thioredoxin-SeCN. Another example is a conjugate to thiosulfate (thiosulfate-SeCN).

Another embodiment of the invention relates to the use of any of the compositions described herein the treat pulmonary disease, inhibit microbial growth, fungal growth or viral growth in an airway of a subject, and/or to inhibit inflammation in an airway of a subject.

While not wishing to be bound by a particular theory, it is expected that the formulations and/or compositions disclosed herein are effective in achieving and maintaining either a normal lung mucosa, or at least a more normal lung mucosa, which is an important factor in maintaining lung health. Drugs administered to the lungs are often associated with certain side effects, in some cases because of dosage, and in other cases because they damage the lung tissue. In some embodiments, therapeutic agents combined with the formulations and/or compositions disclosed herein are effective at lower doses, and at such lower doses, the incidence of side effects can be reduced. For example, one can decrease inhaled corticosteroid (ICS) dosing and, accordingly, reduce the risk of pneumonia in chronic obstructive pulmonary disease (COPD) patients, and reduce the dose of β-agonists and other bronchodilators to reduce the risk of death in asthma patients.

In other embodiments, where the therapeutic agent interacts unfavorably with lung tissue, the formulations and/or compositions described herein can help to restore homeostasis to the lung tissue, and thus help minimize or eliminate damage caused by the therapeutic agents.

The present invention also provides a method of treating an airway disorder or disease in a subject in need thereof, comprising delivering to the subject an effective amount of the pharmaceutical compositions described herein, optionally in combination with a steroid and/or bronchodilator, such as a beta$_2$-agonist.

Furthermore, the present invention provides a method of treating an infection in the airway of a subject in need thereof, comprising delivering to the subject an effective amount of the pharmaceutical composition described herein, optionally in combination with one or more antibiotics. The antibiotics can be administered locally to the lungs and/or systemically.

Inflammation in the airway of a subject in need thereof can be treated by delivering to the subject an effective amount of the pharmaceutical compositions described herein.

The compositions of the present invention are administered in a manner compatible with the dosage formulation in such an amount as will be effective for the desired result. In particular embodiments, the pharmaceutical composition is administered to the subject in a therapeutically effective amount. The quantity to be administered depends on a number of factors, such as, e.g., the subject to be treated and the severity of the condition. In general, the dose per subject may be 50 or 250 up to 5 mg, or 10 mg per dose. Exemplary dosages include from about 0.001, 0.01 or 0.1 to about 1, 5, or 10 mg/dose, e.g., 1, 2, 3, or more times daily, two to four times weekly, weekly, two to three times monthly or monthly, or as needed by the subject. In particular, the dose is administered once or twice daily and for no more than about for 30 days.

The composition of this invention can be administered for a sustained period, such as for at least about one month, at least about 2 months, or at least about 3 months. Preferably, the composition is administered for 2 weeks to about 1 month.

Any suitable dosing schedule can be followed. For example, the dosing frequency can be a once weekly dosing. The dosing frequency can be a once daily or multiple times daily dosing. The dosing frequency can be more than once weekly dosing. The dosing frequency can be more than once daily dosing, such as any one of 2, 3, 4, 5, 6, 7, 8, 9, 10 or more than 10 daily doses. The dosing frequency can be intermittent (e.g., multiple daily dosing for 7 days followed by no doses for 7 days, repeated for any 14 day time period, such as 2 months, 4 months, 6 months or more). The dosing frequency can be continuous (e.g., one weekly dosing for continuous weeks).

In some embodiments, the pharmaceutical composition of this invention can be administered in a single "shock" dose, for example, during a bronchoscopy.

In other embodiments, the methods and/or use of the invention can be carried out on an as-needed basis by self-medication.

In other embodiments, the composition of the invention is administered by an inhaler.

Any of the dosing frequencies can be used with any dosage amount. Further, any of the dosing frequencies and/or dosage amounts can be used with any of the pharmaceutical compositions described herein.

The effectiveness of the pharmaceutical composition(s) and/or the method of treatment(s) of the invention can be determined by determining and/or monitoring the levels of pathogen tiers, and cytokines and/or by determining organ and/or tissue function in the subject. For example, a decreased pathogen tiers and/or decreases in one or more markers of inflammation (i.e. cytokines) can be determined for the subject. The levels can be determined in the subject prior to administration of the composition (and/or treatment) and then compared to levels determined following administration of the composition (and/or treatment) to the subject. The levels can also be compared to a control level (i.e. level from one or more subjects without treatment). In addition, improved organ and/or tissue function in the subject can be determined by comparting the subject's organ and/or tissue function prior to administration of the composition and/or treatment as compared to the organ and/or tissue function of the subject following treatment and/or compared to a control.

The pharmaceutical composition can be delivered in any suitable volume of administration. In representative embodiments of the invention, the administration volume for intranasal delivery ranges from about 25 microliters to 200 microliters or from about 50 to 150 microliters or from about 50, 100, 250 or 500 microliters to about 1, 2, 3, 3.5 or 4 milliliters in a human. Typically, the administration volume is selected to be large enough to allow for delivery of therapeutic quantities while accounting for dilution in airway surface liquid (ASL) in maintenance conditions in relatively "normal" airways (10-30 ml ASL) and in cystic fibrosis (CF) airways (40-50 ml ASL or more plus thick, tenacious, and heavily infected mucus secretions).

"Administration by inhalation" or "delivery by inhalation" means administration to or delivery to the subject through the mouth and/or nose.

The term "intranasal administration" as used herein, refers to a systemic form of administration of a pharmaceutical composition of this invention, whereby the composition is introduced into one or both of the nasal passages of a subject such that the composition contacts the nasal mucosa and in some embodiments, is absorbed into the systemic circulation. In certain embodiments, a therapeutically effective amount is administered. Intranasal administration of the pharmaceutical compositions of the present invention can comprise a single administration or multiple administrations of the compositions.

Intranasal administration of the pharmaceutical compositions of the present invention can be achieved by any known method. In particular embodiments, intranasal administration is by inhalation (e.g., using an inhaler, atomizer or nebulizer device), alternatively, by spray, tube, catheter, syringe, dropper, packtail, pipette, pledget, and the like. As a further illustration, the pharmaceutical composition can be administered intranasally as nose drops, powder or liquid sprays or aerosols, liquids or semisolids by syringe, liquids or semisolids by swab, pledget or other similar means of application, a gel, cream or ointment, an infusion, or by injection, or by any means now known or later developed in the art. In particular embodiments, the method of delivery is by nasal drops, spray or aerosol. As used herein, aerosols can be used to deliver powders, liquids or dispersions (solids in liquid).

In some embodiments, the pharmaceutical compositions of this invention are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition of the invention may be presented without excipients.

Spray compositions for topical delivery to the lung by inhalation may be formulated as aqueous solutions or suspensions or as aerosols delivered from pressurized packs, such as a metered dose inhaler (MDI), with the use of a suitable liquefied propellant. The medication in pressurized MDI is most commonly stored in solution in a pressurized canister that contains a propellant, although it may also be a suspension.

Aerosol compositions suitable for inhalation can be presented either as suspensions or as solutions and typically contain the active compound and a suitable propellant such as a fluorocarbon or hydrogen-containing chlorofluorocarbon or mixtures thereof, particularly hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof.

The aerosol composition may optionally contain additional excipients typically associated with such compositions, for example, surfactants such as oleic acid or lecithin and co-solvents such as ethanol. Pressurized formulations will generally be contained within a canister (for example an aluminum canister) closed with a metering valve and fitted into an actuator provided with a mouthpiece.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical composition of this invention is administered from a dry powder inhaler.

The pharmaceutical compositions described herein can be present in the form of solid formulations, such as particulate formulations, or in solution form. When in particulate form, the particles can be mixed with gases, or liquid propellants, for use in inhalation therapy. Other solid formulations include formulations for oral administration, topical administration, buccal administration, colonic administration, and suppositories for rectal or vaginal administration. Representative formulations include, but are not limited to, the following: eye drops, nebulizers, topical gels, topical ointments, lotions, dry powders, particles, sprays, liquids, anesthetic machines or vaporizers, autoinjectors, intrauterine devices, respimats, liniments, liposomes, formulations for intramuscular, intrathecal, or subcutaneous injection, douches, infusions, and face masks.

In solution form, the formulations can be in the form of sprays for intranasal administration, formulations for use in nebulizers, and formulations for rectal administration, such as enemas and colonies. Solutions that include water-miscible organic solvents, such as propylene glycol and/or glycerol, and other components normally found in vaginal and rectal lubricants, can also be used.

In still further embodiments, the composition is combined with one or more additional therapeutic agents. Representative therapeutic agents include, but are not limited to, monoclonal antibodies, immunomodulatory agents, including agents that cause T and B cell activation, proliferation, and/or maturation; agents that bring about innate immune system activation, proliferation, maturation (e.g., JNK, MAPK, ERK, NK kappa B pathway agonists or antagonists, and monocyte, neutrophil, or macrophage agonists or antagonists), matrix metalloproteinase inhibitors, heat shock protein agonists or antagonists, alpha synuclein inhibitors, chelating agents, diuretics, alpha 1 antitrypsin modulators, purinoceptor agonists or antagonists, cyclooxygenase 2 inhibitors, DNA gyrase inhibitors, natural killer cell and natural killer T cell agonists or antagonists, cathepsin class agonists or antagonists, antioxidant therapies, rho-associated kinase inhibitors, myosin inhibitors, phosphatidylinositol 3 kinase inhibitors and related molecules, nitric oxide synthase agonists or antagonists, nitric oxide agonists or antagonists, ion channel function or trafficking modulators, surfactant therapies, in particular, lung surfactants, cannabinoid receptor modulators, complement system inhibitors, IgE receptor antagonists, G protein-coupled receptor agonists or antagonists, chemokines, chemokine receptor agonists or antagonists, cytokines, and cytokine receptor agonists or antagonists, arachidonic acid agonists or antagonists, inflammatory mediators, STAT6 inhibitors, histamine or leukotriene agonists or antagonists, and calcineurin agonists or antagonists.

The formulations and/or compositions may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Bactericidal and Bacteriostatic Agents ("Antibiotics") Bactericidals kill bacteria directly, whereas bacteriostatics prevent them from dividing. However, these classifications are based on laboratory behavior. In practice, both can prevent a bacterial infection. They work through a variety of mechanisms (e.g., DNA gyrase inhibition, inhibiting bacterial cell wall synthesis, binding to the bacterial ribosomal subunits, and inhibiting protein synthesis). Some examples of the classes of antibiotics are multiple generations of cephalosporins, fluoroquinolones, and aminoglycosides.

To treat pulmonary infections, the formulations described herein can be combined with antibiotics, whether in the same inhaled formulation (i.e., via pulmonary delivery or intranasal delivery), or where the antibiotics are administered by another route, such as the oral or injectable routes. Representative antibiotics useful in treating pulmonary infections include, but are not limited to, penicillins including but not limited to: Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, and Ticarcillin, and combinations of penicillins with other therapeutic agents, including but not limited to: Amoxicillin/clavulanate, Ampicillin/sulbactam, Piperacillin/tazobactam, and Ticarcillin/clavulanate. Additional therapeutic agents include aminoglycosides such as Kanamycin A, Amikacin, Tobramycin, Dibekacin, Gentamicin, Sisomicin, Netilmicin, Neomycin B, Neomycin C, Neomycin E (paromomycin) and Streptomycin.

When the compounds described herein are used in conjunction with antibiotics, they can reduce dosages of the antibiotics, limiting exposure to toxic drug levels and/or the side effects associated with antibiotics (i.e., drug resistance and diarrhea), in some embodiments by helping wounded mucosal tissues to heal and/or resist further infection.

Surfactant therapies, in particular, lung (pulmonary) surfactants: Surfactants are compounds that lower the surface tension or interfacial tension between two liquids or between a liquid and a solid. Surfactants may act as detergents, wetting agents, emulsifiers, foaming agents, or dispersants.

Pulmonary surfactants are surface-active lipoprotein complexes (phospholipoprotein) formed by type II alveolar cells. The proteins and lipids that comprise the surfactant have both a hydrophilic region and a hydrophobic region. By adsorbing to the air-water interface of alveoli with the hydrophilic head groups in the water and the hydrophobic tails facing towards the air, the main lipid component of surfactant, dipalmitoylphosphatidylcholine (DPPC), reduces surface tension.

In the lungs, surfactant reduces the surface tension and helps to maximize the surface area available for gas exchange. Without adequate surfactant, a baby works much harder to breathe, becomes exhausted, and does not get enough oxygen. There are various pulmonary disorders associated with not having sufficient amounts of pulmonary surfactants, including infant respiratory distress syndrome (IRDS), hyaline membrane disease, congenital surfactant deficiency, and pulmonary alveolar proteinosis. Synthetic lung surfactants can be administered to overcome the deficiency. Perhaps the most widely-administered pulmonary surfactant is CUROSURF® (Cornerstone Therapeutics).

When a lung surfactant is combined with the therapeutic agents described herein, the resulting therapy can reduce dosages of other therapies, thereby limiting exposure to toxic drug levels. Additionally, it can be used in conjunction with other therapies to increase efficacy and/or decrease side effects.

A composition, including a pharmaceutical composition, can also include, for example, a pharmaceutically acceptable carrier, which includes pharmaceutically acceptable excipients and/or delivery vehicles, for delivering a protein or nucleic acid molecule or other regulatory compound to a patient. Additionally, a composition, including a pharmaceutical composition of the present invention can be administered to a patient in a pharmaceutically acceptable carrier. As used herein, a pharmaceutically acceptable carrier refers to any substance suitable for delivering a compound useful in the method of the present invention to a suitable in vivo or ex vivo site. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled-release formulation that is capable of slowly releasing a composition of the present invention into a patient. As used herein, a controlled-release formulation comprises one or more therapeutic agents of the present invention in a controlled-release vehicle. Suitable controlled-release vehicles include, but are not limited to, biocompatible polymers, other polymeric matrices, capsules, microcapsules, microparticles, bolus preparations, osmotic pumps, diffusion devices, liposomes, liposheres, and transdermal delivery systems.

Other embodiments of the invention include kits comprising the pharmaceutical products of the present invention are also provided. The kits can comprise a composition comprising s selenocyanate, hyposelenocyanite or a selenocyanate conjugate formulated for example by administration by inj. The kits may contain unit-dose or multi-dose sealed containers, for example, inhaler, ampoules and vials, and may be stored in a lyophilized condition requiring only the addition of the sterile liquid carrier, for example water for injection, immediately prior to use. The kits may also be stored in a condition, wherein the contents are ready for direct use. The kits comprise a container comprising selenocyanate, hyposelenocyanite or a selenocyanate conjugate. The kits may further comprise one or more additional containers each holding one or more other drugs/agents suitable for use in the methods of the invention. Suitable containers include inhalers, vials, bottles (including with a bottle with a dropper or a squeeze bottle), blister packs, jars, nebulizers, packets (e.g., made of foil, plastic, paper, cellophane or another material), syringes and tubes. The kit will also contain instructions for administration of the composition and, optionally, the one or more other drugs/agents suitable for use in the methods of the invention. The instructions may, for instance, be printed on the packaging holding the container(s), may be printed on a label attached to the kit or the container(s), or may be printed on a separate sheet of paper that is included in or with the kit. The packaging holding the container(s) may be, for instance, a box, or the container(s) may wrapped in, for instance, plastic shrink wrap. The kit may also contain other materials which are known in the art and which may be desirable from a commercial and user standpoint.

As used in the description of the invention and the appended claims, the singular forms "a," "an" and "the" are intended to include the plural forms as well, unless the context clearly indicates otherwise. For example, "a cell" can mean a single cell or a multiplicity of cells.

Also as used herein, "and/or" refers to and encompasses any and all possible combinations of one or more of the associated listed items, as well as the lack of combinations when interpreted in the alternative ("or").

Additional objects, advantages and novel features of the present invention will become apparent to those skilled in the art by consideration of the following non-limiting examples. The following experimental results are provided for purposes of illustration and are not intended to limit the scope of the invention.

EXAMPLES

Example 1

Determination of the Chemical Mechanism by which Sec-Containing TrxR Resists Inactivation by HOSCN/HOSeCN Oxidation.

To determine the redox state of the Sec residue of TrxR upon exposure to $H_2O_2$ (and other oxidants such as HOSCN), the wild-type (WT) enzyme is reduced with NADPH. Oxidant and dimedone are added simultaneously to the sample, followed by mass-spectrometry (MS) analysis. If the dimedone dimer is detected, then the Sec-$SeO_2^-$ form is used and repaired by the enzyme. Conditions are used in a manner wherein it is known that the concentration of oxidant does not inactivate the enzyme. If the dimedone dimer cannot be detected, this indicates that the role of the resolving Cys residue is to protect the Sec residue from overoxidation. To test this possibility, a mutant form of TrxR is made in which the resolving Cys residue (FIG. 13) is mutated to alanine (Ala). The mutant's ability to resist oxidative inactivation compared to the WT enzyme is tested. For this assay, an alternative substrate is used, selenocystine instead of Trx, since it is known that mutations in the C-terminal redox center do not completely abolish this activity. If the mutant shows much less resistance to oxidative inactivation compared to WT, then this indicates that the resolving Cys residue prevents overoxidation of the Sec residue to Sec-$SeO_2^-$. To be conclusive, the dimedone alkylation experiment is repeated with the mutant under conditions in which the mutant is largely inactivated, but the WT enzyme is not. If the dimedone dimer is detected in the mutant, then this indicates that the mutant enzyme is overoxidized to Sec-$SeO_2^-$, which then undergoes β-elimination to form dehydroalanine (DHA). The DHA form is trapped and detected by using biotin-conjugated cysteamine (Okeley, N. M., et al. (2000) Facile chemoselective synthesis of dehydroalanine-containing peptides. *Org Lett* 2, 3603-3606), which will form a covalent thioether linkage. This adduct is detected by MS analysis after proteolysis. Using a similar approach to analyze Cys-TrxRs, the mechanism by which Cys-TrxRs are inactivated is expected to be due to overoxidation of Cys to Cys-$SO_2^-$ and/or formation of DHA.

Example 2

Determination of the Role of Cys-TrxR Inactivation by HOSCN in Suppressing Lung Bacterial Colonization.

Figure 15:
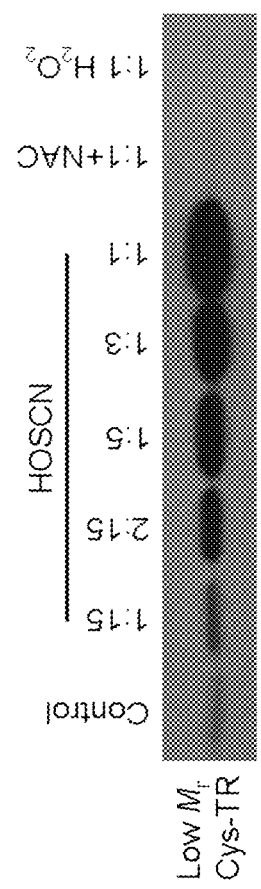
FIG. 15. Western blot of sulfenic acid (dimedone label) formation on purified *E. coli* Cys-TrxR after 5 minutes HOSCN exposure (molar ratios label each lane) or plus 1 minute PBS or N-acetylcysteine (NAC). For lane 8, $H_2O_2$ was used instead of HOSCN.

HOSCN is an interesting oxidant due to its affinity for only very acidic thiol groups on proteins (Barrett, T. J., et al. (2012) Inactivation of thiol-dependent enzymes by hypothiocyanous acid: role of sulfenyl thiocyanate and sulfenic acid intermediates. *Free Radic Biol Med* 52, 1075-1085). This property of HOSCN allows it to diffuse much easier to distant targets. Cys-TrxR has two cysteine residues in its active site that are acidic and it is expected that HOSCN oxidizes them as part of its mechanism of inactivation. Data has shown that dimedone labels sulfenic acid residues in *E. coli* Cys-TrxR upon selective thiol oxidation by HOSCN (FIG. 15). Cys-TrxR was rapidly oxidized by HOSCN but not $H_2O_2$ which was reversible by N-aceylcysteine (NAC). This probe can be used in tandem with western blotting and LC-MS approaches to characterize thiol oxidation of bacterial Cys-TrxRs. Although previous studies have looked at potential bacteria targets for oxidative inactivation by oxidants produced by haloperoxidases, Cys-TrxR was not previously identified (Tenovuo, J., and Pruitt, K. M. (1984) Relationship of the human salivary peroxidase system to oral health. *J Oral Pathol* 13, 573-584). The novel finding herein that Cys-TrxR not only does not metabolize HOSCN but is inactivated indicates that the bactericidal properties of HOSCN can be related to Cys-TrxR functions in bacteria.

Figure 16:
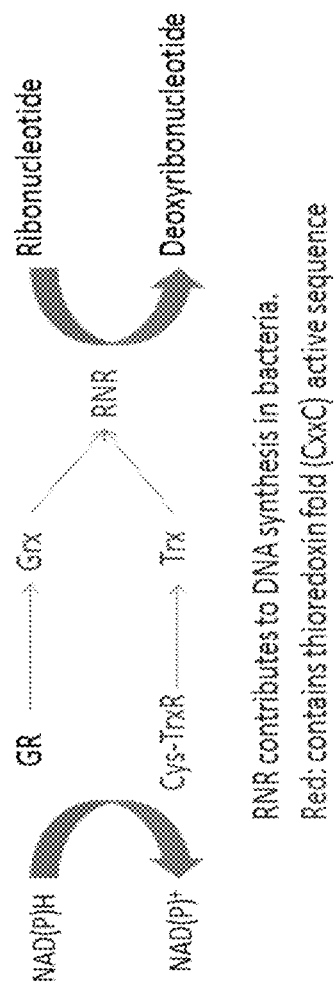
FIG. 16. Ribonucleotide reductase (RNR) requires either reduced glutaredoxin (Grx) or thioredoxin (Trx) as cofactors for deoxyribonucleotide synthesis. Both Grx and and Trx have thioredoxin folds that contain acidic thiols that may be sensitive to HOSCN inactivation as shown with Cys-TrxR.

Cys-TrxR functions in bacteria in a similar manner as Sec-TrxR does in mammals and reduces oxidized thioredoxin (Trx). Trx plays multiple roles in repairing oxidized cysteine residues in proteins, maintaining redox tone, scavenging cellular peroxides and as a cofactor for cellular reductases, such as ribonucleotide reductase (RNR) (Orr, M. D., and Vitols, E. (1966) Thioredoxin from *Lactobacillus leichmannii* and its role as hydrogen donor for ribonucleoside triphosphate reductase. *Biochem Biophys Res Commun* 25, 109-115). RNR requires reducing equivalences from thioredoxin (Trx) or glutaredoxin (Grx) in the catalysis of ribonucleotide to deoxyribonucleotide and the oxidized forms of Trx and Grx are reduced back to their active forms by Cys-TrxR and glutathione reductase (GR), respectively (FIG. 16). RNR is required for DNA synthesis, repair, and cellular replication. It is interesting to note that many of these proteins including RNR contain thioredoxin folds with acidic thiols that are readily inactivated by HOSCN. Whether HOSCN/HOSeCN targets several of these proteins critical to bacterial DNA synthesis and repair is determined. Testing the Mechanism of Inactivation of Cys-TrxR by HOCl, HOSCN, and HOSeCN:

Data provides that Sec-containing TrxR2 (Sec-TrxR2) resists inactivation from HOCl, HOSCN, and HOSeCN, while DmTrxR (containing Cys) is inactivated by these oxidants. Based on data, it is expected that Sec-TrxR1 is able to metabolize both HOSCN and HOSeCN but not HOCl, and that Cys-TrxR's is unable to metabolize these oxidants. The active site Cys or Sec residue of each respective enzyme is oxidized to either $Cys-SO_2^-$ or $Sec-SeO_2^-$. The Cys-TrxR cannot recover from this oxidation while the Sec-TrxR can. To test this, an inactivation assay is performed followed by structural analysis of the protein by MS. In the inactivation assay, (i) enzymes are reduced with NADPH, (ii) the enzymes are treated with oxidant followed by desalting to remove oxidant, and (iii) the enzyme is assayed for activity. It is expected that Cys-DmTrxR and Cys-TrxR's are inactivated while Sec-TrxR largely resists inactivation. The proteins are proteolyzed followed by LC-MS analyses. The LC-MS profiles are compared to control samples not treated with oxidant. This determines the exact mechanism of inactivation for each enzyme. Further, this experiment is predicted to show that oxidation by HOCl is nonspecific and will oxidize multiple amino acid targets of a protein, while HOSCN/HOSeCN is more specific for thiol/selenol groups. This would explain why HOCl is highly inflammatory (nonspecific oxidation), and why HOSCN is used as a bactericide because it can rapidly inactivate proteins/enzyme by oxidation of sulfur amino acids (Cys, Met), but can be metabolized by the host cell by Sec-TrxR.

Several gram-negative bacteria (*Psuedomonas aeruginosa* (ATCC BAA-47), *Burkholderia cepacia* (ATCC 25416) and *Haemophilus influenza* (ATCC 9007)) and a gram positive bacterial (*Staphyloccus aureus* (ATCC 25923) and a nontuberculous mycobacterium (NTM) *Mycobacterium abscessus* (ATCC 19977)) Cys-TrxRs are screened for potential HOSCN oxidoreductase activity focusing on the most common microbes associated with lung colonization in CF (Rabin, H. R., and Surette, M. G. (2012) The cystic fibrosis airway microbiome. *Curr Opin Pulm Med* 18, 622-627; Zhao, J., et al. (2012) Decade-long bacterial community dynamics in cystic fibrosis airways. *Proc Natl Acad Sci USA* 109, 5809-5814). In addition to these more characterized bacterial strains from ATCC, matching de-identified CF clinical isolates are obtained from an Adult CF clinic (see FIG. 11). Data in antibiotic resistant clinical isolates from CF subjects shows a correlation between HOSCN reductase activity and viability (Table 2). Further characterization of the relationship of HOSCN reductase activity and resistance is undertaken.

TABLE 2

Viability after HOSCN exposure and HOSCN reductase activity.

| Strain | Viability (%) | Apparent $V_{max}$ (nmol $mg^{-1}$ $min^{-1}$) |
|---|---|---|
| E. coli: AB1157 | 0 | ND[c] |
| P. aeruginosa: PAO1 | 0 | ND[c] |
| P. aeruginosa: AMT0027L[a] | 0 | ND[c] |
| P. aeruginosa: AMT0105L[a] | 0 | ND[c] |
| P. aeruginosa: AMT0294L[a] | 0 | ND[c] |
| P. aeruginosa: AMT0009L[a] | 4.2 ± 2.1 | 0.8 ± 0.3 |

TABLE 2-continued

Viability after HOSCN exposure and HOSCN reductase activity.

| Strain | Viability (%) | Apparent $V_{max}$ (nmol $mg^{-1}$ $min^{-1}$) |
|---|---|---|
| P. aeruginosa: AMT0058L[a] | 0.7 ± 0.4 | 1.2 ± 0.2 |
| P. aeruginosa: AMT0145L[a] | 24.8 ± 2.5 | 1.4 ± 0.1 |
| H. sapiens: 16HBE[b] | 96.3 ± 1.6 | 14.7 ± 1.0 |

[a]Late disease antibiotic-resistant clinical isolate from CF patients.
[b]Human bronchial epithelial (16HBE) cells provided for comparison.
[c]No activity detected. Limit of detection = 0.5 nmol $mg^{-1}$ $min^{-1}$.

HOSCN's ability to target and inactivate proteins with thioredoxin folds that feed reducing equivalents to RNR along with RNR itself as depicted in FIG. 16 is studied. The gene sequences for prokaryotic Cys-TrxR (trxB), RNR, Trx and Grx for these strains listed above are found in NCBI gene resources and are used to select primers to clone the genes involved in DNA synthesis listed in FIG. 16. BLAST analysis for these proteins show about a 70% homology among gram negative bacteria and about 40% homology with the gram-positive strain. Plasmids containing gene of interest from each strain is overexpressed using the expression vector pQE30 which adds a His6 tag to the N-terminal end of the recombinant protein. The recombinant proteins are expressed in their respective strains and purified with a Ni-NTA agarose column as described (Kanzok, S. M., et al. (2002) Thioredoxin, thioredoxin reductase, and thioredoxin peroxidase of malaria parasite *Plasmodium falciparum*. *Methods Enzymol* 347, 370-381).

Whether HOSCN/HOSeCN can selectivity inactivate proteins involved in bacterial DNA synthesis and repair is determined using LC-MS approaches to characterize thiol oxidation (Barrett, T. J., et al. (2012) Inactivation of thiol-dependent enzymes by hypothiocyanous acid: role of sulfenyl thiocyanate and sulfenic acid intermediates. *Free Radic Biol Med* 52, 1075-1085) and correlates with loss of these enzyme activities and resultant depletion of nucleotide pools (Dennis, P. P., et al. (2004) Control of rRNA synthesis in *Escherichia coli*: a systems biology approach. *Microbiol Mol Biol Rev* 68, 639-668, Buckstein, M. H., et al. (2008) Characterization of nucleotide pools as a function of physiological state in *Escherichia coli*. *J Bacteriol* 190, 718-726) in culture after HOSCN/HOSeCN exposure.

Determination of Whether Bacteria are Protected when they Express the Mammalian Sec-TrxR:

Heterologous expression of Sec-proteins in bacteria requires the replacement of a Cys codon with a UGA codon (codes for Sec) as well as the use of bacterial SECIS-element fused to the 3'-end of the gene. This approach has been previously used to produce heterologous Sec-TrxR in *E. coli* (Amer, E. S. (2002) Recombinant expression of mammalian selenocysteine-containing thioredoxin reductase and other selenoproteins in *Escherichia coli*. *Methods Enzymol* 347, 226-235). Expression of Sec-TrxR, the Sec to Cys mutant TrxR, the Cys-ortholog TrxR (DmTrxR), native bacterial Cys-TrxR, and the Sec-rescue-TrxR is done by constructing the appropriate pET plasmid, inserting the plasmid into bacteria by transformation, and then inducing bacterial cultures with IPTG. After determining the optimal induction period, cells are transferred to a reaction cocktail containing the LPO system with either SCN or SeCN to generate respective HOSCN or HOSeCN in situ for 2 hours. Cells are returned to growth media and bacterial viability is assessed by a dilution method measuring colony forming units. That Sec will confer resistance to HOSCN/HOSeCN toxicity is predicted.

These studies provide insight on mechanisms and important regions of Sec-TrxR necessary to detoxify HOSC/HOSeCN and the basis for the observed selective evolutionary detoxification of HOSCN. These studies shed light on why certain bacterial strains tend to colonize the lungs of subjects with cystic fibrosis (CF) and a potential therapy to diminish chronic bacterial colonization that directly links to diminished CFTR function. Correlation of the oxidation of acidic thiol residues and inhibition of enzyme activity and bacterial viability is expected as seen for Cys-TrxR in both *E. coli* and several clinical PA isolates reported in Table 2. Given that RNR can use both the Cys-TrxR and GR pathways, all proteins in these pathways with a thioredoxin fold illustrated in FIG. 16 are expected to be inactivated except for GR which is closely related to mammalian GR that the inventor has shown to have weak HOSCN reductase activity (Chandler, J. D., et al. (2013) Selective metabolism of hypothiocyanous acid by mammalian thioredoxin reductase promotes lung innate immunity and antioxidant defense. *J Biol Chem* 288, 18421-18428). If recombinant prokaryotic protein activity is inhibited by the His6 N-terminal tag, over expression without the His-tag and use of conventional protein purification approaches for these proteins is used (Tamura, T., and Stadtman, T. C. (2002) Mammalian thioredoxin reductases. *Methods Enzymol* 347, 297-306).

Example 3

Examination of CFTR's and Sec-TrxR's Role in the Importance of ⁻SCN/HOSCN-Mediated Lung Host Defense Against Bacterial Infection.

De-identified human blood neutrophils obtained from normal and CF subjects are tested ex vivo for their ability to kill or suppress bacterial growth and change in cytokine release profile, phagocytosis and respiratory burst. Blood is collected by venous puncture and neutrophils separated using negative immunomagnetic separation (VarioMACS magnet, Miltenyi Biotech) as previously described (Cotter, M. J., et al. (2001) A novel method for isolation of neutrophils from murine blood using negative immunomagnetic separation. *Am J Pathol* 159, 473-481). This technique routinely provides greater than 95% pure neutrophil suspension of greater than 97% viability and a 70% yield of neutrophils from whole blood ($0.5 \times 10^6$ cells/ml). Basal responses are compared between normal and CF subjects. Additionally, responses are compared from neutrophils obtained from normal and CF subjects to test whether there are any inherent differences with a cross-over design that places the cells from normal subjects under $CF^{-/-}$ extracellular ⁻SCN conditions and cells from CF subjects under normal extracellular ⁻SCN conditions, ex vivo. Additional studies compare SCN responses to ⁻SeCN responses.

Temporal studies are conducted to see how long it takes for the extracellular environment to affect intracellular ⁻SCN/SeCN levels and stimulated responses from bacterial or PA LPS exposures. Controls are done without extracellular ⁻SCN/SeCN supplementation within common physiologic range 10-400 µM. Whether extracellular ⁻SCN/SeCN levels affect microbe growth in the presence or absence of leukocytes as previously described (Rigobello, M. P., et al. (2008) Gold(I) complexes determine apoptosis with limited oxidative stress in Jurkat T cells. *Eur J Pharmacol* 582, 26-34) is also tested. Additionally, if the changes in the extracellular thiol environment affects the gene regulation of Sec-TrxR which is thought to be under the regulation of several transcription factors including LPS (Carlson, B. A., et al. (2011) Protein kinase-regulated expression and immune function of thioredoxin reductase 1 in mouse macrophages. *Mol Immunol* 49, 311-316; Barrera, L. N., et al. (2012) TrxR1 and GPx2 are potently induced by isothiocyanates and selenium, and mutually cooperate to protect Caco-2 cells against free radical-mediated cell death. *Biochim Biophys Acta* 1823, 1914-1924), nrf2 (Sakurai, A., et al. (2005) Transcriptional regulation of thioredoxin reductase 1 expression by cadmium in vascular endothelial cells: role of NF-E2-related factor-2. *J Cell Physiol* 203, 529-537) and Oct-1 and Sp1/3 (Rundlof, A. K., et al. (2001) The core promoter of human thioredoxin reductase 1: cloning, transcriptional activity, and Oct-1, Sp1, and Sp3 binding reveal a housekeeping-type promoter for the AU-rich element-regulated gene. *J Biol Chem* 276, 30542-30551) is assessed.

Figure 19:
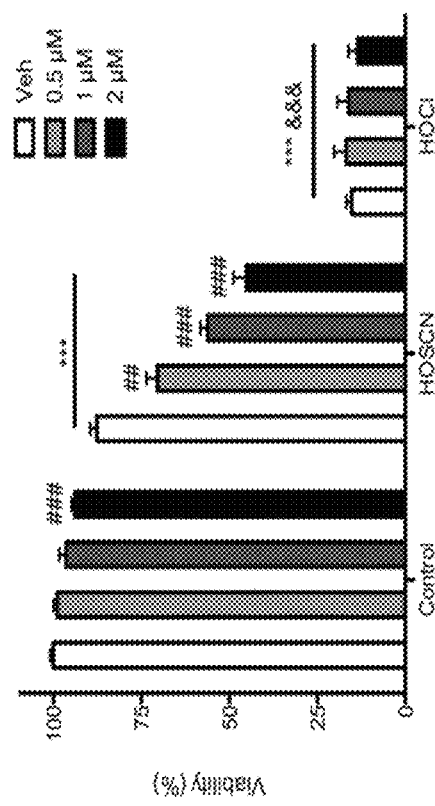
FIG. 19. Sec-TrxR inhibition with auranofin sensitizes lung cells to HOSCN-mediated toxicity. 16HBE cells were treated with auranofin at increasing concentrations for 1 hour and then exposed to 300 µM of either HOSCN or HOCl and viability was assessed by lactate dehydrogenase release 24 hours later. Vehicle (Veh).
Figure 22A:
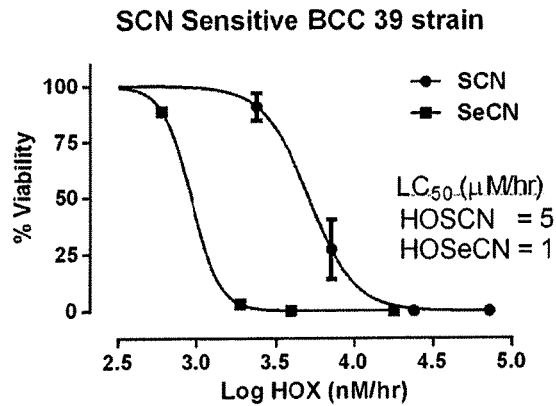
FIGS. 22A-22E: HOSeCN is a more potent antimicrobial agent than HOSCN. Common CF colonizing bacteria such as gram negative bacteria SCN sensitive *Burkholderia cepacia* complex isolate, BBC (FIG. 22A); SCN sensitive *Pseudomonas aeruginosa*, PAO1 (FIG. 22B) and SCN and tobramycin resistant *Pseudomonas aeruginosa* isolates (FIG. 22C) and gram positive methicillin resistant *Staphylococcus aureus*, MRSA SCN sensitive (FIG. 22D) and resistant isolates (FIG. 22E) have decreased cell viability in the presence of either SCN (400 uM) or SeCN (400 uM) with host defense system (LPO+GOX). LPO in the presence of a hydrogen peroxide generating system (glucose oxidase, GOX) can convert both thiocyanate and selenocyante to their respective hypopseudohalous acid species (HOSCN and HOSeCN) that are biocides. SeCN was as effective or superior in killing both thiocyanate susceptible and resistant bacteria. Bacterial inoculums ($10^6$ colony forming units, CFU) were incubated with host defense system for 2 hours at room temperature and bacteria were plated on LB agar plates and cell viability was determined by dilution and counting CFUs. Lethal concentrations that kill 50% of bacteria ($LC_{50}$) were determined by non-linear curve fitting the data. SCN resistance was set at $LC_{50}$>25 uM/hr HOSCN flux.
Figure 22B:
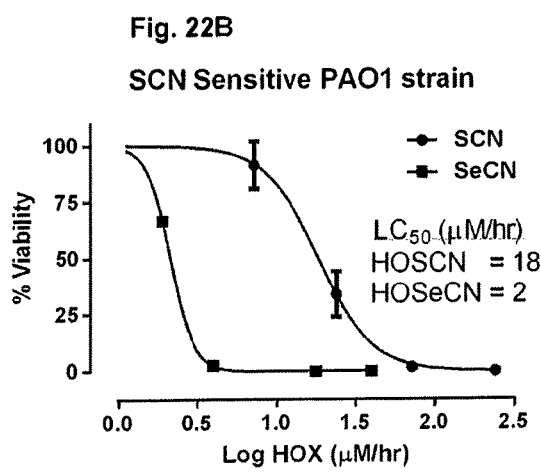
Figure 22C:
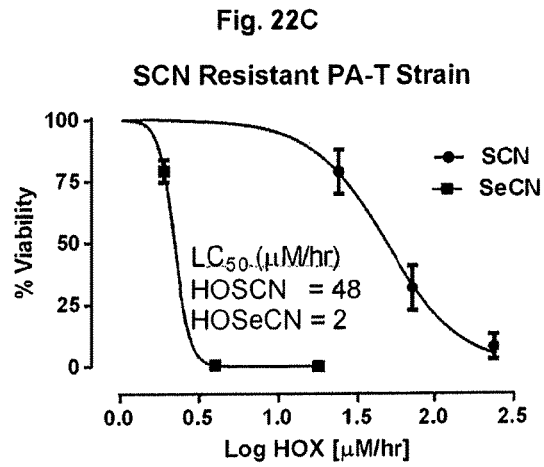
Figure 22D:
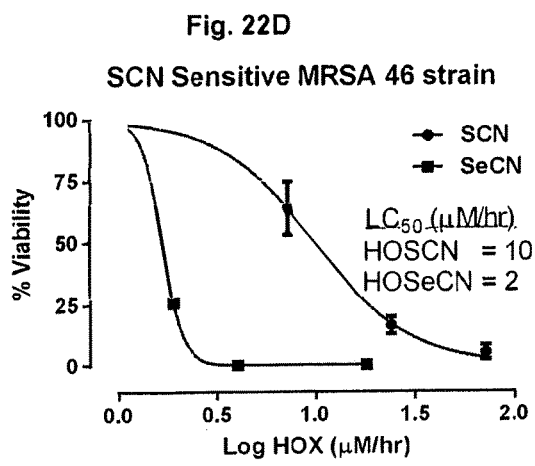
Figure 22E:
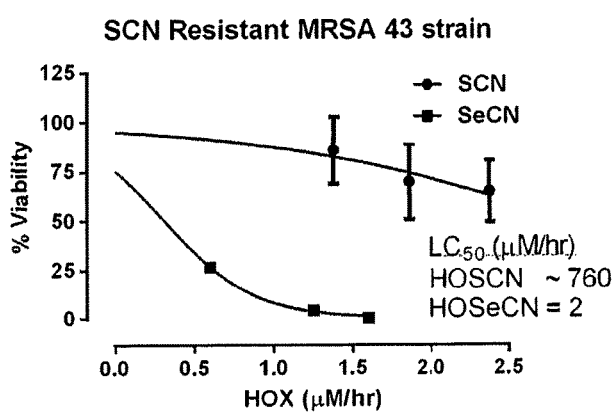

Additional studies determine both leukocyte viability and bacterial viability after ⁻SCN treatments and under simulated ⁻SCN conditions with and without pharmacological inhibition of Sec-TrxR using auranofin and aurothioglucose (Rigobello, M. P., et al. (2008) Gold(I) complexes determine apoptosis with limited oxidative stress in Jurkat T cells. *Eur J Pharmacol* 582, 26-34). Data suggests that Sec-TrxR inhibition sensitizes human lung epithelial cells to HOSCN-mediated cytotoxicity (FIG. 19). These assays have been described to study bacterial killing by neutrophils (Hampton, M. B., and Winterbourn, C. C. (1999) Methods for quantifying phagocytosis and bacterial killing by human neutrophils. *J Immunol Methods* 232, 15-22). Neutrophil death is assessed by flow cytometry using % of Annexin V (apoptosis marker) and propidium iodide (PI, necrosis marker) positive cells in each gate as shown in FIG. 7. Bacterial cell death is measured by serial dilution and by measuring colony forming units as shown in FIGS. 4 and 11.

Mechanism studies examine the effects of extracellular ⁻SCN/HOSCN or SeCN/HOSeCN levels on NFkB (Carlson, B. A., et al. (2011)) and nrf2 (Barrera, L. N., et al. (2012)) activation leading to Sec-TrxR induction. The role of SCN endocytosis on both p65 trafficking to the nucleus and degradation of IkB by western blot and immunocytochemistry is determined. Cellular apoprotein levels of p65 and IkB are determined by western blot analysis and immunocytochemistry. Similar analysis is done for the nrf2/KEAP1 system. Nuclear and cytosolic fractions are obtained using the NE-PER nuclear isolation kit (Thermo) according to manufactures protocol. Membranes are blocked with 5% BSA and probed with primary antibodies for NF-κB p65 or IkB or nrf2 or KEAP1 at 1:500 (Abcam) for 2.5 h at room temperature. The blots are then washed and probed with the peroxidase conjugated goat anti rabbit antibody (Abcam) at a dilution of 1:25,000 for 30 min at room temperature. Proteins are visualized using amersham ECL plus western blotting detection reagents (GE healthcare) according to manufactures protocol. Band densities are quantified using NIH imageJ software.

Phagocytosis and respiratory burst assays are used to assess leukocyte function. Two assays are used to assess the phagocytic ability of neutrophils. First, sheep RBCs optimized with rabbit anti-sheep IgG and stained with Texas Red (as described in Moraes, T. J., et al. (2006) Abnormalities in the pulmonary innate immune system in cystic fibrosis. *Am J Respir Cell Mol Biol* 34, 364-374). Both phagocytosed and nonphagocytosed RBCs are visualized with an inverted EVOS fluorescent microscope (AMG) and scored in terms of the number of phagocytosed RBCs per 100 neutrophils. In the second assay, bacteria labeled with FITC and fixed with 2% glutaraldehyde is used as previously described (Malcolm, K. C., et al. (2011) Bacteria-specific neutrophil dysfunction associated with interferon-stimulated gene expression in the acute respiratory distress syndrome. *PLoS One* 6, e21958). Both phagocytosed and nonphagocytosed bacteria are visualized with an inverted EVOS fluorescent microscope (AMG) and scored for phagocytic index. Respiratory burst is assessed in neutrophils as previously described in Cohen, H. J., and Chovaniec, M. E. ((1978) Superoxide generation by digitonin-stimulated guinea pig granulocytes. A basis for a continuous assay for monitoring superoxide production and for the study of the activation of the generating system. J Clin Invest 61, 1081-1087).

Cytokine array analysis is done using a human 7-flex tissue culture kit (K15003B-1 Meso Scale Discovery) that assesses granulocyte-macrophage colony-stimulating factor (GM-CSF), interleukin 1-bets (IL-1β), interleukin 2 (IL-2), interleukin 5 (IL-5), interleukin 6 (IL-6), interleukin 8 (IL-8) and tumor necrosis factor alpha (TNFα) on a 2400 SECTOR® Imager (MESO SCALE DISCOVERY®).

Both $^-$SCN and $^-$SeCN are expected to have a positive effect on leukocyte function. Data by the inventors show that as extracellular thiol levels are increased there is an increases in intracellular thiols. It is not expected that this only occurs in a cell line and not primary human cells since in vivo a similar relationship between mouse BAL cell and ELF thiol levels and intracellular BAL cell GSH levels when compared to CFTR KO ELF thiol levels and BAL cell GSH levels (Gould, N. S., et al. (2010) Hypertonic saline increases lung epithelial lining fluid glutathione and thiocyanate: two protective CFTR-dependent thiols against oxidative injury. *Respir Res* 11, 119) is seen. Also the inventors have conducted additional studies with primary mouse alveolar macrophages and have shown GSH uptake in vitro, ex vivo and in vivo (Gould, N. S., et al. (2011) Macropinocytosis of extracellular glutathione ameliorates tumor necrosis factor alpha release in activated macrophages. *PLoS One* 6, e25704).

To reduce the potential that the leukocytes may kill the bacteria or bacteria killing leukocytes and to better assess changes in cytokine production and changes in NFkB due to $^-$SCN/$^-$SeCN verses cell death, careful titration of bacteria: leukocyte ratios is done as well as changing incubation times. Another approach is to use PA LPS as a surrogate as described in (Malcolm, K. C., et al. A. (2011) Bacteria-specific neutrophil dysfunction associated with interferon-stimulated gene expression in the acute respiratory distress syndrome. PLoS One 6, e21958; Walker, T. S., et al. (2005) Enhanced *Pseudomonas aeruginosa* biofilm development mediated by human neutrophils. *Infect Immun* 73, 3693-3701; Parks, Q. M., et al. (2009) Neutrophil enhancement of *Pseudomonas aeruginosa* biofilm development: human F-actin and DNA as targets for therapy. *J Med Microbiol* 58, 492-502). The use of pharmacological inhibitors can be problematic and can produce off-target effects, however the two gold compounds have been extensively characterized and have been found to be selective for Sec-TrxR and not other highly similar enzymes such as glutathione reductase.

Example 4

Demonstration of $^-$SeCN as a Therapy for Treatment of Lung Inflammation and Infection Using Wild Type, CFTR KO, and β-ENaC Tg Mouse Models.

Comparison of wild type, CF$^{-/-}$ and β-ENaC Tg mouse pharmacokinetic profile of inhaled $^-$SeCN. Mice are given either one 30 minute nebulization of 0.1, or 0.25% $^-$SeCN and groups of 3 mice sacrificed at 0.5, 1, 2, 4, 6, 8, 24, 48 and 72 hours. Blood is obtained by cardiac puncture and lungs lavaged to obtain plasma and ELF $^-$SeCN concentrations. Tissues are perfused with heparinized saline and lung, liver and kidney are collected for tissue $^-$SeCN determinations by HPLC with electrochemical detection as described for $^-$SCN (Thomson, E., et al. (2010) Identifying peroxidases and their oxidants in the early pathology of cystic fibrosis. *Free Radic Biol Med* 49, 1354-1360). The time to maximal concentration (Tmax), peak maximal concentration (Cmax) and area under the time curve are calculated for wild type and CF$^{-/-}$ mice to assess whether there are uptake and distribution differences. The studies also generate the terminal elimination plasma half-life (T½) for SCN in wild type and CF$^{-/-}$ mice. If the $^-$SeCN plasma T½ is different between wild type, β-ENaC Tg or CF$^{-/-}$ mice, the dosage and/or dosage regimen can be changed accordingly.

Nebulization of $^-$SeCN (0.1, or 0.25%) is evaluated in wild type, β-ENaC Tg and CF$^{-/-}$ mice infected with CF isolate bacteria (PA, BCC and MRSA) for changes in lung inflammation and oxidative stress. Mice are infected with bacteria on Day 0 and therapy started on day 1 and given twice daily by nebulization and provided through Day 7. Three concentrations of nebulized $^-$SeCN (0.1 or 0.25%) are compared in the wild type, β-ENac, and CF$^{-/-}$ mice in the fibrin lung infection model (Table 3). Adult wild-type male C57BL/6 mice originally purchased from Jackson Laboratories (Bar Harbor, ME). C57BL/6J congenic gut-corrected Cftr KO-Tg mice that possess a S489X truncated mutation in the murine equivalent to CFTR and have intestinal specific expression of normal human Cftr driven by the fatty acid binding promoter were originally obtained from Case Western Reserve University's CF Animal Core, as previously described (Kariya, C., et al. (2007) A role for CFTR in the elevation of glutathione levels in the lung by oral glutathione administration. *Am J Physiol Lung Cell Mol Physiol* 292, L1590-1597) or β-ENaC Tg mice (originally from UNC, purchased through Jackson Labortaories).

TABLE 3

Study Design

| Treatments (Nebulized twice daily) | Wild Type Mice | | β-ENaC Tg Mice | | CF$^{-/-}$ Mice | |
|---|---|---|---|---|---|---|
| | PBS | bacteria | PBS | bacteria | PBS | bacteria |
| PBS | 12 mice | 12 mice | 12 mice | 12 mice | 12 mice | 12 mice |
| $^-$SeCN (0.01%) | 12 mice | 12 mice | 12 mice | 12 mice | 12 mice | 12 mice |
| $^-$SeCN (0.05%) | 12 mice | 12 mice | 12 mice | 12 mice | 12 mice | 12 mice |

In the fibrin clot infection model, mice are anesthetized using up to 5% isoflurane and a 24 gauge gavage needle with 30 degree bend is inserted into the distal trachea and 75 μL of solution A followed by 150 μL of air is administered into the airways. Without moving the gavage needle, this is followed by 75 μL of solution B and 300 μL air. Solution A is purified fibrinogen (MP Biomedicals, Solon, OH) dissolved at 10 mg/mL in sterile PBS. Solution B is recombinant thrombin (King Pharmaceuticals, Bristol, TN) dissolved at 5 mg/mL in sterile PBS. CF clinical bacteria strains are cultured overnight in bacterial broth and diluted with PBS to achieve an $OD_{600}$ of 1.0. This is then be diluted into both the fibrinogen and thrombin solutions at 1:200 v/v. Prior calculations indicate that this concentration provides $\sim 1\times 10^7$ cfu/mouse in the 200 μL combined fluid volume.

Figure 32:
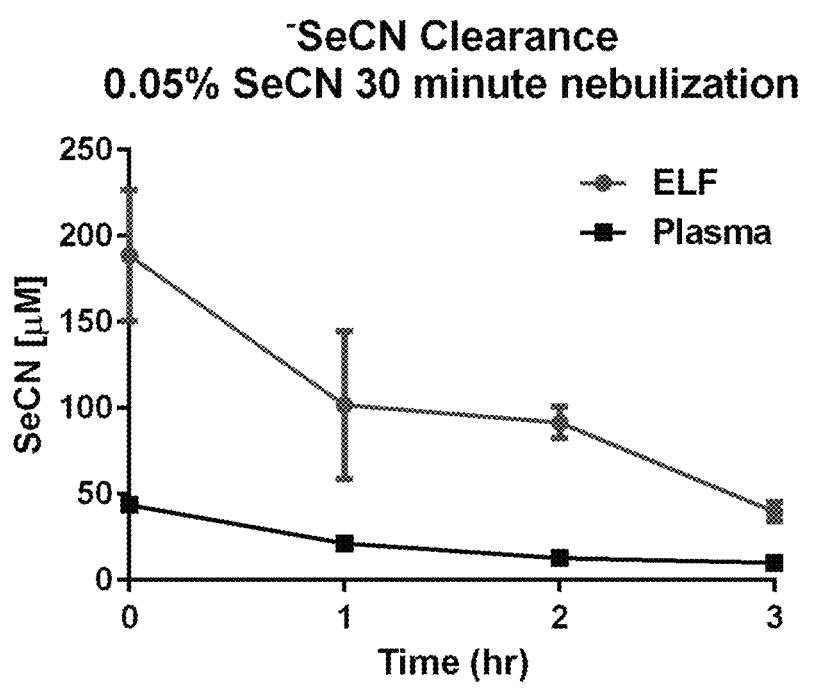

Mice are exposed to aerosolized isotonic (0.9%) or isotonic ⁻SeCN (0.05%) in a Plexiglas nebulizing chamber (see FIG. 32 for data). Isotonicity is maintained by substituting ⁻SeCN for NaCl. All stock solutions are freshly prepared and 10 mL are nebulized over the 30 minute exposure using a pulmosonic nebulizer (DeVilbiss). Outcomes include: 1) changes in serum, ELF, lung and BAL cell GSH, ⁻SCN and SeCN levels; 2) changes is lung tissue Sec-TrxR levels and activity; 3) changes in oxidative stress with assessments of DNA (8-hydroxy-2-deoxyguanosine, 8OH2dG) and lipid (4-hydroxynonenal, 4HNE) oxidation; 4) changes in lung and blood bacterial CFUs; 5) changes in bronchoalveolar lavage fluid (BALF) protein, IgM and lactate dehydrogenase (LDH) as markers of edema and injury; 6) BAL cell counts and differentials as markers of inflammation; 7) changes in BALF cytokine profile (Mouse pro-inflammatory-7 Ultra sensitive kit, IFNγ, IL-1β, IL-10, IL-12p70, IL-6, KC, TNFα, Meso Scale Discovery) as markers of inflammation; and 8) standard histopathology assessments.

Primary outcomes are markers of inflammation and oxidative stress. BAL is performed as previously described (Gould, N. S., et al. (2010) Hypertonic saline increases lung epithelial lining fluid glutathione and thiocyanate: two protective CFTR-dependent thiols against oxidative injury. *Respir Res* 11, 119). Reduced glutathione (GSH) and glutathione disulfide (GSSG) in BALF and tissues are analyzed by HPLC coupled with electrochemical detection as previously described (Thomson, E., et al. (2010) Identifying peroxidases and their oxidants in the early pathology of cystic fibrosis. *Free Radic Biol Med* 49, 1354-1360). ⁻SCN and SeCN are measured by HPLC with electrochemical detection as previously described (Kariya, C., et al. (2007) A role for CFTR in the elevation of glutathione levels in the lung by oral glutathione administration. *Am J Physiol Lung Cell Mol Physiol* 292, L1590-1597). IgM concentrations are quantitatively measured in the BALF using standard ELISA protocol (Bethyl Laboratories, Inc., Montgomery, TX). Total protein is measured in BALF using the bicinchoninic acid (BCA) protein assay (Pierce). The GC/MS 4-HNE assay is modified from previously reported methods (van Kuijk, et al. (1990) Gas chromatography-mass spectrometry of 4-hydroxynonenal in tissues. *Methods Enzymol* 186, 399-406; Rauli, S., et al. (1998) Validation of malondialdehyde and 4-hydroxy-2-trans-nonenal measurement in plasma by NICI-GC-MS. *J Biochem* 123, 918-923). The analysis for 8OH2dG in lung DNA samples uses HPLC coupled with electrochemical and UV detection as described previously (Gould, N. S., (2010) Aging adversely affects the cigarette smoke-induced glutathione adaptive response in the lung. *Am J Respir Crit Care Med* 182, 1114-1122).

Separate sets of animals are used for histopathologic assessments. Mice are cannulated and instilled with 2% paraformaldehyde plus 2% glutaraldehyde in 0.1 M phosphate buffer, pH 7.4 at a pressure of 20 cm of $H_2O$. After 10 minutes of fixation the lungs are removed and 2 mm slices are cut and immersion fixed in 4% paraformaldehyde for overnight fixation and embedded in parafilm. Thick sections (5μ) are cut using a microtome (RM2235, Leica) and sections mounted on slides and stained for H & E and evaluated for signs of lung injury. Standard blinded scoring of perivascular and peribronchiolar edema, cellular infiltrates, and tissue necrosis are assessed on tissue sections.

Statistical Analysis:

Study design uses a nested factorial design with 12 mice per group. Six mice in each group are used for biochemical and microbiological assessments and the other 6 mice are used for histopathological assessment. This study design allows determination of the effect of genetic modification, bacterial infection and treatments and any interaction using a two way ANOVA analysis (Table 3). Power calculation are performed to determine that a group size of 6 would have 90% power to detect a 50% change in BAL KC (based on data in FIG. 8) assuming the standard deviation of each group is 10 pg/ml and alpha=0.05 [PASS: 2-sided 2-sample t test]. Logistics:

Given the large numbers of animals per group and the number of groups, the studies are broken down to 4 trials where the trials test a single ⁻SeCN concentration and changes in biochemical and microbiological assessments are looked for and 4 trials mirroring the above but assessing histopathological changes for each bacterial strain.

⁻SeCN doses are expected to benefit in the wild type, β-ENaC and CF⁻/⁻ mice in the lung infection models. The study design allows the inventor to determine optimal ⁻SeCN treatments tailored for each microbe studied.

Example 5

This example shows the use of ⁻SeCN for the in vivo treatment of pulmonary NTM infections in individuals with CF. This use is demonstrated by examining the susceptibility of a variety of NTM clinical isolates to HOSeCN. By examining these properties in a diverse set of isolates (based on genome analyses), the variability in susceptibilities of different strains of MAC and MABSC species is determined.

Figure 23:
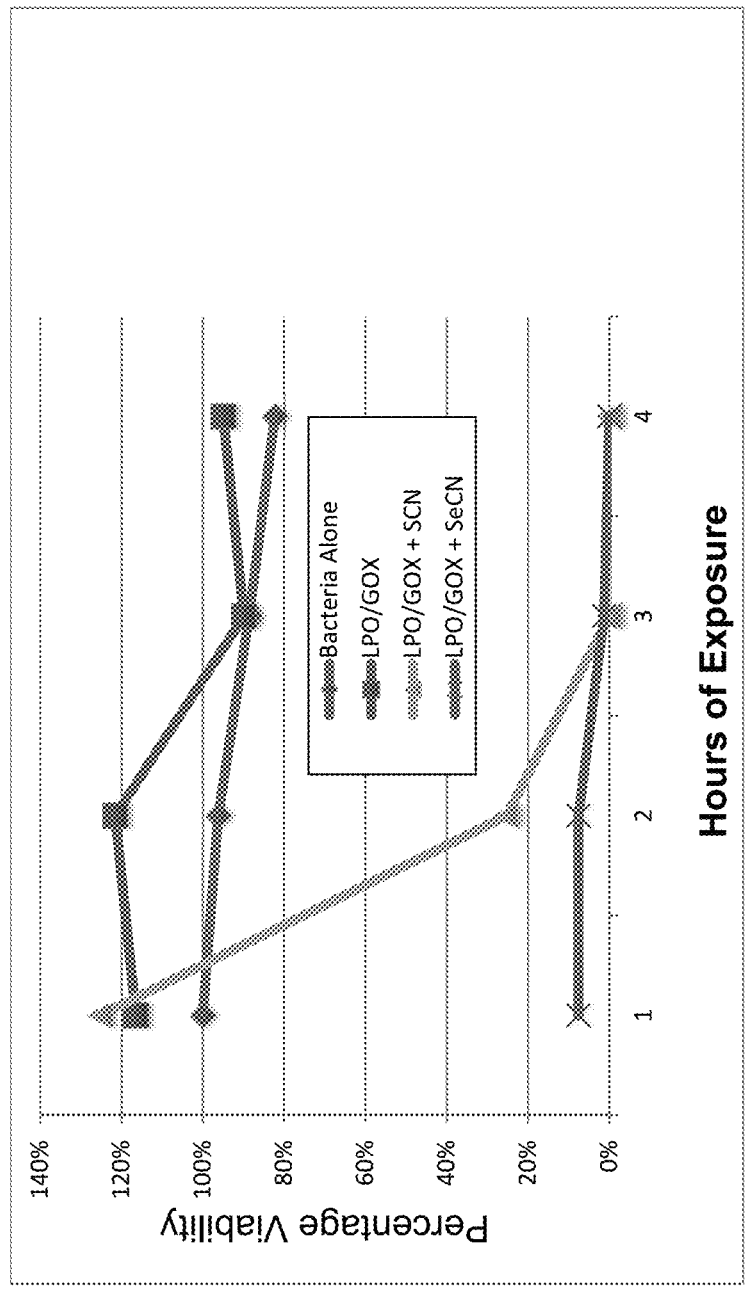
FIG. 23. shows that SeCN is more efficient than SCN at killing M. *Abscessus* in the presence of 1800 mU/mL LPO and 300 mU/mL GOX. A HOSCN-sensitive nontuberculous Mycobacteria (NTM) clinical isolate ws exposed to LPO/GOX with either SCn or SeCN.
Figure 24A:
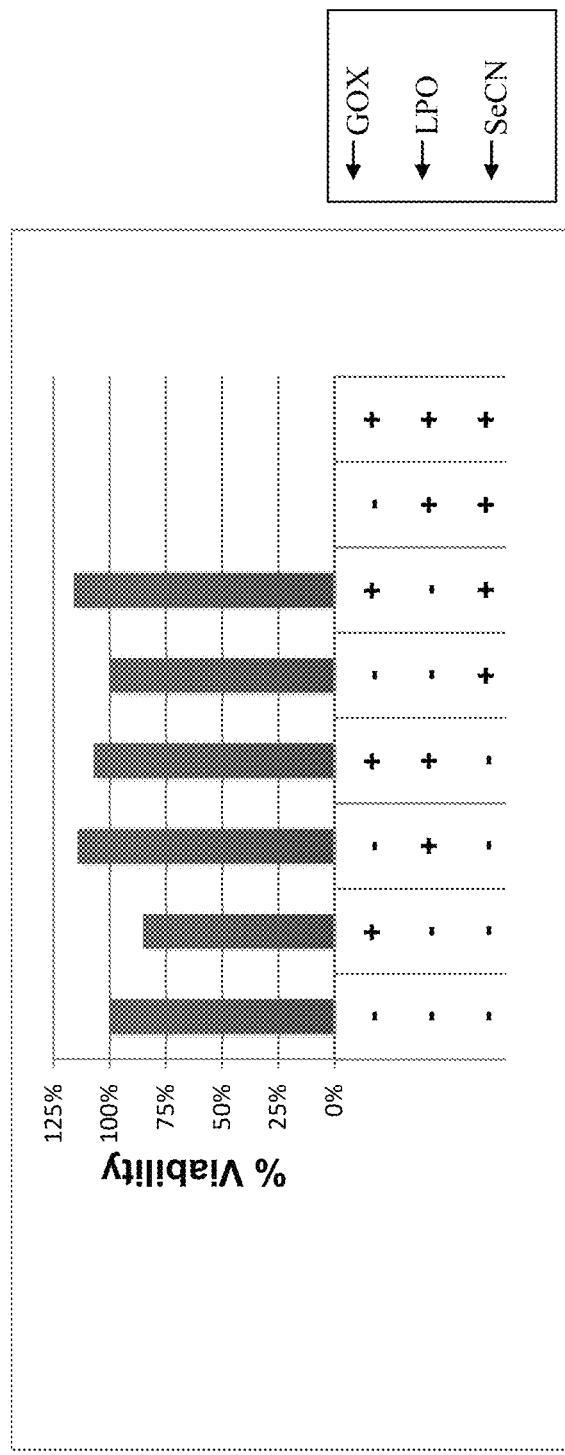
FIGS. 24A and 24B show —SeCN-mediated killing of NTM requires LPO, but not GOX, while LPO/—SeCn has no effect upon *B. Cepacia*.
Figure 24B:
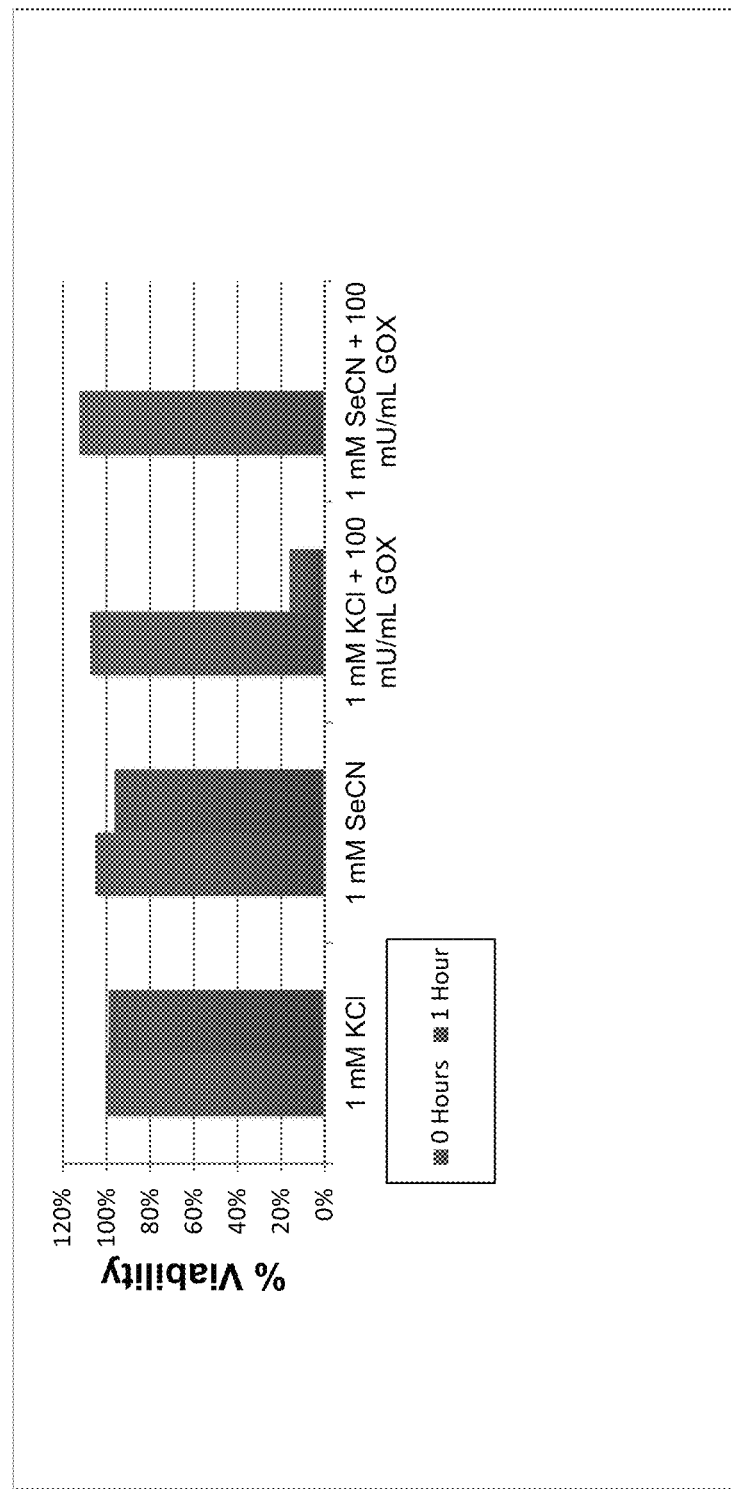

Susceptibility of NTM species to both HOSCN- and HOSeCN-mediated killing. While requiring a higher amount of glucose oxidase (GOX) production of hydrogen peroxide than what was required to kill other bacterial species, HOSCN-mediated killing of NTM was observed with some (but not all) clinical isolates (FIG. 23). However, under these same conditions, substitution of —SCN in the buffer with —SeCN resulted in more efficient killing of NTM. Given the shorter amount of time necessary for —SeCN-mediated killing of NTM compared to other bacteria species (FIGS. 24A and 24B), the possibility that the mechanism responsible for —SeCN-mediated killing of NTM was unique compared to —SCN-mediated killing of NTM and —SeCN-mediated killing of other species is determined. Results demonstrated that —SeCN-mediated killing of NTM only required LPO and —SeCN, while these two components alone had no effect upon *B. cepacia* (FIGS. 24A and 24B). Importantly, LPO and —SCN together did not kill NTM, suggesting a different mechanism of HOSeCN-mediated toxicity. Since killing required LPO, the inventors believe that endogenous $H_2O_2$ production by NTM provided the $H_2O_2$ required for the generation of HOSeCN via LPO and —SeCN.

Figures 25A, 25B:
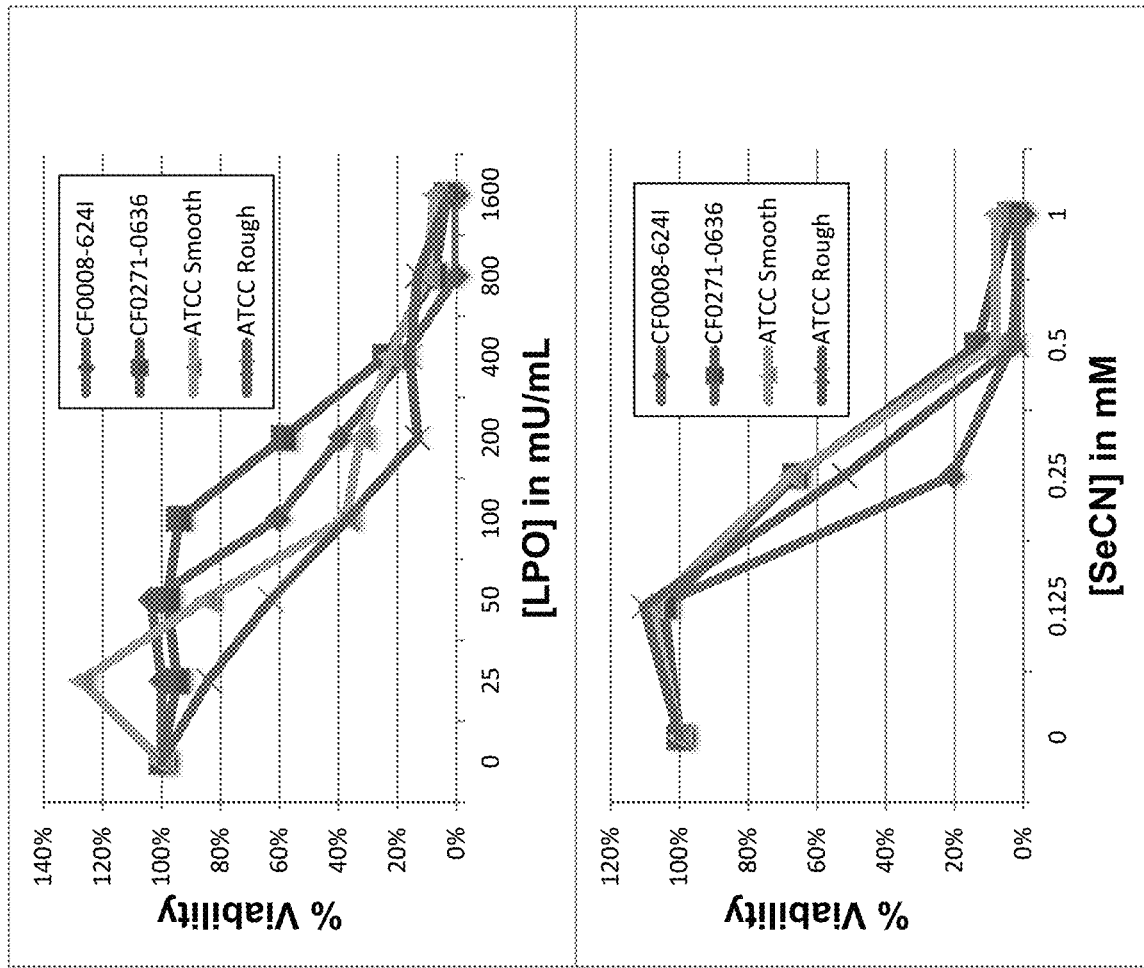
FIGS. 25A and 25B show [LPO] and [—SeCN] dose responses in the killing of NTM.
Figure 26:
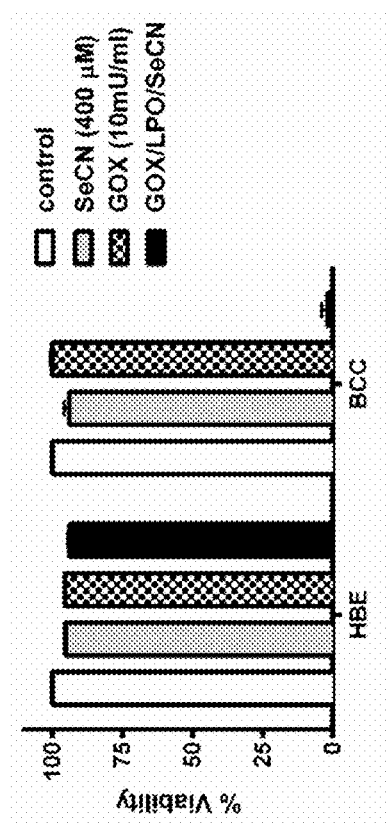
FIG. 26 shows HOSeCN generation spares host lunch epithelial cells while killing bacteria. Human bronchial epithelial cells (HBE) or *Burkholderia cepacia* complex (BCC) were treated for 1 hour in PBS (control), SeCN only (grey bars), glucose oxidase only (hatch bar), or full peroxidase system (black bar) at pH 7.4 and then media replaces and viability assessed 24 hours later. HBE cell viability assessed by MTT and bacterial cell viability assessed by colony forming units.

To examine the variability in susceptibility to HOSeCN-mediated killing amongst clinical NTM isolates obtained from CF airways, four NTM strains were exposed to dose curves of LPO and —SeCN (FIGS. 25A and 25B). While some variations were detected in the sensitivity to killing amongst the isolates, bacterial viability was reduced to less than 10% with all isolates when plated on LB agar immediately after reactions were mixed. Importantly, levels of —SeCN able to reduce bacterial viability were not toxic to human epithelial cells, even in the presence of GOX (FIG. 26).

Figure 27A:
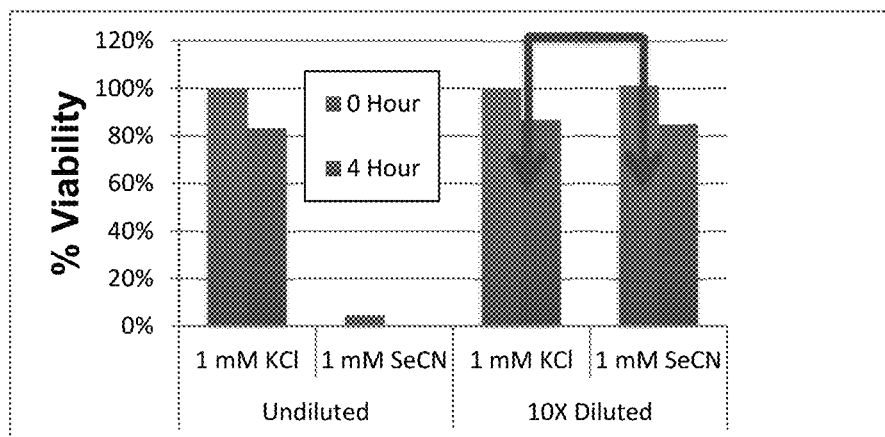
FIGS. 27A-27C show —SeCN-mediaed killing of NTM requires active growth. A clinical isolate of *M. abscessus* was incubated in the listed buffer/media containing LPO at 1000 mU/ml and either KCL or SeCN. At the indicated time, samples were plated on LB agar as undiluted or 10× diluted in PBS. Middlebrook 7H9 was diluted 3 fold in PBS and did not contain catalase.
Figure 27B:
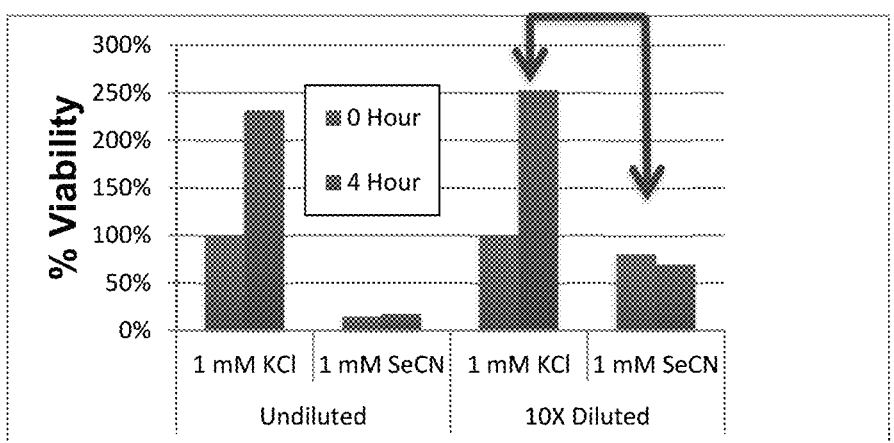
Figure 27C:
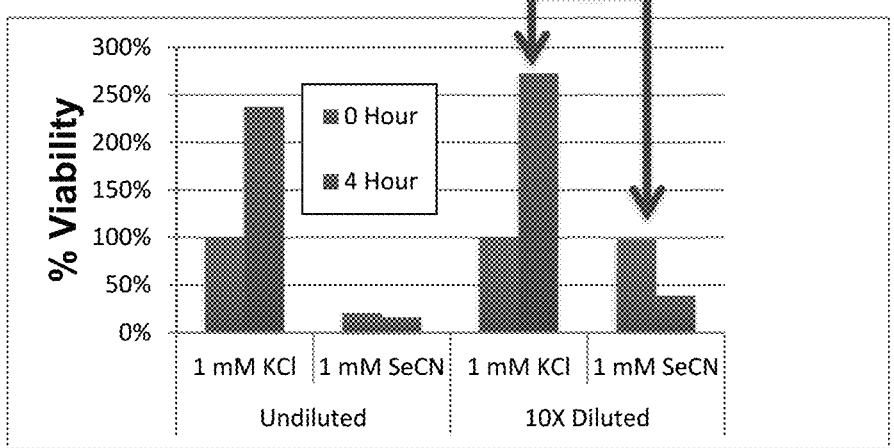

Given the reduced viability observed with immediate plating of LPO/—SeCN reactions on LB agar while —SCN-mediated killing required prolonged incubation, the possibility that HOSeCN generated on the LB agar was responsible for the loss in viability was determined. The inventors demonstrated that this was the case by showing there was no killing detected when samples using PBS buffer as the assay medium were diluted 10-fold before plating on LB agar, which is expected to be due to lowering the LPO and —SeCN concentrations below that required for killing (FIG. 6A); in samples plated undiluted, normal killing was observed. The inventors believe that the LPO in undiluted samples remained active on the LB agar, and that the HOSeCN-mediated killing of NTM, which was not metabolically active in the PBS buffer, requires active growth of the NTM, which occurs on the LB agar. To test this, the PBS buffer was substituted with either Middlebrook 7H9 media (without catalase) or LB broth (FIGS. 27A, 27B and 27C). When the assay was performed using Middlebrook 7H9 media, the LPO/—SeCN prevented bacterial growth from occurring, which is observed as an increase in viability from 0 to 4 hours in the controls, while no increase occurred in LPO/—SeCN that was diluted 10× before plating. In the assay using LB broth, the controls again had growth from 0 to 4 hours, but there was a loss of viability in the LPO/—SeCN condition that was diluted 10× before plating. These results demonstrate that HOSeCN-mediated killing requires the NTM to be metabolically active, indicating that the mechanism of kill is unique as compared to HOSCN-mediated killing.

Sensitivities of various CF clinical isolates or NTM to killing by —SeCN is tested in order to optimize the —SeCN-mediated killing assay to determine the conditions to be used for examining the sensitivity of various clinical isolates and to expose genetically diverse clinical NTM isolates to lactoperoxidase at concentrations ranging from 10 to 1600 mU/mL in the presence of —SeCN at concentrations between 0.1 and 1 mM and examine bacterial viability:

Results shown above have led to two major conclusions: 1) —SeCN is effective at killing all clinical NTM isolates tested when combined with LPO, and 2) the mechanism of this killing is unique, as it does not require exogenous $H_2O_2$ production and that it does require the bacteria to be metabolically active. Based upon these findings, the conditions used in the screening assay is optimized and then used to examine the sensitivity of a diverse range of clinical NTM isolates to —SeCN-mediated killing.

Figure 28A:
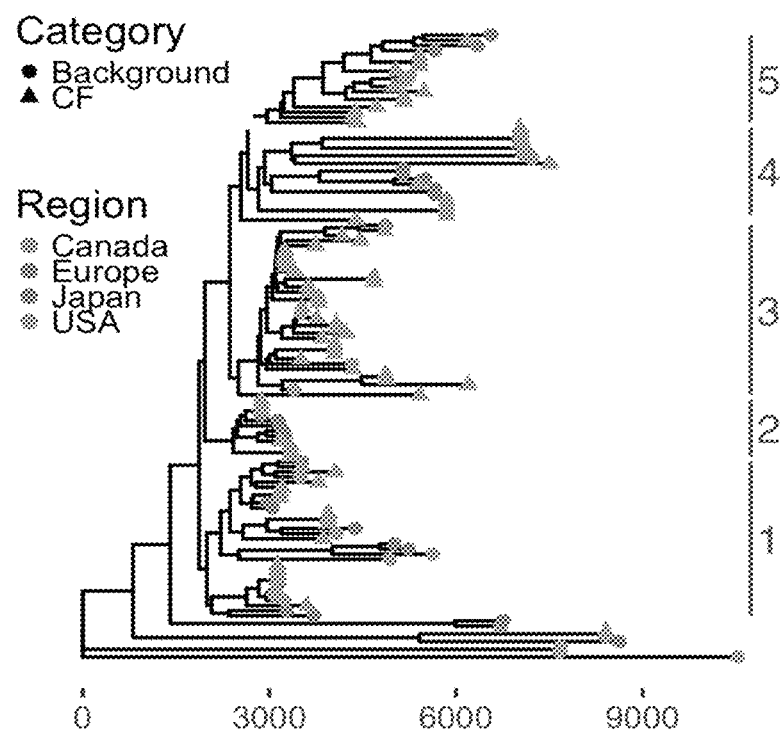
FIGS. 28A and 28 B show phylogenic tress of NTM isolates based on genomic sequence data. The tree in shown in FIG. 28A represent isolates from the *Mycobacterium avium* Complex (MAC) and the tree shown in FIG. 28B represents isolates from the *Mycobacterium abscessus* Complex (MABSC). Horizontal access depict the number of SNPs between isolates, and clades are depicted using vertical bars to the right of the trees.
Figure 28B:
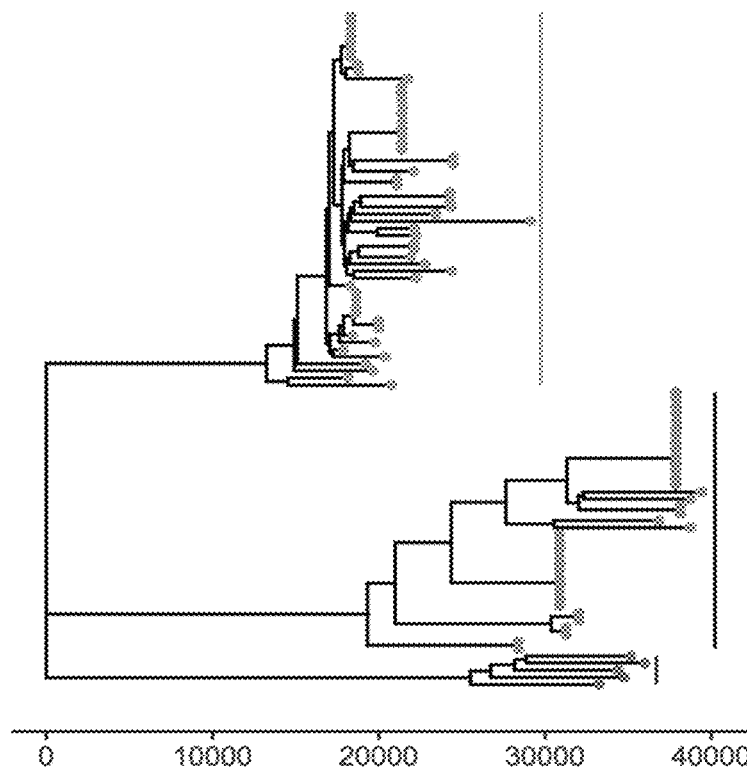

Much of the data provided herein was obtained using a killing assay in which samples containing live bacteria were mixed and then immediately plated after mixing. As noted above, the killing in these experiments was taking place on the LB agar plates. As the samples are plated in small volumes that dry within 5 minutes of plating, the LPO/—SeCN concentrations required for killing in this assay may not accurately reflect what would be necessary in more physiologically-relevant conditions. For this reason, the LPO and —SeCN dose curves is repeated using a "rich" media (i.e. LB broth) and "poor" medias (i.e. serially diluted LB broth) over a 48 hour time course (the amount of time normally required to observe NTM colonies, or lack thereof, in the previous LPO/—SeCN experiments). The same concentration ranges as utilized in the experiments shown in FIGS. 25A and 25B are used. After incubation periods of 0, 1, 2, 4, 8, 24, and 48 hours at 37° C. with shaking, 10 microliters of the reaction mixtures is removed from the sample, serially diluted, and plated on LB agar. After 48 hours of growth on the LB agar, colonies are enumerated. All conditions are performed in triplicate for each NTM isolate. After the optimization has been completed using 2 isolates from each NTM subspecies, a larger screen is undertaken. As depicted in the phylogenetic trees in FIGS. 28A and 28B, analyses of genomic sequences of these NTM isolates confirms their genetic diversity, but it is also important to note the diversity in locations from which the isolates were obtained. Additionally, the clinical outcomes from the individuals with CF from which the isolates were obtained are also variable, with some individuals clearing the infections without intervention, some asymptomatically carrying the infection, and some requiring treatment; the response to treatment also varies. De-identified clinical information associated with these NTM isolates is used to choose isolates that represent the range of clinical outcomes stated above. 6 isolates per clade (as defined in FIGS. 28A and 28B) are examined, ensuring that these isolates represent a diversity of locations, clinical outcomes, and intra-clade genetic diversity, for a total of 42 isolates.

Data Analysis and Interpretation: Analysis of the data is performed be enumerating CFUs and comparing the values of each condition in triplicate to the other conditions by the Kruskal-Wallis test with Dunn's multiple comparisons test. For comparisons amongst the isolates, data is normalized to "percentage viability" for analysis and, depending on whether or not the data is normally distributed, is tested by one-way ANOVA with Tukey's multiple comparisons test. Decreases in CFUs is interpreted as bacterial killing and increases as bacterial growth. As the experiments shown in FIGS. 27A-27C demonstrate, it is not expected that differences in CFUs may be due to bacterial clumping or adherence to the sample vessel, as there is no change in CFUs between the PBS conditions when the sample was diluted 10-fold. It has also been determined that LPO/—SeCN does not have a bacteriostatic role and simply delays colony growth, as plates incubated for prolonged periods of time (10+ days) never grew colonies.

It is expected that killing in LB broth will take less —SeCN and LPO than what was observed with killing on LB agar, as the concentrations will not decrease over time due to diffusion. It is also believed that maximal killing can require 48 hours of incubation before plating. The length of time required can depend both on the rate of growth, and the amount of content in the media that is able to neutralize the active HOSeCN. For this reason, the optimal media for performing the screening assays is considered as the lowest concentration of LB broth that provides maximal killing levels at lower concentrations of LPO and —SeCN.

Further, the role of hydrogen peroxide produced by NTM in the mechanism responsible for —SeCN-mediated killing of NTM is examined by examining the role of endogenously-produced $H_2O_2$ and catalase expression levels in —SeCN-mediated killing of various clinical NTM isolates and identifying the cellular location of —SeCN toxification.

Figure 29:
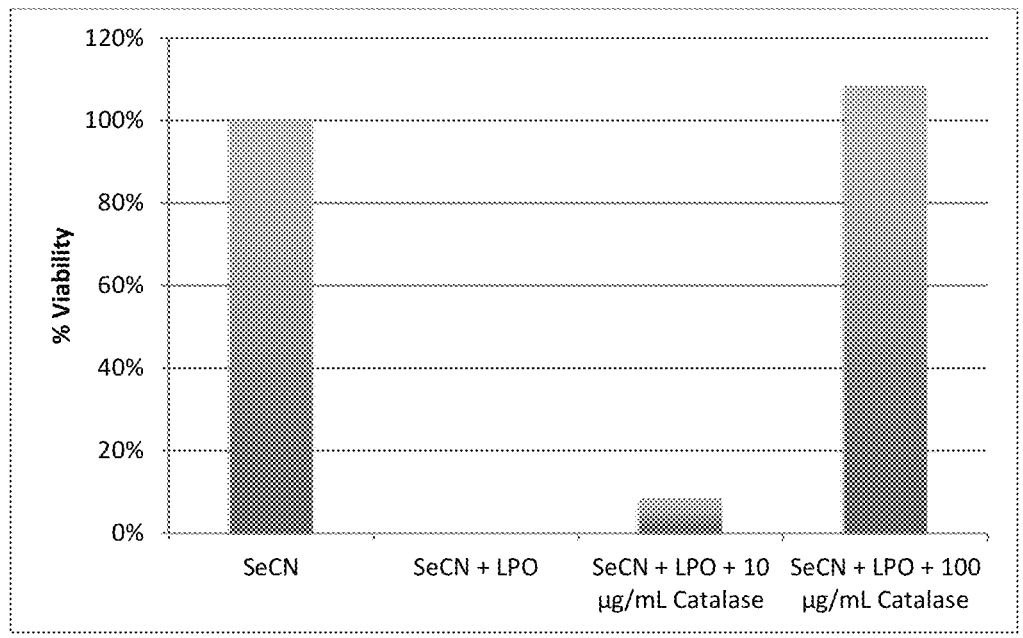
FIG. 29A *M. massiliense* clinical isolate was incubated with 1 mM SeCN and either 1600 mU/mL LPO alone or with catalase.
Figure 30A:
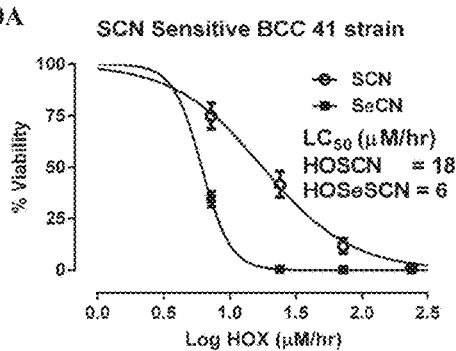
FIGS. 30A-30F show a comparison of bacterial killing between the —SCN/HOSCN and —SeCN/HOSeCN systems in —SCN sensitive and resistant bacterial strains. Comparisons of HOSeCN on SCN sensitive and resistant strains of (FIGS. 30A & 30B) BCC clinical isolates, (FIGS. 30C & 30D) PA clinical isolates, and (FIG. 30E & FIG. 30F) MRSA clinical isolates. Bacteria were incubated for 2 hour with LPO, —SCN or SeCN, glucose and increasing amounts of GOX. The flux (HOX) of either HOSCN or HOSeCN was determined from standard curves of GOX/LPO and either HOSCN or HOSeCN. $LC_{50}$ values were determined by curve fitting the data with nonlinear regression of log (agonist) vs normalized response.
Figure 30B:
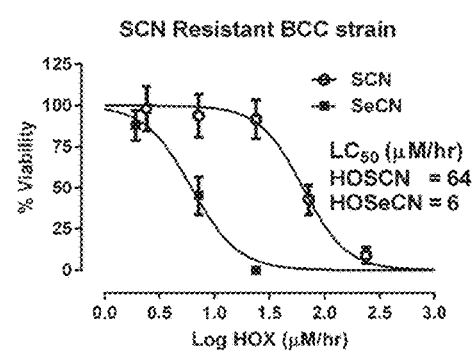
Figure 30C:
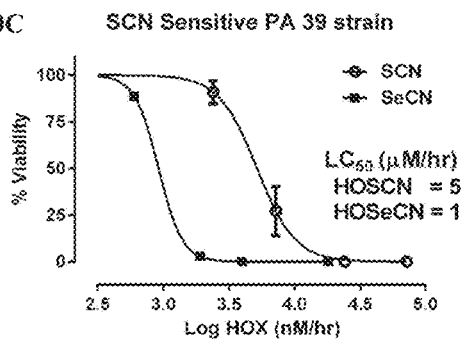
Figure 30D:
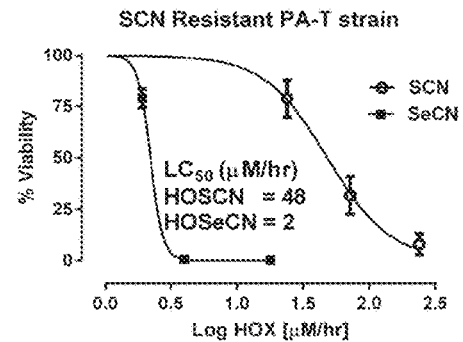
Figure 30E:
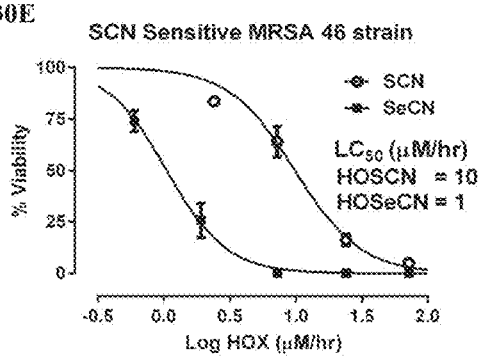
Figure 30F:
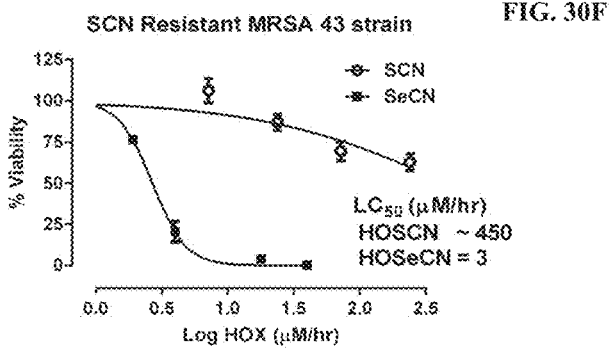

It is well known that NTM species express catalase genes and have the ability to produce $H_2O_2$ (Wayne L G, Diaz G A. Detection of a novel catalase in extracts of *Mycobacterium avium* and *Mycobacterium intracellulare*. Infection and immunity. 1988; 56(4):936-41.). As $H_2O_2$ is a required substrate of LPO and no exogenous source of H2O2 is needed for LPO/—SeCN-mediated killing, it is expected that NTM provides the $H_2O_2$ for utilization by LPO to generate HOSeCN. The inventors have performed a set of experiments that provide evidence that endogenously produced $H_2O_2$ plays a role in the LPO/—SeCN-mediated killing of NTM. In FIG. 29, exogenous catalase is utilized in an attempt to inhibit the LPO-mediated generation of HOSeCN. At high levels of catalase, 100% of the killing was inhibited. The high levels of catalase required for inhibition may be due to several reasons, including instability of the enzyme on LB agar and the possibility that LPO may be bound to and concentrated on the bacterial surface, as has been previously described for Streptococci (Pruitt K M, et al. Lactoperoxidase binding to streptococci. Infection and immunity. 1979; 25(1):304-9). The role of endogenously-produced $H_2O_2$ and catalase in the mechanisms responsible for —SeCN-mediated killing of NTM is further explored to clarify the relevance of this killing in vivo during a pulmonary NTM infection.

A set of NTM isolates identified above as being either highly susceptible or highly resistant to —SeCN-mediated killing is utilized. $H_2O_2$ production in these strains is measured in both actively growing bacteria using a probe, and in 1000 Da MWCO-filtered lysates using a probe and a reactive dye. Catalase activity is measured in both culture supernatants and in lysates using the same methods above and by adding exogenous $H_2O_2$. Lastly, the influence of inhibition of endogenous $H_2O_2$ production or catalase activity on —SeCN-mediated killing, similarly to the experiment performed in FIG. 29 is determined. Exogenous catalase, an $H_2O_2$ scavenger (e.g. sodium pyruvate), or a small molecule bacterial catalase inhibitor is incubated with the bacteria during the LPO/—SeCN killing assay to examine their influence on killing.

In addition, whether the toxification of —SeCN (i.e. generation of HOSeCN) occurs intracellularly or extracellularly is identified. The Amplex™ Red reagent and immunofluorescence microscopy is used to visualize if the LPO is active specifically at the surface of the bacteria. Additionally, NTM is incubated in the presence of LPO/—SeCN and the *Burkholderia* isolate depicted in FIG. 24B; if HOSeCN is present extracellularly during these experiments, it will decrease the viability of the *Burkholderia* (as shown in FIGS. 22A-22E), which was not decreased in the presence of LPO/—SeCN alone. The control for this experiment includes GOX.

It is expected that NTMs that are highly susceptible to —SeCN-mediated killing will produce more $H_2O_2$ and possess less catalase activity. The opposite is expected to be true for highly resistant NTMs. Adding exogenous catalase or an $H_2O_2$ scavenger is expected to inhibit —SeCN-mediated killing, while inhibiting endogenous catalase activity will increase —SeCN-mediated killing. In addition, LPO activity is expected to be localized to the surface of the bacterium. Additional data (not shown) suggests that preincubation of NTM with LPO, followed by washing, then incubation with —SeCN results in substantial killing. It is expected that very little *Burkholderia* will be killed when incubated in the presence of NTM/LPO/—SeCN, as the highly reactive HOSeCN species will be consumed by the NTM.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Thomas, E. L., and Fishman, M. (1986) Oxidation of chloride and thiocyanate by isolated leukocytes. *J Biol Chem* 261, 9694-9702
2. van Dalen, C. J., Whitehouse, M. W., Winterbourn, C. C., and Kettle, A. J. (1997) Thiocyanate and chloride as competing substrates for myeloperoxidase. *Biochem J* 327 (Pt 2), 487-492
3. Hirt, R. P., Muller, S., Embley, T. M., and Coombs, G. H. (2002) The diversity and evolution of thioredoxin reductase: new perspectives. *Trends Parasitol* 18, 302-308
4. Chandler, J. D., and Day, B. J. (2012) Thiocyanate: a potentially useful therapeutic agent with host defense and antioxidant properties. *Biochem Pharmacol* 84, 1381-1387
5. Maduh, E. U., and Baskin, S. I. (1994) Protein kinase C modulation of rhodanese-catalyzed conversion of cyanide to thiocyanate. *Res Commun Mol Pathol Pharmacol* 86, 155-173
6. Chandler, J. D., Nichols, D. P., Nick, J. A., Hondal, R. J., and Day, B. J. (2013) Selective metabolism of hypothiocyanous acid by mammalian thioredoxin reductase promotes lung innate immunity and antioxidant defense. *J Biol Chem* 288, 18421-18428
7. Arner, E. S., Zhong, L., and Holmgren, A. (1999) Preparation and assay of mammalian thioredoxin and thioredoxin reductase. *Methods Enzymol* 300, 226-239
8. Gould, N. S., Gauthier, S., Kariya, C. T., Min, E., Huang, J., and Day, B. J. (2010) Hypertonic saline increases lung epithelial lining fluid glutathione and thiocyanate: two protective CFTR-dependent thiols against oxidative injury. *Respir Res* 11, 119
9. Lorentzen, D., Durairaj, L., Pezzulo, A. A., Nakano, Y., Launspach, J., Stoltz, D. A., Zamba, G., McCray, P. B., Jr., Zabner, J., Welsh, M. J., Nauseef, W. M., and Banfi, B. (2011) Concentration of the antibacterial precursor thiocyanate in cystic fibrosis airway secretions. *Free Radic Biol Med* 50, 1144-1150
10. Thomson, E., Brennan, S., Senthilmohan, R., Gangell, C. L., Chapman, A. L., Sly, P. D., Kettle, A. J., Australian Respiratory Early Surveillance Team for Cystic, F., Balding, E., Berry, L. J., Carlin, J. B., Carzino, R., de Klerk, N., Douglas, T., Foo, C., Garratt, L. W., Hall, G. L., Harrison, J., Kicic, A., Laing, I. A., Logie, K. M., Massie, J., Mott, L. S., Murray, C., Parsons, F., Pillarisetti, N., Poreddy, S. R., Ranganathan, S. C., Robertson, C. F., Robins-Browne, R., Robinson, P. J., Skoric, B., Stick, S. M., Sutanto, E. N., and Williamson, E. (2010) Identifying peroxidases and their oxidants in the early pathology of cystic fibrosis. *Free Radic Biol Med* 49, 1354-1360
11. Leitner, H. M., Kachadourian, R., and Day, B. J. (2007) Harnessing drug resistance: using ABC transporter proteins to target cancer cells. *Biochem Pharmacol* 74, 1677-1685
12. Linsdell, P. (2001) Thiocyanate as a probe of the cystic fibrosis transmembrane conductance regulator chloride channel pore. *Can J Physiol Pharmacol* 79, 573-579
13. Conner, G. E., Wijkstrom-Frei, C., Randell, S. H., Fernandez, V. E., and Salathe, M. (2007) The lactoperoxidase system links anion transport to host defense in cystic fibrosis. *FEBS Lett* 581, 271-278
14. Chandler, J. D., Min, E., Huang, J., McElroy, C. S., Dickerhof, N., Mocatta, T., Fletcher, A. A., Evans, C. M., Liang, L., Patel, M., Kettle, A. J., Nichols, D. P., and Day, B. J. (2015) Antiinflammatory and Antimicrobial Effects of Thiocyanate in a Cystic Fibrosis Mouse Model. *Am J Respir Cell Mol Biol* 53, 193-205
15. Xu, Y., Szep, S., and Lu, Z. (2009) The antioxidant role of thiocyanate in the pathogenesis of cystic fibrosis and other inflammation-related diseases. *Proc Natl Acad Sci USA* 106, 20515-20519
16. Chandler, J. D., Min, E., Huang, J., Nichols, D. P., and Day, B. J. (2013) Nebulized thiocyanate improves lung infection outcomes in mice. *Br J Pharmacol* 169, 1166-1177
17. Mall, M., Grubb, B. R., Harkema, J. R., O'Neal, W. K., and Boucher, R. C. (2004) Increased airway epithelial Na+ absorption produces cystic fibrosis-like lung disease in mice. *Nat Med* 10, 487-493
18. Cantin, A. (1995) Cystic fibrosis lung inflammation: early, sustained, and severe. *Am J Respir Crit Care Med* 151, 939-941
19. Bell, I. M., Fisher, M. L., Wu, Z. P., and Hilvert, D. (1993) Kinetic studies on the peroxidase activity of selenosubtilisin. *Biochemistry* 32, 3754-3762
20. Jones, D. P., and Go, Y. M. (2011) Mapping the cysteine proteome: analysis of redox-sensing thiols. *Curr Opin Chem Biol* 15, 103-112
21. Kanzok, S. M., Fechner, A., Bauer, H., Ulschmid, J. K., Muller, H. M., Botella-Munoz, J., Schneuwly, S., Schirmer, R., and Becker, K. (2001) Substitution of the thioredoxin system for glutathione reductase in *Drosophila melanogaster. Science* 291, 643-646
22. Snider, G. W., Ruggles, E., Khan, N., and Hondal, R. J. (2013) Selenocysteine confers resistance to inactivation by oxidation in thioredoxin reductase: comparison of selenium and sulfur enzymes. *Biochemistry* 52, 5472-5481
23. Nelson, K. J., Klomsiri, C., Codreanu, S. G., Soito, L., Liebler, D. C., Rogers, L. C., Daniel, L. W., and Poole, L. B. (2010) Use of dimedone-based chemical probes for sulfenic acid detection methods to visualize and identify labeled proteins. *Methods Enzymol* 473, 95-115
24. Rhee, S. G., and Cho, C. S. (2010) Blot-based detection of dehydroalanine-containing glutathione peroxidase with the use of biotin-conjugated cysteamine. *Methods Enzymol* 474, 23-34
25. Li, F., Liu, J., and Rozovsky, S. (2014) Glutathione peroxidase's reaction intermediate selenenic acid is stabilized by the protein microenvironment. *Free Radic Biol Med* 76, 127-135
26. Snider, G., Grout, L., Ruggles, E. L., and Hondal, R. J. (2010) Methaneseleninic acid is a substrate for truncated mammalian thioredoxin reductase: implications for the catalytic mechanism and redox signaling. *Biochemistry* 49, 10329-10338
27. Lo Conte, M., Lin, J., Wilson, M. A., and Carroll, K. S. (2015) A Chemical Approach for the Detection of Protein Sulfinylation. *ACS Chem Biol* 10, 1825-1830
28. Okeley, N. M., Zhu, Y., and van Der Donk, W. A. (2000) Facile chemoselective synthesis of dehydroalanine-containing peptides. *Org Lett* 2, 3603-3606
29. Barrett, T. J., Pattison, D. I., Leonard, S. E., Carroll, K. S., Davies, M. J., and Hawkins, C. L. (2012) Inactivation of thiol-dependent enzymes by hypothiocyanous acid: role of sulfenyl thiocyanate and sulfenic acid intermediates. *Free Radic Biol Med* 52, 1075-1085
30. Tenovuo, J., and Pruitt, K. M. (1984) Relationship of the human salivary peroxidase system to oral health. *J Oral Pathol* 13, 573-584
31. Orr, M. D., and Vitols, E. (1966) Thioredoxin from *Lactobacillus* leichmannii and its role as hydrogen donor for ribonucleoside triphosphate reductase. *Biochem Biophys Res Commun* 25, 109-115
32. Rabin, H. R., and Surette, M. G. (2012) The cystic fibrosis airway microbiome. *Curr Opin Pulm Med* 18, 622-627
33. Zhao, J., Schloss, P. D., Kalikin, L. M., Carmody, L. A., Foster, B. K., Petrosino, J. F., Cavalcoli, J. D., VanDevanter, D. R., Murray, S., Li, J. Z., Young, V. B., and LiPuma, J. J. (2012) Decade-long bacterial community dynamics in cystic fibrosis airways. *Proc Natl Acad Sci USA* 109, 5809-5814
34. Kanzok, S. M., Rahlfs, S., Becker, K., and Schirmer, R. H. (2002) Thioredoxin, thioredoxin reductase, and thioredoxin peroxidase of malaria parasite *Plasmodium falciparum. Methods Enzymol* 347, 370-381
35. Dennis, P. P., Ehrenberg, M., and Bremer, H. (2004) Control of rRNA synthesis in *Escherichia coli*: a systems biology approach. *Microbiol Mol Biol Rev* 68, 639-668
36. Buckstein, M. H., He, J., and Rubin, H. (2008) Characterization of nucleotide pools as a function of physiological state in *Escherichia coli*. *J Bacteriol* 190, 718-726
37. Arner, E. S. (2002) Recombinant expression of mammalian selenocysteine-containing thioredoxin reductase and other selenoproteins in *Escherichia coli*. *Methods Enzymol* 347, 226-235
38. Tamura, T., and Stadtman, T. C. (2002) Mammalian thioredoxin reductases. *Methods Enzymol* 347, 297-306
39. Gould, N. S., Min, E., and Day, B. J. (2011) Macropinocytosis of extracellular glutathione ameliorates tumor necrosis factor alpha release in activated macrophages. *PLoS One* 6, e25704
40. Zhang, F., Wang, X., Wang, W., Li, N., and Li, J. (2008) Glutamine reduces TNF-alpha by enhancing glutathione synthesis in lipopolysaccharide-stimulated alveolar epithelial cells of rats. *Inflammation* 31, 344-350
41. Carlson, B. A., Yoo, M. H., Conrad, M., Gladyshev, V. N., Hatfield, D. L., and Park, J. M. (2011) Protein kinase-regulated expression and immune function of thioredoxin reductase 1 in mouse macrophages. *Mol Immunol* 49, 311-316
42. Barrera, L. N., Cassidy, A., Wang, W., Wei, T., Belshaw, N. J., Johnson, I. T., Brigelius-Flohe, R., and Bao, Y. (2012) TrxR1 and GPx2 are potently induced by isothiocyanates and selenium, and mutually cooperate to protect Caco-2 cells against free radical-mediated cell death. *Biochim Biophys Acta* 1823, 1914-1924
43. Day, B. J., van Heeckeren, A. M., Min, E., and Velsor, L. W. (2004) Role for cystic fibrosis transmembrane conductance regulator protein in a glutathione response to bronchopulmonary *pseudomonas* infection. *Infect Immun* 72, 2045-2051
44. Kariya, C., Chu, H. W., Huang, J., Leitner, H., Martin, R. J., and Day, B. J. (2008) *Mycoplasma pneumoniae* infection and environmental tobacco smoke inhibit lung glutathione adaptive responses and increase oxidative stress. *Infect Immun* 76, 4455-4462
45. Chandler, J. D., and Day, B. J. (2015) Biochemical mechanisms and therapeutic potential of pseudohalide thiocyanate in human health. *Free Radic Res* 49, 695-710

46. Cotter, M. J., Norman, K. E., Hellewell, P. G., and Ridger, V. C. (2001) A novel method for isolation of neutrophils from murine blood using negative immunomagnetic separation. *Am J Pathol* 159, 473-481
47. Hampton, M. B., and Winterbourn, C. C. (1999) Methods for quantifying phagocytosis and bacterial killing by human neutrophils. *J Immunol Methods* 232, 15-22
48. Sakurai, A., Nishimoto, M., Himeno, S., Imura, N., Tsujimoto, M., Kunimoto, M., and Hara, S. (2005) Transcriptional regulation of thioredoxin reductase 1 expression by cadmium in vascular endothelial cells: role of NF-E2-related factor-2. *J Cell Physiol* 203, 529-537
49. Rundlof, A. K., Carlsten, M., and Arner, E. S. (2001) *The core promoter of human thioredoxin reductase* 1: cloning, transcriptional activity, and Oct-1, Sp1, and Sp3 binding reveal a housekeeping-type promoter for the AU-rich element-regulated gene. *J Biol Chem* 276, 30542-30551
50. Rigobello, M. P., Folda, A., Dani, B., Menabo, R., Scutari, G., and Bindoli, A. (2008) Gold(I) complexes determine apoptosis with limited oxidative stress in Jurkat T cells. *Eur J Pharmacol* 582, 26-34
51. Moraes, T. J., Plumb, J., Martin, R., Vachon, E., Cherepanov, V., Koh, A., Loeve, C., Jongstra-Bilen, J., Zurawska, J. H., Kus, J. V., Burrows, L. L., Grinstein, S., and Downey, G. P. (2006) Abnormalities in the pulmonary innate immune system in cystic fibrosis. *Am J Respir Cell Mol Biol* 34, 364-374
52. Malcolm, K. C., Kret, J. E., Young, R. L., Poch, K. R., Caceres, S. M., Douglas, I. S., Coldren, C. D., Burnham, E. L., Moss, M., and Nick, J. A. (2011) Bacteria-specific neutrophil dysfunction associated with interferon-stimulated gene expression in the acute respiratory distress syndrome. *PLoS One* 6, e21958
53. Cohen, H. J., and Chovaniec, M. E. (1978) Superoxide generation by digitonin-stimulated guinea pig granulocytes. A basis for a continuous assay for monitoring superoxide production and for the study of the activation of the generating system. *J Clin Invest* 61, 1081-1087
54. Walker, T. S., Tomlin, K. L., Worthen, G. S., Poch, K. R., Lieber, J. G., Saavedra, M. T., Fessler, M. B., Malcolm, K. C., Vasil, M. L., and Nick, J. A. (2005) Enhanced *Pseudomonas aeruginosa* biofilm development mediated by human neutrophils. *Infect Immun* 73, 3693-3701
55. Parks, Q. M., Young, R. L., Poch, K. R., Malcolm, K. C., Vasil, M. L., and Nick, J. A. (2009) Neutrophil enhancement of *Pseudomonas aeruginosa* biofilm development: human F-actin and DNA as targets for therapy. *J Med Microbiol* 58, 492-502
56. Seear, M., Hui, H., Magee, F., Bohn, D., and Cutz, E. (1997) Bronchial casts in children: a proposed classification based on nine cases and a review of the literature. *Am J Respir Crit Care Med* 155, 364-370
57. Kariya, C., Leitner, H., Min, E., van Heeckeren, C., van Heeckeren, A., and Day, B. J. (2007) A role for CFTR in the elevation of glutathione levels in the lung by oral glutathione administration. *Am J Physiol Lung Cell Mol Physiol* 292, L1590-1597
58. van Kuijk, F. J., Thomas, D. W., Stephens, R. J., and Dratz, E. A. (1990) Gas chromatography-mass spectrometry of 4-hydroxynonenal in tissues. *Methods Enzymol* 186, 399-406
59. Rauli, S., Puppo, M. D., Magni, F., and Kienle, M. G. (1998) Validation of malondialdehyde and 4-hydroxy-2-trans-nonenal measurement in plasma by NICI-GC-MS. *J Biochem* 123, 918-923
60. Gould, N. S., Min, E., Gauthier, S., Chu, H. W., Martin, R., and Day, B. J. (2010) Aging adversely affects the cigarette smoke-induced glutathione adaptive response in the lung. *Am J Respir Crit Care Med* 182, 1114-1122

What is claimed is:

1. A method of treating a pulmonary disease comprising administering to a subject in need thereof, an effective amount of a composition comprising selenocyanate, hyposelenocyanite or a selenocyanate conjugate.

2. The method of claim 1, wherein the pulmonary disease is selected from the group consisting of cystic fibrosis, pneumonia, viral pulmonary infection, bacterial pulmonary infection, fungal pulmonary infection, acute respiratory distress syndrome, asthma, chronic obstructive pulmonary disease, interstitial lung disease, bronchiectasis, sarcoidosis, idiopathic pulmonary fibrosis, bronchopulmonary dysplasia, rhinitis, and sinusitis.

3. The method of claim 1, wherein the disease is a result of or is caused by a bacterial infection, a viral infection or a fungal infection.

4. The method of claim 3, wherein the bacterial infection is a result or is caused by a bacteria selected from the group consisting of *Pseudomonas aeruginosa, Burkholderia cepacia* complex, methicillin-resistant *Staphylococcus aureus* and *Mycobacterium*.

5. The method of claim 1, wherein the composition is administered to the subject by an administration route selected from the group consisting of orally, nasally, parenterally, transdermally, intraocularly, topically, drops and inhalation.

6. The method of claim 1, wherein the subject is further administered an antibiotic, an anti-fungal agent, an antiviral agent, an anti-inflammatory agent or a combination thereof.

7. The method of claim 6, wherein the antibiotic is selected from the group consisting of aminoglycosides, ansamycins, penicillins and combinations thereof, first to fifth generation cepalosporins, glycopeptides, lincosamides, lipopeptide, macrolids, monobactams, nitrofurans, oxazolidinones, sulfonamides, tetracyclines, quinolones, fluroquinolones and polypeptides thereof.

8. The method of claim 6, wherein the antifungal agent is selected from the group consisting of polyene antimycotic, imidazoles, triazoles, thiazoles, allyamines, echinocandies and combinations thereof.

9. The method of claim 6, wherein the antiviral agent is selected from the group consisting of adamantines, chemokine receptor antagonists, integrase strand transfer inhibitors, neuraminidase inhibitors, non-nucleoside reverse transcriptase inhibitors (NNRTIs), nonstructural protein 5A (NS5A) inhibitors, nucleoside reverse transcriptase inhibitors (NRTIs) protease inhibitors, purine nucleosides and combinations thereof.

10. The method of claim 6, wherein the anti-inflammatory agent is selected from the group consisting of nonsteroidal anti-inflammatories (NSAIDS), resolvins, glucocorticoids, neutralizing antibodies of cytokines and chemokines and soluble receptor classes, antihistamines, protease inhibitors, and combinations thereof.

11. The method of claim 1, wherein the selenocyanate conjugate is attached by a bond with a thiol or selenol group.

* * * * *